(12) United States Patent
Barrett et al.

(10) Patent No.: US 9,393,249 B2
(45) Date of Patent: Jul. 19, 2016

(54) ANTIMICROBIAL COMPOSITION

(75) Inventors: John Reginald Barrett, Sligo (IE);
James Joseph Brennan, Sligo (IE);
Thomas Patrick Patton, Collooney (IE)

(73) Assignee: INSTITUTE OF TECHNOLOGY SLIGO, Sligo (IE)

( * ) Notice: Subject to any disclaimer, the term of this patent is extended or adjusted under 35 U.S.C. 154(b) by 17 days.

(21) Appl. No.: 12/934,851

(22) PCT Filed: Mar. 26, 2009

(86) PCT No.: PCT/EP2009/053590
§ 371 (c)(1),
(2), (4) Date: Jan. 13, 2011

(87) PCT Pub. No.: WO2009/118379
PCT Pub. Date: Oct. 1, 2009

(65) Prior Publication Data
US 2011/0117071 A1    May 19, 2011

(30) Foreign Application Priority Data

Mar. 26, 2008   (IE) .................................. S2008/0218

(51) Int. Cl.

| | |
|---|---|
| A61K 38/44 | (2006.01) |
| A61P 31/00 | (2006.01) |
| A61P 31/04 | (2006.01) |
| A61P 31/10 | (2006.01) |
| A61K 31/545 | (2006.01) |
| A61K 31/415 | (2006.01) |
| A61K 31/496 | (2006.01) |
| A61K 31/70 | (2006.01) |
| A61K 33/40 | (2006.01) |
| A61K 45/06 | (2006.01) |

(52) U.S. Cl.
CPC ............. *A61K 31/545* (2013.01); *A61K 31/415* (2013.01); *A61K 31/496* (2013.01); *A61K 31/70* (2013.01); *A61K 33/40* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 4,537,764 | A * | 8/1985 | Pellico et al. | 424/50 |
| 4,576,817 | A | 3/1986 | Montgomery et al. | |
| 4,578,265 | A | 3/1986 | Pellico et al. | |
| 4,839,156 | A * | 6/1989 | Ng et al. | 424/53 |
| 4,891,314 | A | 1/1990 | Pauly | |
| 5,098,303 | A * | 3/1992 | Fischer | 433/215 |
| 5,206,150 | A | 4/1993 | Tai | |
| 5,330,357 | A | 7/1994 | Keller | |
| 5,336,494 | A | 8/1994 | Pellico | |
| 5,409,917 | A * | 4/1995 | Robinson et al. | 514/200 |
| 5,453,284 | A | 9/1995 | Pellico | |
| 5,607,681 | A * | 3/1997 | Galley et al. | 424/405 |
| 6,001,380 | A * | 12/1999 | Smith et al. | 424/402 |
| 6,410,059 | B1 | 6/2002 | Khanuja | |
| 2002/0041901 | A1 * | 4/2002 | Murad | 424/616 |
| 2003/0007939 | A1 | 1/2003 | Murad | |
| 2003/0228264 | A1 | 12/2003 | Perna | |
| 2005/0013836 | A1 * | 1/2005 | Raad | 424/400 |
| 2005/0100610 | A1 | 5/2005 | Khanuja | |
| 2006/0003969 | A1 * | 1/2006 | Manandhar | 514/125 |
| 2006/0034816 | A1 * | 2/2006 | Davis et al. | 424/94.4 |
| 2010/0098645 | A1 | 4/2010 | Barrett | |
| 2010/0135926 | A1 | 6/2010 | Barrett | |
| 2014/0023597 | A1 | 1/2014 | Barrett | |
| 2014/0154193 | A1 | 6/2014 | Barrett | |

FOREIGN PATENT DOCUMENTS

| | | |
|---|---|---|
| EP | 0224813 A1 | 11/1986 |
| WO | 88/02600 A | 4/1988 |
| WO | WO96/34612 A1 | 11/1996 |
| WO | 96/38548 A1 | 12/1996 |
| WO | 99/65538 A1 | 12/1999 |

OTHER PUBLICATIONS

Wandan, H.A.L. Causes of the Antimicrobial Activity of Honey. Infection 26 (1998), pp. 30/26 to 31/35.*
V. M. French, R. A. Cooper and P. C. Molan. The antibacterial activity of honey against coagulase-negative staphylococci. Journal of Antimicrobial Chemotherapy (2005) 56, 228-231.*
Product information for NCIMB 9587, downloaded from the internet on Feb. 6, 2013, from the website: http://www.ncimb.com/results.php?parent=culture.*
Katrina Brudzynski. Effect of hydrogen peroxide on antibacterial activities of Canadian honeys. Can. J. Microbiol. 52: 1228-1237 (2006).*
David W. Ball. The Chemical Composition of Honey. Journal of Chemical Education. vol. 84 No. 10 Oct. 2007, pp. 1643-1646.*
Abramson, H., "Principles and Practice of Aerosol Therapy of the Lungs and Bronchi", Annals of Allergy, (1946), vol. 4, pp. 440-456.
Fox, P., "Destruction of the Properties of Some Antibiotics by Hydrogen Peroxide", J. Dairy Science, (1965), vol. 48, pp. 1116-1118.
International Search Report in PCT/EP09/53590; Mar. 7, 2009.
French, et al., "The antibacterial activity of honey against coagulase-negative staphylococci", Journal of Antimicrobial Chemotherapy, Jun. 7, 2005, vol. 56, pp. 228-231.
Non-final office action, dated Sep. 8, 2014, in U.S. Appl. No. 13/721,752.
Non-final office action, dated Sep. 25, 2014, in U.S. Appl. No. 13/732,509.
White, J. W., et al., "The Identification of Inhibine, the Antibacterial Factor in Honey, as Hydrogen Peroxide and its Origin in a Honey Glucose-Oxidase System", Biochimica et Biophysica Acta, 73:57-70 (1963).
Bang, L. M., et al., "The Effect of Dilution on the Rate of Hydrogen Peroxide Production in Honey and Its Implications for Wound Healing", The Journal of Alternative and Complementary Medicine, 9:267-273 (2003).

* cited by examiner

*Primary Examiner* — Frederick Krass
*Assistant Examiner* — Michael P Cohen
(74) *Attorney, Agent, or Firm* — VLP Law Group LLP; Richard G. A. Bone

(57) ABSTRACT

The present invention relates to an improved antimicrobial composition comprising a hydrogen peroxide source and one or more antimicrobial agents. Ideally, the invention relates to an antimicrobial composition comprising (i) hydrogen peroxide source and (ii) an antimicrobial agent and its associated use in therapy, particularly in the treatment of antimicrobial infections.

13 Claims, 34 Drawing Sheets

ANTIMICROBIAL COMPOSITION

FIELD OF THE INVENTION

The present invention relates to an improved antimicrobial composition comprising a hydrogen peroxide source and one or more antimicrobial agents.

BACKGROUND TO THE INVENTION

There are many well-known antimicrobial compositions. For example, such antimicrobial compositions include conventional treatments such as antiseptics and antibiotics. However, there are many potential and real adverse effects associated with the clinical use of such antimicrobial compositions. Adverse effects associated with the use of antibiotics include allergic reactions, destruction of beneficial microflora, development of resistant species of micro-organisms, immune suppression, overgrowth of Candida albicans and undesirable intestinal flora, development of chronic fatigue syndrome and nutrient loss which can result in a nutrient deficiency state. The degree to which these adverse effects are realized is usually dependent on the concentration of antimicrobial administered.

One of the most important of these adverse side effects, is the emergence of antibiotic resistance. The continued emergence of antibiotic resistant pathogens is a serious threat to controlling infections and provides a convincing reason to develop new therapies designed to overcome this problem. Any treatment which overcomes or ameliorates this significant adverse side effect would be desirable.

Furthermore, the side effects associated with the use of potent and potentially toxic antibiotics cannot be overlooked. Again, any treatment which overcomes or ameliorates these adverse side effects would be desirable.

Another conventional treatment used in the treatment of mild to moderate acne vulgaris, is the combination of an antibiotic and benzoyl peroxide. There is now considerable literature on the use of benzoyl peroxide for the treatment of acne and its increased efficacy in combination with antibiotics, particularly erythromycin. This combination therapy has been found to provide an enhanced efficacy over the individual agents, with the potential to decrease the emergence of resistant strains of *P. acnes*. (Bowman, S., Gold, M., Nasir, A., and Vamvakias, G. *Comparison of clindamycin/benzoyl peroxide, tretinoin plus clindamycin, and the combination of clindamycin/benzoyl peroxide and tretinoin plus clindamycin in the treatment of acne vulgaris: a randomized, blinded study*. Journal of Drugs in Dermatology, September-October, 2005).

Furthermore, for example U.S. Pat. No. 4,497,794 is directed to the use of benzoyl peroxide and erythromycin. All the examples in this US patent relate to the use of benzoyl peroxide and erythromycin only. Other publications, relating to the use of benzoyl peroxide and erythromycin include Burkhart C N, Specht K Neckers D, "*Synergistic activity of benzoyl peroxide and erythromycin*"; Skin Pharmacol Appl Skin Physiol.: 2000 September-October; 13(5):292-6 and Eady E A, Farmery M R, Ross J I, Cove J H, Cunliffe W J. "*Effects of benzoyl peroxide and erythromycin alone and in combination against antibiotic-sensitive and-resistant skin bacteria from acne patients*". Br J Dermatol. 1994 September; 131(3):331-6. Both these publications state that the combination of benzoyl peroxide and erythromycin is not synergistic and that the increased benefit is due to the benzoyl peroxide additionally killing the erythromycin-resistant strains. Finally, International Patent publication no. 96/10998 is directed to a topical treatment for acne comprising a peroxide and antibiotic of the lincomycin family. Again, all the examples in this patent relate to the use of benzoyl peroxide only.

Other antimicrobial treatments include silver-containing gels, compounds containing heavy metals and solutions of hydrogen peroxide and natural and synthetic pharmaceutically active substances. However, even these treatments have side effects, for example, high levels of hydrogen peroxide have a toxic effect. In addition, hydrogen peroxide in solution is typically unstable and it is difficult to provide a sustained delivery system for this material.

Additionally, in recent years there has been a resurgence of interest in the therapeutic efficacy of honey, particularly in the area of wound healing. As a natural product, honey offers an attractive alternative to conventional treatments. Many different types of honey have antimicrobial activity. Over the past number of years Manuka honey has been recognised as having superior activity to most other honeys. Manuka honey is known for the treatment of wound infections and its antibacterial activity. However, natural honey as an antibacterial agent has several disadvantages. Firstly, natural honey is composed of a diverse mixture of identified and unidentified organic and inorganic compounds at various concentrations. In this respect it can be expected to demonstrate a degree of variability which may be unacceptable for its use in many clinical applications. Secondly, honey is mainly used for topical application. This is because when honey is diluted by, for example, absorption into the gut it becomes too diluted to have any detectable activity. Finally, honey is a natural product, which will have many additional compounds present and some of these compounds may give rise to an allergic reaction when it is applied.

Thus, for a wide variety of different reasons, conventional antimicrobial treatments available to date have many drawbacks. Thus, there is therefore a need for improved antimicrobial systems which overcome the above-mentioned disadvantages.

STATEMENTS OF THE INVENTION

According to a first general aspect of the present invention, there is provided an improved antimicrobial composition comprising a hydrogen peroxide source and one or more antimicrobial agents for use in therapy, ideally in the treatment and/or prophylaxis of microbial infections.

Ideally, the improved antimicrobial composition is in the form of a combination therapy or combined preparation. The hydrogen peroxide source may be hydrogen peroxide per se or a means for generating hydrogen peroxide ideally in the form of a storage-stable antimicrobial and immunostimulatory system comprising an oxidoreductase enzyme, a substrate for the oxidoreductase enzyme, additional sugars and hydrogen peroxide in an aqueous solution and the system provides a two-stage hydrogen peroxide release in which (a) storage-stable endogenously produced hydrogen peroxide is bioavailable within the system at a level of at least 10 mg per litre for immediate release; and (b) the sustained release of further hydrogen peroxide for at least a twenty-four hour period occurs upon rehydration of the system.

According to a second general aspect of the present invention, there is provided an improved antimicrobial composition comprising a hydrogen peroxide source in the form of a storage-stable antimicrobial and immunostimulatory system comprising glucose oxidase, D-glucose, one or more of sucrose, fructose and/or maltose, and hydrogen peroxide in an aqueous solution wherein the system provides a two-stage hydrogen peroxide release in which (a) storage-stable endogenously produced hydrogen peroxide is bioavailable within the system at a level of at least 10 mg per litre for immediate release; and (b) the sustained release of further hydrogen peroxide for at least a twenty-four hour period occurs upon rehydration of the system. The improved antimicrobial composition of this aspect of the invention may also be used in the treatment and/or prophylaxis of a microbial infection. In this manner, the storage-stable antimicrobial and immunostimulatory system may be used as the antimicrobial composition per se or in combination with one or more antimicrobial agents.

DETAILED DESCRIPTION OF THE INVENTION

In the specification, it will be understood that the term "antimicrobial" or "antibacterial" are used interchangeably herein and cover biocidal or biostatic activity against various types of micro-organisms including but not limited to bacteria, fungi, viruses, yeasts, parasitic or pathogenic micro-organisms and/or moulds.

In the specification, it will also be understood that the term "an antimicrobial agent" encompasses all chemotherapeutic antimicrobial drugs, preferably antibiotics or antifungal, antiviral and antiparasitic agents.

It will also be understood that the term "antimicrobial composition" covers both the hydrogen peroxide source per se (such as the storage-stable antimicrobial and immunostimulatory system described below) or the combination therapy/combined preparation comprising the hydrogen peroxide source and antimicrobial agent.

In this specification, it will be understood that the term "hydrogen peroxide source" covers both hydrogen peroxide per se and/or a means to generate hydrogen peroxide. In a preferred embodiment, the hydrogen peroxide source is the storage-stable antimicrobial and immunostimulatory system (the "antimicrobial system") described below.

In the specification the term "by weight", "percentage by weight" or "w/w %" refers to the weight of the final composition or system. These w/w values are interchangeable with w/v.

Combination Therapy

According to a first general aspect of the present invention, there is provided an improved antimicrobial composition comprising a hydrogen peroxide source and one or more antimicrobial agents.

The hydrogen peroxide source may be hydrogen peroxide per se or a means for generating hydrogen peroxide.

The antimicrobial agent may be an antibacterial antibiotic(s), antifungal antibiotic(s), antiparasitic agent(s) and/or antiviral agent(s).

Ideally, the hydrogen peroxide source and one or more antimicrobial agents are present as part of a combination therapy or combined preparation. In this specification the term "combination therapy" is used broadly. The combination therapy may be produced in one pharmaceutical form comprising both active ingredients or in two separate forms including tablets, capsules, powders, mixtures or solutions. Hence, the term "combination therapy" covers both the simultaneous, sequential and/or separate administration of the hydrogen peroxide source and the antimicrobial agent or agents. Accordingly, the active ingredients of the combination therapy may be administered at substantially the same time or at different times.

Thus, the term "combination therapy" covers the combination of the antimicrobial agent or agents and the hydrogen peroxide source as a single entity, i.e. a combined preparation. In this way, the hydrogen peroxide source may be combined, integrated or sequestered with the antimicrobial agent or agents either during or after manufacture.

Alternatively, the antimicrobial agent or agents may be packaged separately to the hydrogen peroxide source for co-administration. In this situation a set of instructions for co-administration can also be provided. For example, the invention also provides a means by which the systemic use of antimicrobial agents for treating topical infection may be augmented by the simultaneous topical treatment of the infection with the invention.

It will be understood that the antimicrobial composition of the invention should be present in a therapeutically effective amount to kill or inhibit or control the growth of the micro-organisms being treated. However, it may also be possible to use a lower amount of antimicrobial agent due to the synergistic or additive effect between the antimicrobial agent and the hydrogen peroxide. We have surprisingly found that, in some instances, the antimicrobial composition of the invention has a greater antimicrobial efficacy than that achieved by the individual components alone. This effect goes beyond a combination/additive effect and is observed following a reduction in the concentration of the individual antimicrobial agents present in the composition, indicating that the reduced concentration of individual components does not affect antimicrobial activity and unexpectedly indicating that the antimicrobial activity of the composition of the invention is in fact enhanced. We conclude that the increased efficacy of the antimicrobial composition of the invention results from an advantageous action, i.e. some level of synergy, between the hydrogen peroxide and the antimicrobial agent. In this manner, the composition, combination therapy or combined preparation of the invention provides for an efficacy greater than the efficacy of either agent administered alone In particular when a hydrogen peroxide source was used in combination with certain antibiotics and antifungal agents (including but not limited to lincosamides (such as Clindomycin) or cephalosporins (first or second generation such as Zinacef® or Velocef® (Cefuroxime or Cefradine respectively)) a synergistic effect was observed. This is one of the major advantages of the invention. This unexpected effect provides a significant advantage over prior art antimicrobial compositions and provides an improved therapy for the treatment of microbial infections.

Advantageously, this aspect of the invention also provides a means by which the concentration of an antimicrobial may be reduced when combined with hydrogen peroxide for the treatment of microbial infections. For example, the composition of the invention has distinct advantages where use of toxic antimicrobials is medically indicated as the amount of toxic antimicrobial can be reduced.

Finally, advantageously, we postulate that the hydrogen peroxide constituent of the invention provides a means by which antimicrobial resistant organisms may re-acquire antimicrobial sensitivity. It is likely that the non-specific antimicrobial efficacy of the hydrogen peroxide negatively impacts on the mode of resistance of the antimicrobial resistant organism. Resistance to antimicrobials is generally mediated by decreased cell permeability, active efflux of antimicrobial, enzymatic inactivation of the antimicrobial, modification of the antimicrobial receptor site and synthesis of a resistant metabolic pathway. The non-specific random toxicity of hydrogen peroxide may provide a means by which resistance mechanisms can be overcome. This is a significant and surprising effect of the invention and is importantly not just limited to combinations where synergy has been shown to occur.

Another advantageous and significant application of this aspect of the invention is the removal of biofilms, where bacteria encased in slime layers are less susceptible to antibiotics and have been implicated in persistent infections. Already in-vitro tests on biofilms with iodine show inhibition, and hydrogen peroxide also offers potential for biofilm disruption and consequently an increased susceptibility to antibiotics present in the invention. The development of biofilms is of great importance in the treatment of cystic fibrosis and also in wound care. (Costerton, J. W., Stewart, P. S, and Greenberg, E, P. *Bacterial biofilms: a common cause of persistent infections*. Science 1999; 284 (5418): 1318-22/ Kunisada, T., Yamada, K., Oda, S, and Hara, O. *Investigation on the efficacy of povidone-iodine against antiseptic-resistant species*. Dermatology 1997; 195 Suppl 2: 14-8/Presterl, E., Suchomel, M., Eder, M., Reichmann, S., Lassnigg, A., Wolfgang Graninger, W., and Rotter, M. *Effects of alcohols, povidone-iodine and hydrogen peroxide on biofilms of Staphylococcus epidermidis*. Journal of Antimicrobial Chemotherapy, 2007, 60(2):417-420; doi:10.1093/jac/dkm221).

Antimicrobial Agent

As defined previously, the antimicrobial agent of the first aspect of the invention includes, but is not limited to, an antibacterial antibiotic(s), antifungal antibiotic(s), antiparasitic agent(s) and/or antiviral agent(s). Ideally, commercially available antimicrobial agents or chemotherapeutic antimicrobial drugs will be used.

Antibiotics which show beneficial properties when combined with a hydrogen peroxide source include lincosamides and cephalosporins.

Lincosamides (eg. lincomycin, clindamycin) are a class of drugs which bind to the 23s portion of the 50S subunit of bacterial ribosomes and inhibit early elongation of peptide chain by inhibiting transpeptidase reaction. In this sense, they have a similar action to macrolides.

Cephalosporins which are a class of β-lactam antibiotics. β-lactam antibiotics are a broad class of antibiotics that include penicillin derivatives, cephalosporins, monobactams, carbapenems, and β-lactamase inhibitors, that is, any antibiotic agent that contains a β-lactam nucleus in its molecular structure. They are the most widely-used group of antibiotics. Velocef® (Cefradine) is a first-generation cephalosporin antibiotic. Zinacef® (Cefuroxime) is a second-generation cephalosporin antibiotic that has been widely available in the USA as Ceftin since 1977.

Other antibiotics which may be used include:

The macrolides (such as Klacid) are a group of drugs (typically antibiotics) whose activity stems from the presence of a macrolide ring, a large macrocyclic lactone ring to which one or more deoxy sugars, usually cladinose and desosamine, may be attached. The lactone rings are usually 14, 15 or 16-membered. Macrolides belong to the polyketide class of natural products. Erythromycin is a macrolide antibiotic that has an antimicrobial spectrum similar to or slightly wider than that of penicillin, and is often used for people who have an allergy to penicillins. For respiratory tract infections, it has better coverage of atypical organisms, including mycoplasma and Legionellosis.

β-lactam antibiotics (such as amoxicillin) are a broad class of antibiotics that include penicillin derivatives, cephalosporins, monobactams, carbapenems, and β-lactamase inhibitors, that is, any antibiotic agent that contains a β-lactam nucleus in its molecular structure. They are the most widely-used group of antibiotics. Flucloxacillin (INN) or floxacillin (USAN) is a narrow spectrum beta-lactam antibiotic of the penicillin class. It is used to treat infections caused by susceptible Gram-positive bacteria. Unlike other penicillins, flucloxacillin has activity against beta-lactamase-producing organisms such as *Staphylococcus aureus* as it is beta-lactamase stable. However, it is ineffective against MRSA. It is very similar to dicloxacillin and these two agents are considered interchangeable. Flucloxacillin is also available under a variety of trade names including Flopen (CSL) and Floxapen (GSK).

Co-amoxiclav (Augmentin in the UK) is a combination antibiotic containing amoxicillin trihydrate, a β-lactam antibiotic, with potassium clavulanate, a β-lactamase inhibitor. This combination results in an antibiotic with an increased spectrum of action and restored efficacy against β-lactamase producing amoxicillin-resistant bacteria.

We have now specifically shown that two classes of antibiotics demonstrate effects going beyond a mere combination or additive effect with the hydrogen peroxide source. The antibiotics showing synergy fall into two general classes
 (a) Lincosamide (e.g. Clindamycin); and/or
 (b) Cephalosporins (e.g. Cefradine, Cefuroxime—Velocef® and Zinacef®);

As discussed above resistance to antimicrobials is generally mediated by decreased cell permeability, active efflux of antimicrobial, enzymatic inactivation of the antimicrobial, modification of the antimicrobial receptor site and synthesis of a resistant metabolic pathway. The non-specific random toxicity of hydrogen peroxide (whether provided per se or produced by the hydrogen peroxide source of the invention) provides a means by which such resistance mechanisms can be overcome. This effect is likely to extend across the entire spectrum of antibiotic classes, above and beyond those specifically exemplified above. The extent of the effect would generally be expected to vary from one antibiotic to another.

Furthermore, the potent non-specific antimicrobial action of the hydrogen peroxide per se or hydrogen peroxide produced by the hydrogen peroxide source, may also provide an adjuvant effect in combination with other antimicrobials such as antiviral and antifungal agents in which an overall enhanced (additive and/or synergistic) antimicrobiosis is achievable.

Example of suitable antiviral drugs are given on the table below:

| Drug | Viruses | Chemical Type | Target |
| --- | --- | --- | --- |
| Vidarabine | Herpesviruses | Nucleoside analogue | Virus polymerase |
| Acyclovir | Herpes simplex (HSV) | Nucleoside analogue | Virus polymerase |
| Gancyclovir and Valcyte ™ (valganciclovir) | Cytomegalovirus (CMV) | Nucleoside analogue | Virus polymerase (needs virus UL98 kinase for activation) |

-continued

| Drug | Viruses | Chemical Type | Target |
|---|---|---|---|
| Nucleoside-analog reverse transcriptase inhibitors (NRTI): AZT (Zidovudine), ddI (Didanosine), ddC (Zalcitabine), d4T (Stavudine), 3TC (Lamivudine) | Retroviruses (HIV) | Nucleoside analogue | Reverse transcriptase |
| Non-nucleoside reverse transcriptase inhibitors (NNRTI): Nevirapine, Delavirdine | Retroviruses (HIV) | Nucleoside analogue | Reverse transcriptase |
| Protease Inhibitors: Saquinavir, Ritonavir, Indinavir, Nelfinavir | HIV | Peptide analogue | HIV protease |
| Ribavirin | Broad spectrum: HCV, HSV, measles, mumps, Lassa fever | Triazole carboxamide | RNA mutagen |
| Amantadine/Rimantadine | Influenza A strains | Tricyclic amine | Matrix protein/haemagglutinin |
| Relenza and Tamiflu | Influenza strains A and B | Neuraminic acid mimetic | Neuraminidase Inhibitor |
| Pleconaril | Picornaviruses | Small cyclic | Blocks attachment and uncoating |
| Interferons | Hepatitis B and C | Protein | Cell defense proteins activated |

We have also shown that several classes of antifungal agents demonstrate effects going beyond a combination/additive effects with hydrogen peroxide. The antifungal agents found to demonstrate these effects include Clotrimazole; Cyclopiroxalomine; Terbidifine; and/or Ketoconazole. Other antifungal agents may be contemplated.

Hydrogen Peroxide Source

As defined previously, the hydrogen peroxide source of the first aspect of the invention includes a hydrogen peroxide per se or alternatively may be a means for generating a sustained release of hydrogen peroxide.

According to one embodiment, the hydrogen peroxide source of the invention comprises a storage-stable antimicrobial and immunostimulatory system ("the antimicrobial system") comprising an oxidoreductase enzyme, a substrate for the oxidoreductase enzyme, additional sugars and hydrogen peroxide in an aqueous solution and the system provides a two-stage hydrogen peroxide release in which (a) storage-stable endogenously produced hydrogen peroxide is bioavailable within the system at a level of at least 10 mg per litre for immediate release; and (b) the sustained release of further hydrogen peroxide for at least a twenty-four hour period occurs upon rehydration of the system.

Ideally, the oxidoreductase enzyme of the system is selected from one or more of the following glucose oxidase, hexose oxidase, cholesterol oxidase, galactose oxidase, pyranose oxidase, choline oxidase, pyruvate oxidase, glycollate oxidase and/or aminoacid oxidase. It will be understood that each oxidoreductase enzyme acts on a specific substrate. The corresponding substrates for these oxidoreductase enzymes are D-glucose, hexose, cholesterol, D-galactose, pyranose, choline, pyruvate, glycollate and/or aminoacid respectively. It will be understood that a mixture of one or more oxidoreductase enzymes and one or more substrates for the oxidoreductase enzymes may be used.

Preferably, the oxidoreductase enzyme is glucose oxidase, hexose oxidase, galactose oxidase and/or pyranose oxidase and the respective substrate for the oxidoreductase enzyme is D-glucose, hexose, D-galactose and/or pyranose.

According to a preferred embodiment, the oxidoreductase enzyme is glucose oxidase and the substrate is D-glucose.

According to another preferred embodiment, the hydrogen peroxide source is a storage-stable antimicrobial and immunostimulatory system comprises glucose oxidase, D-glucose, one or more of sucrose, fructose and/or maltose, and hydrogen peroxide in an aqueous solution wherein the system provides a two-stage hydrogen peroxide release in which
(a) storage-stable endogenously produced hydrogen peroxide is bioavailable within the system at a level of at least 10 mg per litre for immediate release; and
(b) the sustained release of further hydrogen peroxide for at least a twenty-four hour period occurs upon rehydration of the system.

Further preferred embodiments relating to the storage-stable antimicrobial and immunostimulatory system are expanded on below.

It will be understood that the storage-stable antimicrobial and immunostimulatory system may be used with the antimicrobial agent defined above as part of a combination therapy or may be used on it's own in the treatment or prophylaxis of microbial infections.

This antimicrobial composition, comprising the antimicrobial agent and antimicrobial system defined above, of the invention may be provided in many different physical forms (including but not limited to liquid preparations, solid or semi-solid preparations) depending on the mode of use.

For example, it will be understood that the antimicrobial composition of the invention, may be present in many different administration forms. These forms include but are not limited to forms adapted for topical, enteral or parenteral administration. It will be understood that the antimicrobial agent and/or antimicrobial system may be in the same or different administration form. For example, the hydrogen peroxide source (the antimicrobial system) may in a form adapted for topical use and the antimicrobial agent (e.g. an antibiotic) may be in a form adapted for topical, enteral or parenteral administration.

Forms suitable for topical administration include a topical ointment, cream, lotion, oil, liniment, liquid and/or gel. For example, the antimicrobial composition may be applied epicutaneously, intranasally, via eye and/or ear drops. One particular embodiment provides the antimicrobial composition of the invention in a form adapted for intramammary administration. In this situation, the composition of the invention may be adapted for delivery as part of a teat seal or intramammary depot delivered via the teat canal. Further compositions may be adapted as tissues, bandages or dressings.

Another form suitable for topical administration includes the antimicrobial composition of the invention wherein the antimicrobial composition is in a form adapted for delivery via a dissolvable film strip or strips. In this situation the antimicrobial composition is soluble upon application.

Enteral administration includes, but is not limited to oral administration. Other enteral administration forms include suppositories and enemas. Forms suitable for oral administration include a capsule, pellet, gel cap, pill, pillule, globule, lozenge, dental floss, toothpaste, mouthwash, medicated chewing gum, dissolvable film strips and/or adapted for delivery as part of a mouth guard. According to one embodiment, the antimicrobial composition is in a form suitable for controlled or sustained-release delivery. For example, the oral administration form may have an enteric coating to provide for controlled or sustained-release delivery. This sustained release aspect is important for the treatment of *Campylobacter* infections in poultry and the treatment of *Cryptosporidium* infections in cattle.

Parenteral administration forms include, but are not limited to injection. For example, the antimicrobial composition may be adapted for injection by intramammary administration. This is particularly useful for the treatment of mastitis. Intramammary injection by this means involves injection directly into the teat canal using a tube or syringe with a nozzle of appropriate size, e.g. approx. 1.0 mm. Injection in this situation is directed into a body cavity or abscess.

As discussed above, it will be understood that the hydrogen peroxide source and the antimicrobial agent may be in different administration forms. For example, both may be in a form suitable for topical administration. Optionally, the hydrogen peroxide source may be in a form suitable for topical administration and the antimicrobial agent may be in a form for systemic administration (e.g. enteral administration). Some specific embodiments are highlighted below:

For example, according to one embodiment, the improved antimicrobial composition comprising hydrogen peroxide source and one or more antimicrobial agents may be provided as part of a dressing. Such dressings include gauzes, bandages, films, gels, foams—Lyofoam®, hydrocolloids—Granuflex®, alginates—Kaltostat® (Comvita), hydrogels—Intrasite Gel® and polysaccharide pastes, granules and beads.

Advantageously, according to another embodiment, the antimicrobial composition of the present invention may be present in a gel matrix. Ideally, the improved antimicrobial composition may be present together with a wound-dressing matrix. Ideally, the ratio of antimicrobial composition to wound-dressing matrix is approximately 1:1, although other ratios are contemplated. The wound-dressing matrix may be a collagen or collagen-GAG (glycosaminoglycan) matrix.

According to a further embodiment of the first aspect of the invention, there is provided an antimicrobial composition of the invention for use in a method of therapy.

According to one embodiment, there is provided the antimicrobial composition of the invention for use in a method of treatment of a microbial infection. Furthermore, the antimicrobial composition may also be used in the prophylactic prevention of such microbial infections.

Additionally and according to another embodiment, there is provided the antimicrobial composition of the invention for the regrowth and/or repair of tissues and/or cells, including damaged tissues and/or cells. It will be understood that the system or pharmaceutical composition of the invention enhances an immune response by stimulating the release of interleukin-1 (IL-1). The immunostimulatory properties of the system or pharmaceutical composition of the present invention is responsible for the stimulation, re-growth and repair of damaged tissues and/or cells. It will be understood that the cells include but are not limited to skin cells.

The antimicrobial composition provides a dual functionality in that it is both antimicrobial and immunostimulatory. Advantageously, this dual functionality enables the system to be used for a wide range of therapeutic and prophylactic applications.

Ideally, the microbial infection that can be treated using the antimicrobial composition of the invention is any microbial infection that can be treated by hydrogen peroxide and/or an antimicrobial agent.

It will be understood that the microbial infection may be caused by gram positive bacteria, gram negative bacteria, acid-fast bacteria, viruses, yeasts, parasitic or pathogenic micro-organisms and/or fungi. Acid-fast bacteria include Mycobacteria, including *Mycobacterium tuberculosis* which causes TB. Such microbial infections may be caused by, but not limited to, *Escherichia coli, Staphylococcus aureus, Pseudomonas aeruginosa, Candida albicans, Propionibacterium acnes, Staphylococcus aureus, Staphylococcus epidermidis, Staphylococcus saprophyticus*, Beta haemolytic Streptococci Group A, *Campylobacter coli, Campylobacter jejuni,* Methicillin Resistant *Staphylococcus Aureus* (MRSA), and/or *Mycobacterium tuberculosis.*

In addition the microbial infection may be caused by *Cryptosporidium*, a protozoan pathogen of the Phylum Apicomplexa. *Cryptosporidium* causes a diarrheal illness called cryptosporidiosis. Other apicomplexan pathogens covered by the present application include the malaria parasite *Plasmodium*, and *Toxoplasma*, the causative agent of toxoplasmosis.

Advantageously, the antimicrobial composition may be used in the treatment or prophylactic prevention of MRSA or other antibiotic resistant micro-organisms and bacteria. Thus, the invention overcomes the problem of emerging antibiotic resistant strains of micro-organisms in a non-toxic manner.

This is a major advantage of the present invention over and above conventional systems. For this application, the antimicrobial composition may be administered topically, for example as a topical ointment, cream, lotion, oil, liniment, liquid and/or gel. Optionally, the antimicrobial composition may be administered as part of a tissue or skin wipe. This type of administration may be important in the prophylactic prevention of MRSA and MRSA-type infections.

The microbial infection may be an oral, eye and/or ear infection. The oral infection may be gum disease, oral ulceration and/or an oral hygiene disorder. The oral hygiene disorder may be halitosis and/or gingivitis. Alternatively, the oral infection may be a throat infection or a nasal infection, including nasal Staphylococci infections. An eye infection may include conjunctivitis.

Another condition is mastitis, including wet and/or dry mastitis. Mastitis is a major condition in both humans and animals and is initially caused by microbial infection through damaged skin, blockage of the teat canal, or contact with infected surfaces. In particular, mastitis has a tremendous economic importance for the dairy industry. Thus, alternative therapies to conventional antibiotic therapies are under evaluation. Common causal microorganisms found in mastitis include: *Staphylococcus aureus, Staphylococcus albus, Streptococcus species, Escherichia coli, Salmonella species, Mycobacterium tuberculosis, Fungal mastitis, Candida albicans* and *Cryptococcus neoformans.*

We have advantageously found that the antimicrobial composition can be used in the improved treatment of mastitis. As expanded on previously, the hydrogen peroxide component of the invention may be in a form adapted for intramammary administration, for example in a form adapted for delivery as part of a teat seal, tissue, skin wipe, bandage or dressing or in a form suitable for intramammary injection. The antibiotic component may be administered in the conventional manner.

Additionally, the microbial infection may be a skin and/or nail infection.

Alternatively, the antimicrobial composition may be used in the treatment of fungal skin and/or fungal nail infections. Fungal skin infections include athlete's foot and/or ringworm in humans. In veterinary medicine, fungal skin conditions include, ringworm and the control of zoonotic skin infections. Fungal nail infections include onychomycosis.

Additionally, the antimicrobial composition may be used in the treatment of a skin disorder. The skin disorder may be acne, eczema and/or psoriasis and necrotising fasciitis Advantageously, we have found that the composition invention is as efficacious as conventional anti-acne therapies. It will be understood that acne and eczema may also have a microbial infection component which the system treats. Furthermore, secondary microbial infections of psoriatic lesions caused by scratching can be treated by the system of the present invention. The immunostimulatory effect of the system of the present invention can also aid the re-growth and repair of the damaged tissue or skin cells.

According to another embodiment, the antimicrobial composition of the invention may be used in a method of wound care, including the treatment of a wound and/or the treatment or management of wound sepsis. The wound may be an acute wound, chronic wound, surgical wound, chronic burn and/or acute burn. This aspect of the invention involves both the treatment of a microbial infection and the re-growth/repair of damaged tissues and cells, preferably skin cells. One particular embodiment of this aspect involves the use of the antimicrobial composition in a method of stoma management. The stoma may have resulted from a colostomy, ileostomy, jejunostomy and/or gastrostomy. Another embodiment involves the treatment of diabetic ulcers or wounds.

Alternatively, the antimicrobial composition may be used in the prophylactic prevention of wound sepsis.

According to yet another embodiment of the present invention, the antimicrobial composition may be used in the removal of biofilms.

It will be understood that the antimicrobial composition may be used in both veterinary medicine and human applications.

Many of these specific human applications have been defined previously. However, as defined above the antimicrobial composition may be used in the treatment of general microbial infections and the treatment or management of skin disorders, wound care and/or burn treatment. The treatment or management of wounds and burns can involve both the antimicrobial and immunostimulatory effect of the antimicrobial composition.

Important veterinary applications also involve the treatment of microbial infections and the treatment or management of wound care and/or burn treatment. However, specific conditions include wet and dry mastitis in cattle or other domestic animals, chronic skin infections in dogs (subcutaneous *Staphylococcus* infections), Otitis externa (ear infections), oral care in animals, *Campylobacter* infections in chickens, coliosis, enteric microbial infections in pigs, poultry and cattle, *Cryptosporidium* infections, clearance of zoonotic infections, wound dressing, e.g. horn removal, and abscess treatment. The present invention has particular advantages in veterinary usage, in that it allows the treatment of microbial infections without introducing antibiotics into the food chain.

According to another embodiment of the first aspect of the invention, there is provided the use of the antimicrobial composition of the present invention for the manufacture of a medicament for treating a microbial infection or for the prophylactic prevention of a microbial infection.

Additionally, there is provided the use of the antimicrobial composition of the present invention for the manufacture of a medicament for the repair and/or re-growth of damaged tissues and/or cells. The antimicrobial composition of the present invention ideally enhances an immune response by stimulating the release of interleukin-1 (IL-1) as defined previously.

It will be understood that the microbial infection, skin disorder, wound or other disorder may be treated by a method which comprises the topical, enteral and/or parenteral administration of the system or pharmaceutical composition of the present invention as defined previously.

According to a further embodiment of the first aspect of the invention, there is provided a method for treating a microbial infection and/or the repair and/or re-growth of tissues and/or cells of a patient comprising the steps of applying a therapeutically effective amount of the antimicrobial composition of the invention to an infected area of the patient, preferably by topical, enteral and/or parenteral modes of administration.

According to a second aspect of the invention, there is provided a hydrogen peroxide source in the form of a storage-stable antimicrobial and immunostimulatory system comprising an oxidoreductase enzyme, a substrate for the oxidoreductase enzyme, optional additional sugars, and hydrogen peroxide in an aqueous solution wherein the system provides a two-stage hydrogen peroxide release in which (a) storage-stable endogenously produced hydrogen peroxide is bioavailable within the system at a level of at least 10 mg per litre for immediate release; and (b) the sustained release of further hydrogen peroxide for at least a twenty-four hour period occurs upon rehydration of the system.

Ideally, the substrate for the oxidoreductase enzyme is present up to 90% by weight, water is present up to 20% by weight based on the weight of the total system and the system has a pH from approximately 4 to 8. Optionally, the additional sugars comprise one or more of sucrose, fructose and/or maltose.

In this way, the storage-stable antimicrobial and immunostimulatory system defined above is a hydrogen peroxide source as defined previously. This hydrogen peroxide source may be used as an antimicrobial composition on its own or in combination with one or more antimicrobial agents as defined previously. Thus, it will be understood that the following passages are applicable to the hydrogen peroxide source per se or the combination therapy defined above. In addition, the various administration forms and therapeutic uses for the antimicrobial composition described in relation to the first aspect of the invention are equally applicable to this second aspect, the antimicrobial system alone.

Ideally, the oxidoreductase enzyme of the system is selected from one or more of the following glucose oxidase, hexose oxidase, cholesterol oxidase, galactose oxidase, pyranose oxidase, choline oxidase, pyruvate oxidase, glycollate oxidase and/or aminoacid oxidase. It will be understood that each oxidoreductase enzyme acts on a specific substrate. The corresponding substrates for these oxidoreductase enzymes are D-glucose, hexose, cholesterol, D-galactose, pyranose, choline, pyruvate, glycollate and/or aminoacid respectively. It will be understood that a mixture of one or more oxidoreductase enzymes and one or more substrates for the oxidoreductase enzymes may be used.

Preferably, the oxidoreductase enzyme is glucose oxidase, hexose oxidase, galactose oxidase and/or pyranose oxidase and the respective substrate for the oxidoreductase enzyme is D-glucose, hexose, D-galactose and/or pyranose.

Ideally, the oxidoreductase enzyme is glucose oxidase and the substrate is D-glucose.

According to a preferred embodiment, the storage-stable antimicrobial and immunostimulatory system comprises glucose oxidase, D-glucose, one or more of sucrose, fructose and/or maltose, and hydrogen peroxide in an aqueous solution wherein the system provides a two-stage hydrogen peroxide release in which
(a) storage-stable endogenously produced hydrogen peroxide is bioavailable within the system at a level of at least 10 mg per litre for immediate release; and
(b) the sustained release of further hydrogen peroxide for at least a twenty-four hour period occurs upon rehydration of the system.

According to another preferred embodiment, there is provided a storage-stable antimicrobial and immunostimulatory system comprising glucose oxidase, D-glucose, one or more of sucrose, fructose and/or maltose, and hydrogen peroxide in an aqueous solution
wherein an effective amount of glucose oxidase is present at an activity of at least 10 U per 100 g of system;
wherein D-glucose is present from up to approximately 90%, preferably approximately 20% to 85% by weight based on the weight of the total system;
one or more of sucrose, fructose and/or maltose are present from approximately 10% to 70% by weight based on the weight of the total system;
water is present from 10 to 20% by weight based on the weight of the total system;
the system has a pH from approximately 4 to 8; and
the system provides a two-stage hydrogen peroxide release in which
(a) storage-stable endogenously produced hydrogen peroxide is bioavailable within the system at a level of at least 10 mg per litre for immediate release; and
(b) the sustained release of further hydrogen peroxide for at least a twenty-four hour period occurs upon rehydration of the system.

According to yet another preferred embodiment of this general aspect of the invention, there is provided a storage-stable antimicrobial and immunostimulatory system as defined above comprising glucose oxidase, D-glucose, one or more of sucrose, fructose, maltose and hydrogen peroxide in an aqueous solution
wherein the D-glucose is present from approximately 26% to approximately 43% by weight based on the weight of the total system;
sucrose is present between 0.5% to 2.5% by weight based on the weight of the total system;
fructose is present between 30% to 40% by weight based on the weight of the total system;
maltose is present between 5% to 15% by weight based on the weight of the total system.

According to still another preferred embodiment of this general aspect of the invention, there is provided a storage-stable antimicrobial and immunostimulatory system containing glucose oxidase, D-glucose, one or more of sucrose, fructose, maltose and hydrogen peroxide in an aqueous solution and an optional buffering agent;
wherein an effective amount of glucose oxidase is present at an activity of at least 10 U per 100 g of system;
wherein the D-glucose is present from approximately 33% to approximately 43% by weight based on the weight of the total system;
sucrose is present between 0.5% to 2.5% by weight based on the weight of the total system;
fructose is present between 30% to 40% by weight based on the weight of the total system;
maltose is present between 5% to 15% by weight based on the weight of the total system;
water is present from 10 to 20% by weight based on the weight of the total system;
an optional buffering agent is present in an effective amount of to achieve a system with a pH from approximately 4 to 8; and
the system provides a two-stage hydrogen peroxide release in which
(a) storage-stable endogenously produced hydrogen peroxide is bioavailable within the system at a level of at least 10 mg per litre for immediate release; and
(b) the sustained release of further hydrogen peroxide for at least a twenty-four hour period occurs upon rehydration of the system.

Advantageously, this hydrogen peroxide source is a storage stable, single component system which is ready for immediate use and provides dual functionality in terms of antimicrobial and immunostimulatory activity. In addition this hydrogen peroxide source has increased efficacy in terms of antimicrobial and immunostimulatory effect, when compared to Manuka honey and conventional antimicrobials, such as silver dressing.

The antimicrobial effect of this hydrogen peroxide source is mediated by the two-stage hydrogen peroxide release which advantageously provides two-stage hydrogen peroxide release in a regulated, defined and reproducible manner.

One of the main advantages of this hydrogen peroxide source is that it provides storage-stable hydrogen peroxide for immediate release. This endogenous reservoir provides an immediately available hydrogen peroxide and an immediate antimicrobial effect. Additionally, after re-hydration, the system provides for a second tier of hydrogen peroxide activity involving the sustained release of hydrogen peroxide for at least a twenty-four or forty-eight hour period.

Preferably, the storage-stable endogenously produced hydrogen peroxide is bioavailable within the system at a level of at least 10 mg, preferably 75 mg hydrogen peroxide per litre or parts per million for immediate release. However, it will be understood that the level of endogenously produced hydrogen peroxide which is immediately bioavailable within the system will depend on the amount of oxidoreductase enzyme present in the system. Hence, the level could be much greater than 10 or 75 mg of hydrogen peroxide per litre of the system if the activity of oxidoreductase enzyme used is high. Thus, if the concentration of oxidoreductase enzyme and/or substrate for the oxidoreductase enzyme is increased, then the pool of endogenous hydrogen peroxide increases. For example, we have found that approximately 175 U of oxidoreductase enzyme per 100 g system generates an endogenous pool of approximately 10 mg hydrogen peroxide per litre. Furthermore, approximately 1400 U of oxidoreductase enzyme per 100 g system generates an endogenous pool of approximately 25 mg hydrogen peroxide per litre.

This initial endogenous reservoir of hydrogen peroxide present is storage-stable and remains in the system until the second tier of hydrogen peroxide is released. In the context of this application, storage-stable means that the endogenously produced hydrogen peroxide is maintained within the system for a period up to approximately 36 months. Furthermore, the system does not degrade, separate or lose activity during this time period. The expected shelf life for the system under normal conditions is approximately 36 months. In addition, the system when subject to sterilisation, for example by irradiation, does not deteriorate in quality or activity.

Upon use or application of the system, a second-tier of hydrogen peroxide is released where the level of sustained release hydrogen peroxide produced upon rehydration of the system is at least 10 mg, preferably 20 mg of hydrogen peroxide per litre or parts per million. Again, the level of sustained release hydrogen peroxide generated will depend on the amount of oxidoreductase enzyme and/or substrate for the oxidoreductase enzyme present in the system. We have advantageously found that after a set time period and subsequent dilution/rehydration the amount of sustained release hydrogen peroxide exceeds that present in natural honey. Furthermore, we have advantageously found that the sustained release of further hydrogen peroxide in the system occurs for at least a twenty-eight, if not a forty-eight hour period.

Generally, the immunostimulatory effect of the system is mediated by interleukin-1. The system of the present invention promotes the release of interleukin-1 (IL-1) from skin cells. IL-1 is a cytokine which is also secreted by macrophages, monocytes and dendritic cells. It is an important part of the inflammatory response of the body against infection. It increases the expression of adhesion factors on endothelial cells to enable transmigration of leukocytes to sites of infection. It also acts on the thermoregulation centre of the brain leading to an increased body temperature in the form of a fever. It is therefore called an endogenous pyrogen. The increased body temperature helps the body's immune system to fight infection. This is the initial phase of an inflammatory immune response which augments the antimicrobial activity of the system. The inflammatory response plays a central role in wound healing through its defense against possible infection and by participating in cell and tissue repair and regrowth. The antimicrobial effect of the system of the present invention is aided and complemented by the immunostimulatory effect which aids the regrowth and repair of damaged tissues and/or cells.

According to this specific embodiment of the invention, the hydrogen peroxide source provides a system which gives a regulated, defined and reproducible level of antimicrobial activity and demonstrates a significant difference and increase in activity over a natural honey product. An additional benefit from the system of the invention is the ability to alter the quantity of active and excipient ingredients thereby permitting the production of a range of formulations of various strengths and properties. This includes the ability to optimise the pH for the required target site. Furthermore, the system of allows a high level of quality control with respect to safety and efficacy, batch consistency, potency determination, and a greater control of impurities, in keeping with current Good Manufacturing Practice (cGMP) requirements. It is a still further advantage of the system that it will not cause any allergic reactions, due to its defined composition. Advantageously, this allows for precise labelling instructions as required by the EU legislation for pharmacologically active products.

Each of the preferred components of the antimicrobial and immunostimulatory system are discussed below.

Ideally, the oxidoreductase enzyme, preferably glucose oxidase, is present in the system at an activity of at least 10 U per 100 g of the system. Generally speaking, one unit (U) is that amount of enzyme causing the oxidation of one micromole of glucose per minute at 25° C. and pH 7.0. It will be understood that there must be sufficient oxidoreductase enzyme present to catalyze the substrate and form hydrogen peroxide as needed. Preferably, the oxidoreductase enzyme is present in the system at an activity of at least 100 U, 1400 U or even 5600 U per 100 g of the system.

Ideally, D-glucose is present up to approximately 90%, preferably from approximately 20% to 85%, preferably from 25 to 65%, preferably from 28 to 48%, more preferably from 25 to 45%, even more preferably from 25% to 40%, yet more preferably from 30% to 40%, still more preferably from 30 to 35% by weight based on the weight of the total system. Optionally, D-glucose may be present from approximately 26% to approximately 43% by weight based on the weight of the total system, or alternatively from 33% to approximately 43% by weight based on the weight of the total system or alternatively from 26% to approximately 37% by weight based on the weight of the total system.

Ideally, water is present in the system at a level from approximately 10% to approximately 20% by weight based on the weight of the total system. More preferably, water may be present a level from approximately 10% to approximately 15% by weight based on the weight of the total system. The amount of water present in the system initially is a crucial aspect of the invention. The addition of excess water can lead to instability in the system, as excess water may give rise to hydrolysis of the glucose oxidase, so it is important that water is only initially present within defined parameters. In addition, the system requires sufficient water to permit generation of $H_2O_2$, ease of application and to prevent precipitation of sugars during storage.

Ideally, the system has a pH from approximately 4 to 8, preferably from 5 to 7, more preferably approximately 5.5. The pH is important because it plays a critical role in many therapeutic aspects of the present invention, for example wound healing and also ensures that the oxidoreductase has the correct conditions for needed for optimal activity. Advantageously, the pH of the present system may be set at a pH as required for the particular application. Buffering agents may be used to manipulate the pH. Optionally, the system further comprises a buffering agent, preferably carbonic acid-bicarbonate and/or phosphoric acid/disodium hydrogen phosphate. Preferably, the buffering agent is pre-dissolved in and replaces part of the water of the system. Different concentrations of buffering agent can be used depending on the desired pH.

Ideally, one or more additional sugars in the form of sucrose, fructose and/or maltose are present from approximately 5% to 80%, 10% to 70%, preferably from 30.6% to 61.5%, still preferably from 20% to 50%, even more preferably from 30% to 40% by weight based on the weight of the total system. These "additional sugars" are sugars which are not encompassed by the term "substrate for the oxidoreductase enzyme". The additional sugars play an important role in ensuring the appropriate viscosity is maintained and may act as a viscosity modifying agent. For example, a change in ratios of the additional sugars may result is a corresponding increase or decrease in the viscosity of the system. Ideally, fructose is present from approximately 8 to 50% w/w %, preferably from 25 to 45%, maltose is present from approximately 4 to 15 w/w %, preferably from 5 to 15%, and sucrose is present from approximately 0.5 to 3 w/w %, preferably from 0.5 to 1.5% based on the weight of the total system. Ideally, the additional sugars are present in combination with the substrate for the oxidoreductase enzyme at a ratio of additional sugar to substrate of approximately 10:1 to 0.01:1 preferably from 3.5:1 to 0.05:1. The preferred upper ratio of 3.5:1 is based on minimum substrate for the oxidoreductase enzyme content of 20%, minimum water content of 10% and a maximum additional sugar content of 70%. The preferred lower ratio of 0.05:1 is based on a maximum substrate for the oxidoreductase enzyme content of 85%, a minimum water content of 10% and additional sugar content of 5%.

According to another embodiment of this aspect of the invention, the system may further comprise at least one viscosity modifying ingredient. Ideally, the viscosity modifying agent is selected from one or more of the following: Methyl cellulose, Carboxymethyl cellulose, Hydroxypropyl methyl cellulose, Hydroxyethyl cellulose, Hydroxypropyl cellulose, Carbopol, Polyvinyl alcohol, Polyvinyl pyrrolidone, Hydrogenated vegetable oils, Xanthan Gum and other natural gums, Polyethylene Glycols (low and high molecular weight), Paraffin (liquid, semisolid and solid) and/or Glycerol. The viscosity modifying ingredient may be in addition to the additional sugars mentioned above. Other conventional viscosity modifying agents may also be used.

It will be understood that the additional sugars and/or the viscosity modifying ingredients are added to provide the necessary physical properties needed for the specific application of the system. For example, if the system is used topically, it must have sufficient viscosity to adhere to the applied surface. In this situation it may be desirable to use a viscosity modifying ingredient and/or modify the ratios of additional sugars present. In another situation it may be advantageous to modify the viscosity such that the system may be an effective intramammary preparation.

According to another embodiment of this aspect of the invention, the system may further comprise a buffering agent, preferably carbonic acid-bicarbonate and/or phosphoric acid/disodium hydrogen phosphate.

According to a preferred embodiment of this aspect of the invention, the substrate for the oxidoreductase enzyme, preferably D-glucose, is present from 20 to 85 w/w %, preferably 10 to 85 w/w % and the additional sugars, preferably one or more of sucrose, fructose and/or maltose, are present from 5 to 70 w/w %. Ideally, with fructose from 8 to 50 w/w %, maltose from 4 to 15 w/w % and sucrose form 0.5 to 3 w/w %. The pH of the system will be from 5 to 7 and water is ideally present from 10% to 20% v/v %. Optionally, the ratio of fructose:substrate for the oxidoreductase enzyme:maltose:sucrose is from approximately 1.5:4:2:1 to approximately 3.5:4:1:0.1. A preferred ratio is approximately 4.5:4:1:1.7.

According to a preferred embodiment of this aspect of the present invention, there is provided a storage-stable antimicrobial and immunostimulatory system comprising glucose oxidase, D-glucose and hydrogen peroxide in an aqueous solution;
  wherein D-glucose is present up to 90%, preferably 85%, by weight and water is present up to 20% by weight based on the weight of the total composition; the system has a pH from approximately 4 to 8; and the system provides a two-stage hydrogen peroxide release in which
  (a) storage-stable endogenously produced hydrogen peroxide is bioavailable within the system at a level of at least 10 mg per litre for immediate release; and
  (b) the sustained release of further hydrogen peroxide for at least a twenty-four hour period occurs upon rehydration of the system.

This system may be in many different physical forms, including but not limited to liquid preparations, solid or semi-solid preparations. In order to prepare solid or semi-solid formulations, the ingredients of the system should be manipulated to lower the water content and increase the content of the other components.

The system may be in the form of a liquid preparation. Liquid preparations include but are not limited to a syrup, paste, spray, drop, ointments, creams, lotions, oils, liniments and/or gels. A typical gel includes an alcoholic gel such as isopropanol, ethanol, or propanol and/or a hydrogel.

Alternatively, the system may be in the form of a solid or semi-solid preparation. Solid or semi-solid preparations include but are not limited to capsules, pellets, gel caps, hydrogels, pills, pillules and/or globules. Other means used for conventional drug-delivery can be adopted, for example, liposomal delivery may be contemplated.

According to this second aspect of the invention, the system may be used as an antimicrobial and/or immunostimulatory system per se. Optionally, the system may be used in combination with an antimicrobial agent in accordance with the first aspect of the invention. Administration forms and therapeutic uses are expanded on in relation to the first aspect of the invention. It will be understood that these administration forms and therapeutic uses are equally applicable to this second aspect of the invention when used alone.

Additionally, the system as defined in relation to the second aspect of the invention may be present in the form of and for use as a cosmetic composition together with at least one suitable cosmetic excipient or adjuvant. Such cosmetic excipients or adjuvants are conventional in this field. Cosmetic applications cover many different personal care applications. Ideally, for these types of applications, the system is provided in a form adapted for topical application, although other administration forms previously mentioned may be contemplated. Such cosmetic applications include, but are not limited to, the treatment of hair conditions or the treatment of body odour. Hair conditions include dandruff and the system of the present invention removes the dead skin that accumulates in the scalp and can also treat any underlying microbial infection. The system may also be used as an alternative to the conventional use of hydrogen peroxide for the control of body odour and any associated microbial infection which causes or exacerbates a body odour problem. Additionally, and advantageously the antimicrobial composition or system of the invention may be used in the treatment of skin conditions, for example, acne, eczema, psoriasis, athlete's foot, fungal nail infection.

Another cosmetic application includes the use of the system of the present invention in a method for whitening teeth. Conventional teeth whitening involves applying a solution of hydrogen peroxide or bleach to the outside surfaces of the teeth usually under the supervision of a dentist. As the peroxide penetrates the teeth they become lighter in colour. Advantageously, the system of the present invention is provided in a form adapted for oral delivery via a dissolvable film strip or strips, dental floss, toothpaste, medicated chewing gum, mouthwash and/or adapted for delivery via a mouth guard. Delivery by these means facilitates the lightening of the colour of teeth whereby hydrogen peroxide is released from the system of the present invention. The system of the present invention provides a sustained release of hydrogen peroxide which is ideal for whitening teeth. Furthermore, the system is hydrated and easily tolerated, thereby overcoming the disadvantages associated with conventional whitening systems which employ hydrogen peroxide per se. Thus, the system of the present invention may be used as an alternative hydrogen peroxide source to replace the use of bleach used in many personal care applications.

The process for manufacture of the storage-stable antimicrobial and immunostimulatory system, as defined in the first and second aspects of the invention, and comprising an oxidoreductase enzyme, a substrate for the oxidoreductase enzyme and hydrogen peroxide in an aqueous solution comprises the steps of a. heating the water to a temperature of at least 60° C., preferably from approximately 75° C. to 95° C.;
b. adding the substrate for the oxidoreductase enzyme to the heated water to form a water-sugar solution,
c. cooling the water-sugar solution to a temperature below approximately 40° C. to allow retention of enzyme activity;
d. adding the oxidoreductase enzyme to the water-sugar solution of step (c) with stirring to form hydrogen peroxide at a pre-determined controlled rate; and
e. cooling the resultant mixture from step (d) to room temperature to produce a system with bioavailable and storage-stable endogenously produced hydrogen peroxide at a level of at least 10 mg per litre for immediate release.

Uncontrolled heat treatment of sugars tends to produce carmelisation resulting in a formulation that acquires a yellow to brown colouration. To eliminate carmelisation, and thereby produce a clear material, the manufacturing process above was developed in which the order of addition of sugars and their dissolution by heating is carefully selected to circumvent the carmelisation process.

Preferably, the process comprises the further step of adding of a buffering agent to the system to achieve a pH from approximately 4 to 8, preferably 5 to 7, more preferably 5.5. The buffering agent may be added during or after step (d)

The oxidoreductase enzyme and additional components of the invention are defined above.

Optionally, additional sugars as defined previously may be added to the system in step (b). Ideally, where one or more sugars are added, each sugar is added in a sequentially after the previous sugar has fully dissolved in the water of step (a).

According to one embodiment of this aspect of the invention, the sugars are added in the following sequence: fructose, glucose, maltose and sucrose. Each sugar is dissolved fully in the water by heating to approximately 90° C. before the next sugar is added. Alternatively, the sugars can be prepared as above but under a vacuum at approximately −0.5 Bar. This vacuum reduces the boiling point of the sugars to a temperature of less than 90° C. thereby preventing discoloration.

Optionally, at least one viscosity modifying ingredient may be added to the system during the above process. Ideally the viscosity modifying ingredient is selected from polyethylene glycol, glycerol and/or liquid paraffin. Other conventional viscosity modifying ingredients may be contemplated.

Once the system of the present invention is made according to the above process, the system of the invention may be packaged in an opaque, impermeable container. This prevents the further production of hydrogen peroxide, which can only be reinitiated when in an aerobic atmosphere.

The system generated according to the above process may be a liquid solution, solid or semi-solid preparation. After manufacture, the system may then be processed into the desired end product i.e. administration form, such as solid or semi-solid form suitable for the different forms of administration discussed previously. For example, the system may be combined with an alcoholic gel to provide a gel form suitable for administration. Additionally, the system may be incorporated onto various commercially available dressings.

The system may also be subjected to post-manufacturing sterilisation, by for example, irradiation. Such post-manufacture sterilisation has no negative effect on the hydrogen peroxide source.

The invention will now be illustrated by the following non-limiting examples with reference to the following figures, in which:

FIG. 1a shows a microbial inhibition profile of Manuka honey on *Staphylococcus aureus*. Manuka honey demonstrates a two tier inhibition profile. The first tier of microbial inhibition activity occurs between dilutions 50% to approximately 6.25% and the second tier of microbial inhibition activity occurs at dilutions 3.125% to approximately 0.195%;

FIG. 1b shows a microbial inhibition profile of pH adjusted Manuka honey on *Staphylococcus aureus*. Adjusting the pH of Manuka honey from its natural pH of approximately 4.0 to a pH of 6.8 does not affect the microbial inhibition profile;

FIG. 1c shows a microbial inhibition profile of pH adjusted Manuka honey to which an excess of catalase has been added on *Staphylococcus aureus*. Manuka honey pH adjusted to near a neutral pH followed by the addition of catalase in excess alters the microbial inhibition profile of the honey. The first tier of microbial inhibition is only slighted affected but the second tier is significantly affected indicating that the antibacterial effect in the second tier is primarily the result of hydrogen peroxide liberation;

FIG. 2 shows a microbial inhibition profile of Manuka honey and a prototype formulation on *Staphylococcus aureus*. The prototype formulation demonstrates greater activity compared to that of the Manuka honey;

FIG. 3a shows the results of a microbial inhibition assay using gel based prototype formulations on *Staphylococcus aureus*, *E. coli* and *Candida Albicans*. Both cellulose based gels demonstrate a decrease in stability and neither cellulose based gel formulation is as active as the prototype formulation as evidenced by the smaller zones of inhibition in diffusion assays (compare FIG. 3a (gels) with FIG. 3b (prototype formulation));

FIG. 3b shows the results of a microbial inhibition assay of the prototype formulations on *Staphylococcus aureus*. Large zones of inhibition are evident indicating activity;

FIG. 4a shows the results of microbial inhibition assay of Glucose//glucose oxidase only formulations on different bacteria. Microbial inhibition assays of 4 replicate of 75% D-glucose with 0.5% GOX 5600 U/g in wells and their antimicrobial activity against a number of different bacteria. These formulations demonstrate a limited degree of antibacterial activity. This activity is below that observed with the prototype antimicrobial formulation described in Example 2 as evidenced by the smaller zones of inhibition in Well/Disc diffusion assays (compare FIG. 4a (gels) with FIG. 4b (prototype));

FIG. 4b shows the results of microbial inhibition assay of the prototype formulation against a number of different bacteria FIG. 5a shows the activity of $A^3IS$ containing different GOX (5600 U/g) enzyme concentrations against *S. aureus*. Varying the glucose oxidase content in $A^3IS$ and its affect on the inhibition profile was measured. The antibacterial activity of $A^3IS$ increases proportionally to the concentration of glucose oxidase. A substantial antibacterial effect is attained at an enzyme concentration of 0.05%;

FIG. 5b shows $H_2O_2$ generation over time by $A^3IS$ containing 0.5% sigma Aldrich GOX enzyme 5600 U/g diluted 50% (C1), 25% (C2), 12.5% (C3) or 6.25% in de-ionised water (DI). $A^3IS$ generates significantly increased levels of hydrogen peroxide compared to Manuka honey diluted at 50% in DI water;

FIG. 5c shows $H_2O_2$ generation over time by $A^3IS$. Production of $H_2O_2$ by $A^3IS$ with 0.5% sigma Aldrich GOX enzyme 5600 U/g and diluted 25% in DI water) is maintained for a period of at least 48 h;

FIG. 5d shows that $A^3IS$—antimicrobial activity increases with increased glucose oxidase concentration. Potency/efficacy is dependant on the concentration of glucose oxidase in A³IS formulations. Results show an increase in efficacy with increasing glucose oxidase concentration when tested on *Staphylococcus aureus, Pseudomonas aeruginosa* and *Escherichia coli*;

FIG. 6 shows the stability results and retention of $H_2O_2$ reservoir by A³IS over a ten month period. The available $H_2O_2$ reservoir produced by A³IS is storage stable. The level of available $H_2O_2$ present was initially determined immediately after being placed into tubes and again after a period of 7 and 10 months had elapsed. There is no evidence of a loss of available $H_2O_2$ within the A³IS formulation, thus, indicating stability. Similar results have been obtained with several other batches.

FIG. 7a shows antimicrobial activity in an A³IS formulation on *Staphylococcus aureus* over 3 months. The antimicrobial activity in an A³IS formulation on *Staphylococcus aureus* demonstrates a consistent level of antimicrobial activity over time as determined by zones of inhibition measured at each sampling time point and the results graphed using 95% confidence limits during a period of 3 months;

FIG. 7b shows the antimicrobial activity in an A³IS formulation on *Staphylococcus aureus* over 14 months. The antimicrobial activity in an A³IS formulation on *Staphylococcus aureus* demonstrates a consistent level of antimicrobial activity over time as determined by zones of inhibition measured at each sampling time point and the results graphed using 95% confidence limits during a period of 14 months;

FIG. 8a shows the A³IS antimicrobial activity against *Staphylococcus aureus*, NCCLS kill curve method. Antimicrobial activity of A³IS against *Staphylococcus aureus*, as determined by an NCCLS kill curve method. A³IS has increased efficacy compared with Manuka honey and comparable efficacy to silver dressing;

FIG. 8b shows the A³IS antimicrobial activity against *Staphylococcus aureus*, a Medical Device Manufacturer's Specific Method. Antimicrobial activity of A³IS against *Staphylococcus aureus*, as determined by a Medical device manufacturer's specific protocol. A³IS has increased efficacy compared with Manuka honey and comparable efficacy to silver dressing;

FIG. 8c shows the A³IS—antimicrobial activity against beta haemolytic Streptococci Group A. Results of an inhibition assay (3 day repeats) for A³IS, Medihoney® and a 10% phenol gel tested against 5 clinical isolates of the Beta haemolytic Streptococci Group A. A³IS is at normal pH 5.5 (test material A) and pH 7 (test material B), a negative control of A³IS containing no GOX is included. Formulation A³IS demonstrates comparable in vitro efficacy to a 10% phenol gel and is superior to Medihoney®;

FIG. 8d shows the A³IS—antimicrobial activity against *Campylobacter*. Results of an inhibition assay (3 day repeats) for A³IS, Manuka honey and a 10% phenol gel when tested against 5 clinical isolates of *Campylobacter* spp. Formulation A³IS is at normal pH 5.5 (test material A) and pH 7 (test material B), a negative control A³IS containing no GOX is included. Results indicate significant anti-*Campylobacter* in-vitro efficacy and the superiority of A³IS over Manuka honey;

FIG. 9a shows the A³IS—antimicrobial activity against *P. acnes*. A³IS activity against *P. acnes* under varying incubation conditions: light and dark aerobic, light and dark anaerobic. A³IS demonstrates a high level of activity against *P. acnes*, indicating the materials potential for topical acne application;

FIG. 9b shows the A³IS—antimicrobial activity against *P. acnes*. Antimicrobial activity of A³IS and currently available anti-acne commercial products including some commercial products which incorporate antibiotics are shown. A³IS demonstrates a high level of comparable activity to commercially available anti acne products indicating the materials potential for topical acne application;

FIG. 10 shows the A³IS antimicrobial activity against 8 strains of MRSA on three different days and compared to a 10% phenol standard and to Manuka honey. Formulation A³IS is at normal pH 5.5 (test material A) and pH 7 (test material B), a negative control A³IS containing no GOX is included. The results demonstrate significant in vitro anti-MRSA efficacy and the superiority of A³IS over Manuka honey and a 10% phenol gel control;

FIG. 11a shows A³IS antimicrobial activity against MRSA compared to a 10% phenol standard and to Manuka honey. Formulation A³IS is at normal pH 5.5 (test material A) and pH 7 (test material B), a negative control A³IS containing no GOX is included. The results demonstrate significant in vitro anti-MRSA efficacy and the superiority of A³IS over Manuka honey and a 10% phenol gel control;

FIG. 11b shows the A³IS antimicrobial activity against clinical isolates of Mastitis compared to Antibiotics. A³IS inhibition assay (3 day repeats) compared to four antibiotics (Vancomycin, Streptomycin, Tetracycline and Chloramphenicol) when tested against 22 clinical isolates of Mastitis causing *Staphylococcus aureus* organisms. A³IS demonstrates superior in vitro efficacy to all of these antibiotics. Clinical isolate number 15 is resistant to Vancomycin, Streptomycin and Tetracycline and shows only mild sensitivity to Chloramphenicol, however, it demonstrates sensitivity to A³IS;

FIG. 11c shows the A³IS antimicrobial activity against clinical isolates of Mastitis compared to commercially available anti Mastitis products. A³IS inhibition assay (3 day repeats) compared to four of the leading commercially available anti mastitis multi antibiotic products when tested against 22 clinical isolates of Mastitis causing *Staphylococcus aureus* organisms. Formulation A³IS demonstrates comparable in vitro efficacy compared to three of the leading commercial products and is superior to one of these products;

FIG. 11d shows the A³IS antimicrobial activity against clinical isolates of Mastitis compared to a 2% Nisin Solution. A³IS inhibition assay (3 day repeats) compared to a 2% Nisin solution on 21 clinical isolates of Mastitis causing *Staphylococcus aureus* organisms. Formulation A³IS demonstrates superior in vitro efficacy to the 2% Nisin solution. Note: Clinical isolate number 15 of FIG. 11b was unrecoverable from storage and is not included in this assay;

FIG. 11e shows the development of Nisin Resistance. A 2% Nisin resistant colony (indicated by the arrow) within the zone of inhibition during a Nisin efficacy study. A³IS resistant colonies have never been observed;

FIG. 12a shows A³IS MTT toxicity assessment on NHFs (Normal Human Fibroblasts. Included in the assay are a 50% concentration of A³IS, a range of concentrations of commercial silver containing gel and a commercial zinc containing gel product, compared to sodium azide (positive control). A³IS demonstrates less toxicity than either the commercial silver containing gel or the commercial zinc containing gel product;

FIG. 12b shows A³IS MTT toxicity assessment on NHKs (Normal Human Keratinocytes). Included in the assay are a 50% concentration of A³IS, a range of concentrations of a commercial silver containing gel and a commercial zinc containing gel product, compared to sodium azide (positive control). A³IS demonstrates less toxicity than either the commercial silver containing gel or the commercial zinc containing gel product;

FIG. 12c shows A³IS agar overlay cytotoxicity assessment on L929 cells. Included in the assay are a 50% concentration of A³IS, a range of concentrations of a commercial silver containing gel and a commercial zinc containing gel product, compared to sodium azide (positive control). A³IS demonstrates less toxicity than either the commercial silver containing gel or the commercial zinc containing gel product;

Figure 13A:
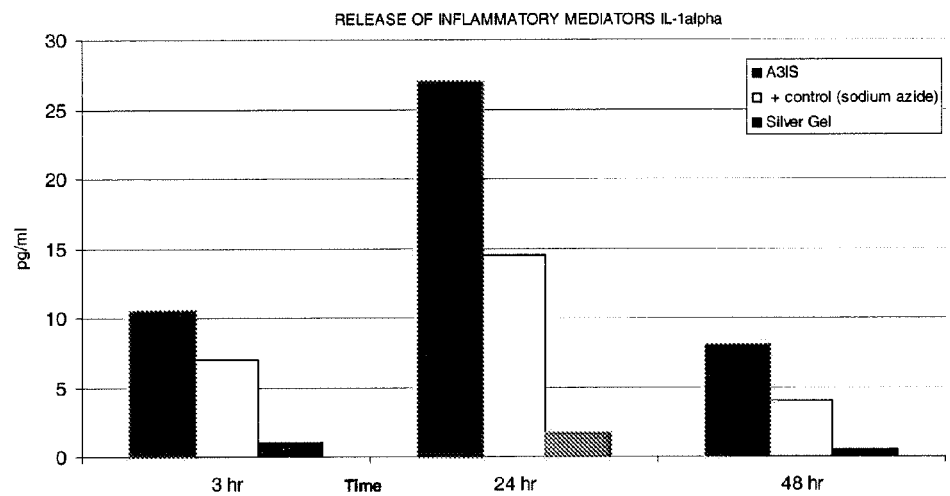
Figure 13B:
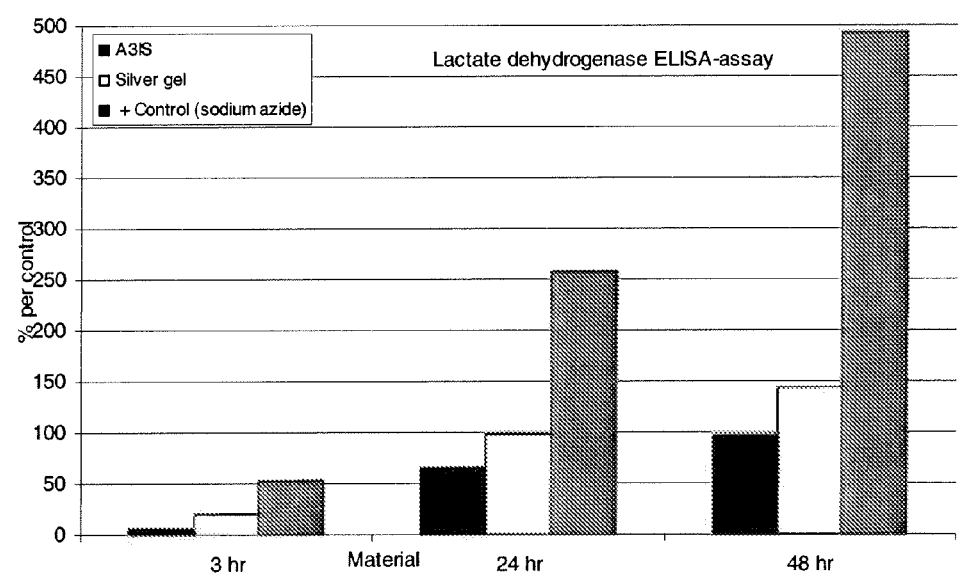
Figure 14:
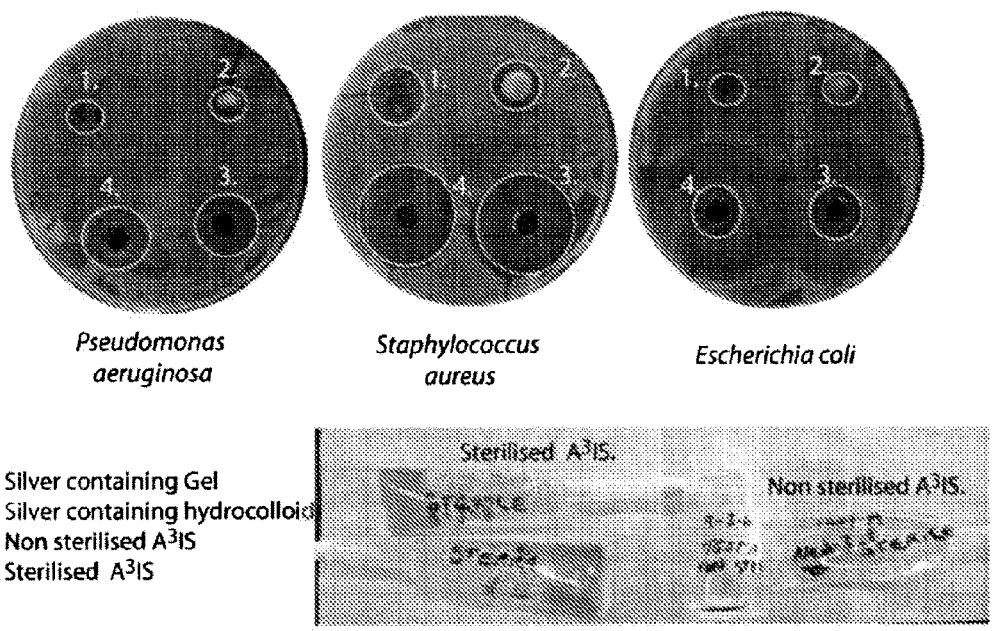
Figure 15A:
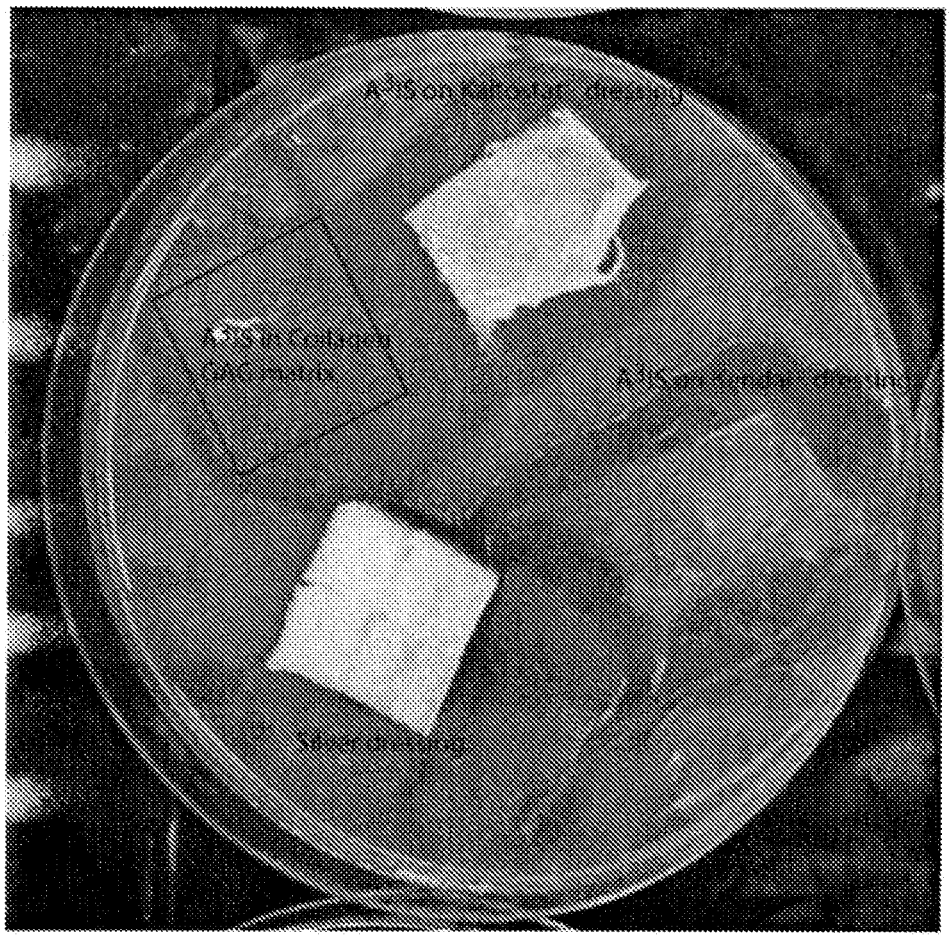
Figure 15B:
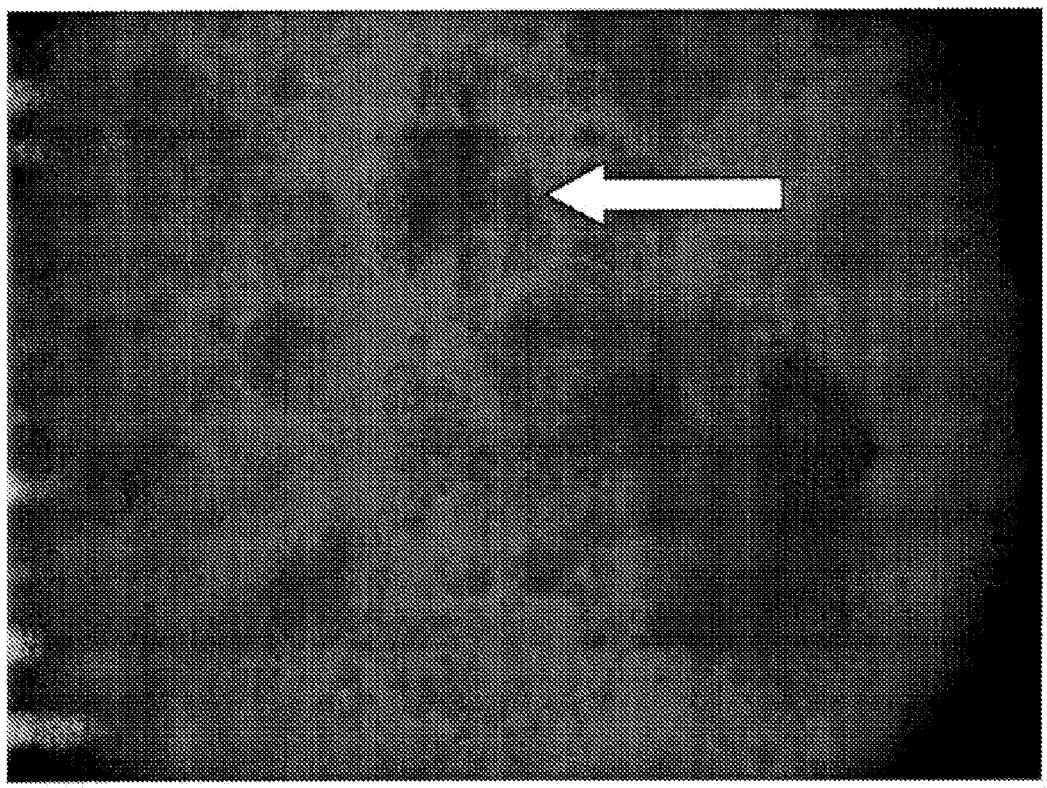
Figure 15C:
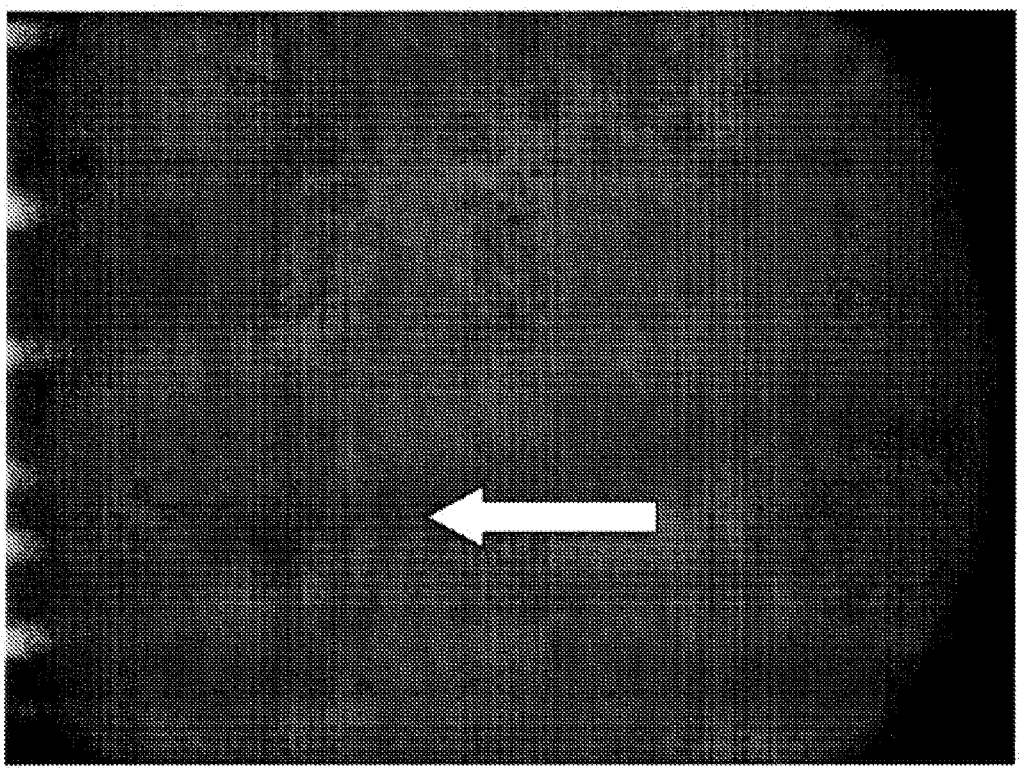

FIG. 13a shows induction of IL-1 release by A³IS. ELISA assay of the supernatant from a 3D irritancy assay over a 48 hour period, measuring and comparing the release of IL-1 when exposed to A³IS formulation, to a sodium azide positive control, and a commercial silver containing gel product. The results indicate that IL-1 is released from the skin cells exposed to the A³IS formulation;

FIG. 13b shows the induction of LDH release by A³IS. ELISA assay of the supernatant from a 3D irritancy assay over a 48 hour period, measuring and comparing the release of Lactate Dehydrogenase (LDH) when exposed to A³IS, a sodium azide positive control, and a commercially available silver containing gel product. Lactate dehydrogenase is released by cells exposed to destructive compounds. The results indicate that the A³IS formulation is less toxic than commercially available silver containing gel products;

FIG. 14 shows A³IS before and after sterilisation by Gamma irradiation. Gamma irradiation does not reduce activity as shown by zone of inhibition assays on *S. aureus, E. coli* and *Pseudomonas aeruginosa*;

FIG. 15a shows A³IS in a Collagen-GAG matrix and in commercial wound dressings tested for antibacterial activity against *S. aureus*. A³IS demonstrates antibacterial activity which is superior to that observed with a commercially available silver dressing used as a control;

FIGS. 15b and 15c show collagen-GAG matrix infiltration by NHFs. Infiltration by NHFs of the Collagen-GAG matrices. Over a 4 day period following addition of test sections NHFs are observed to attach to and grow within and along the Collagen-GAG matrices as indicated by the arrow.

Figure 16A:
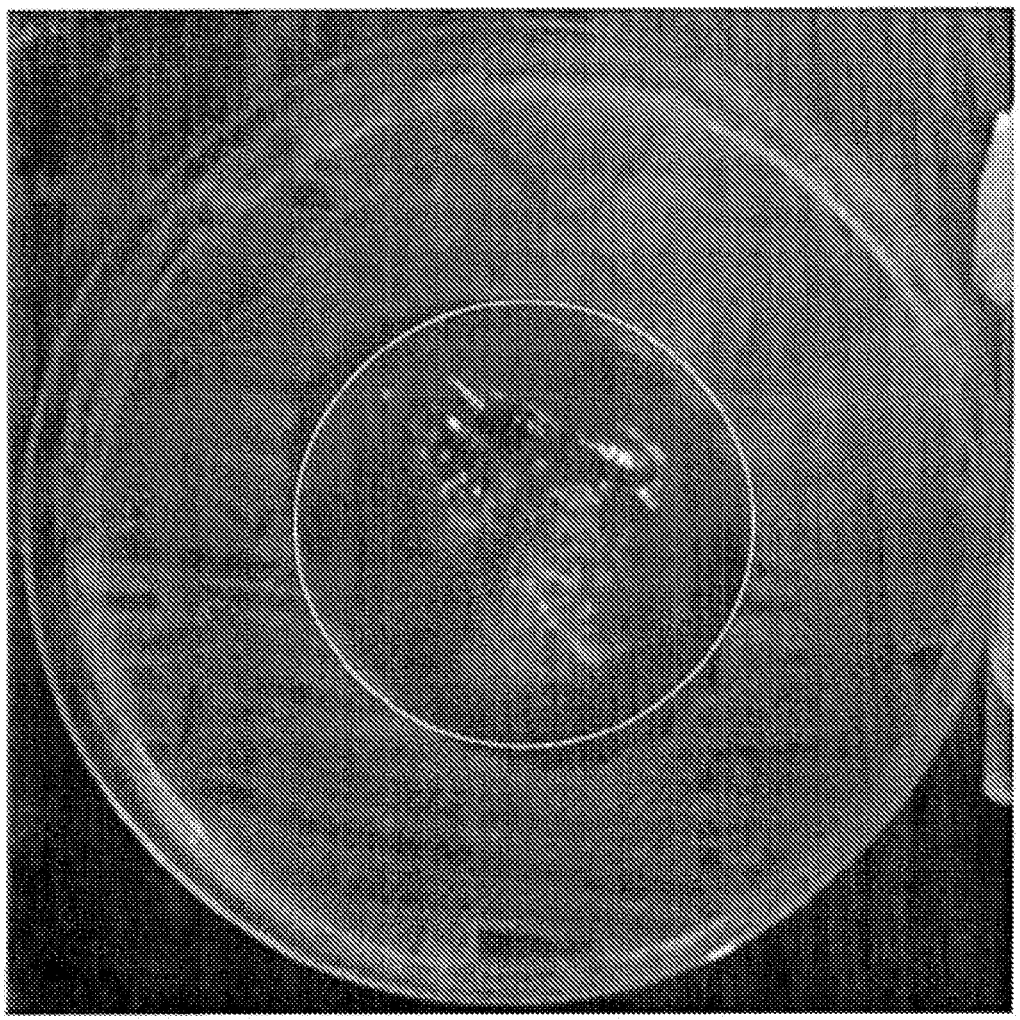
Figure 16B:
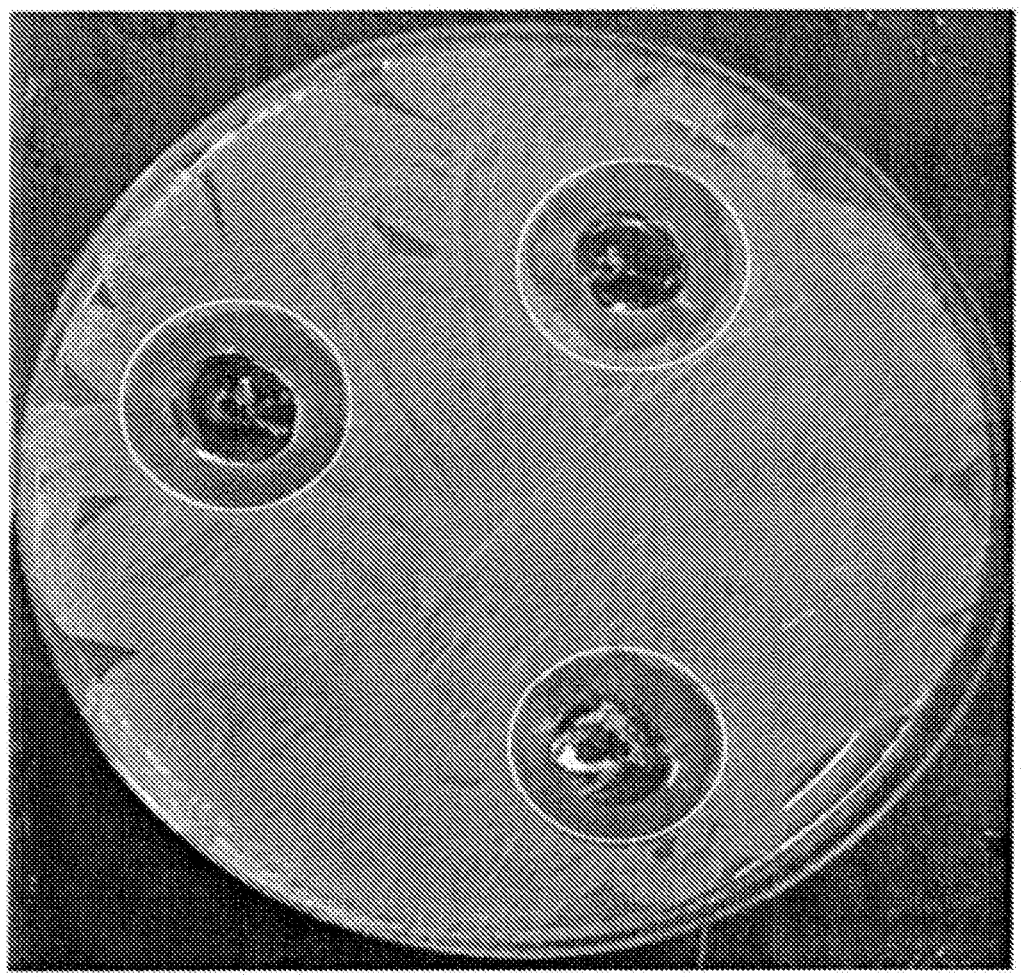
Figure 17:
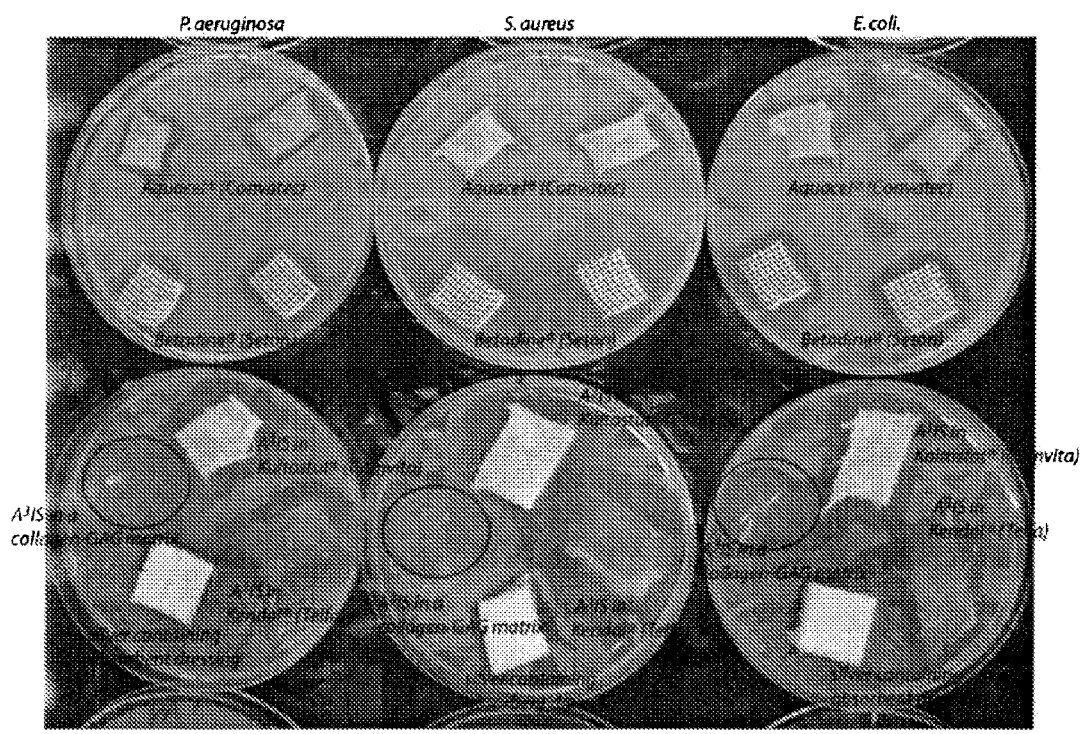
Figure 18A:
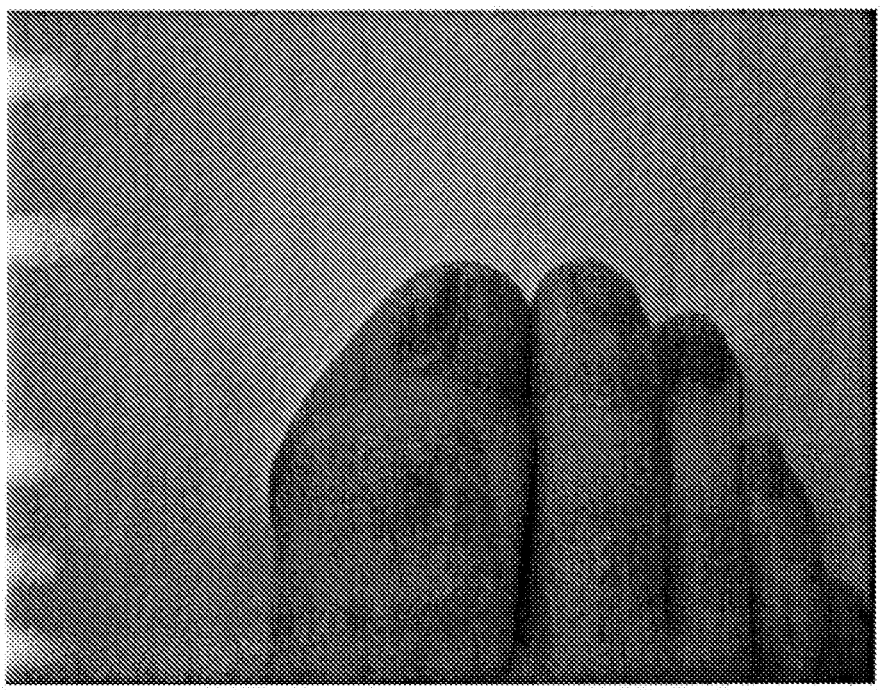
Figure 18B:
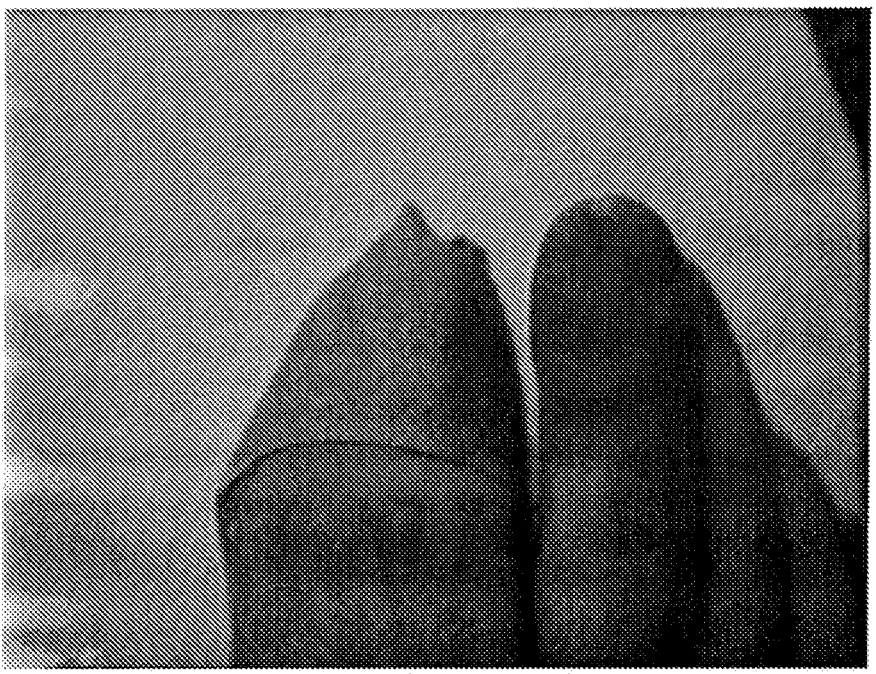
Figure 18C:
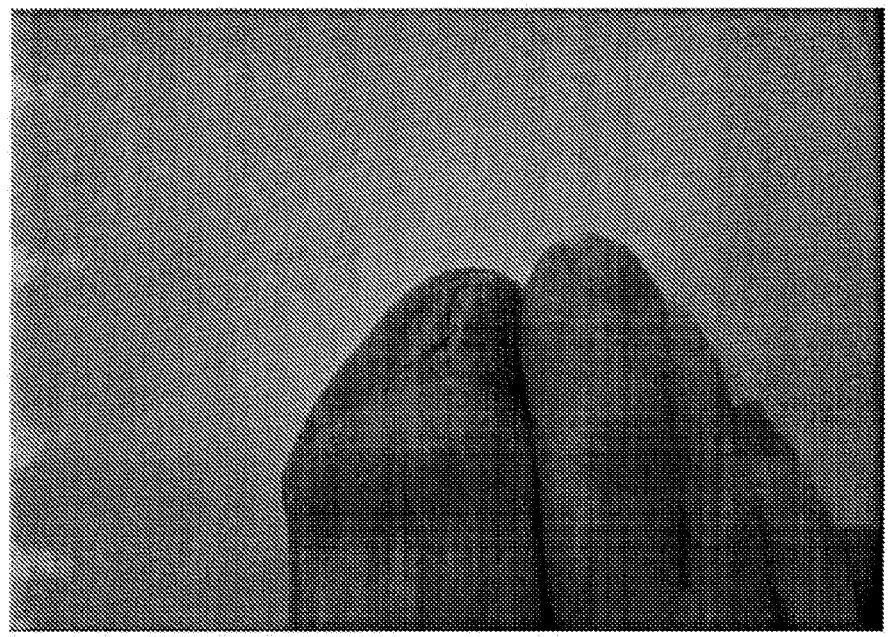
Figure 18D:
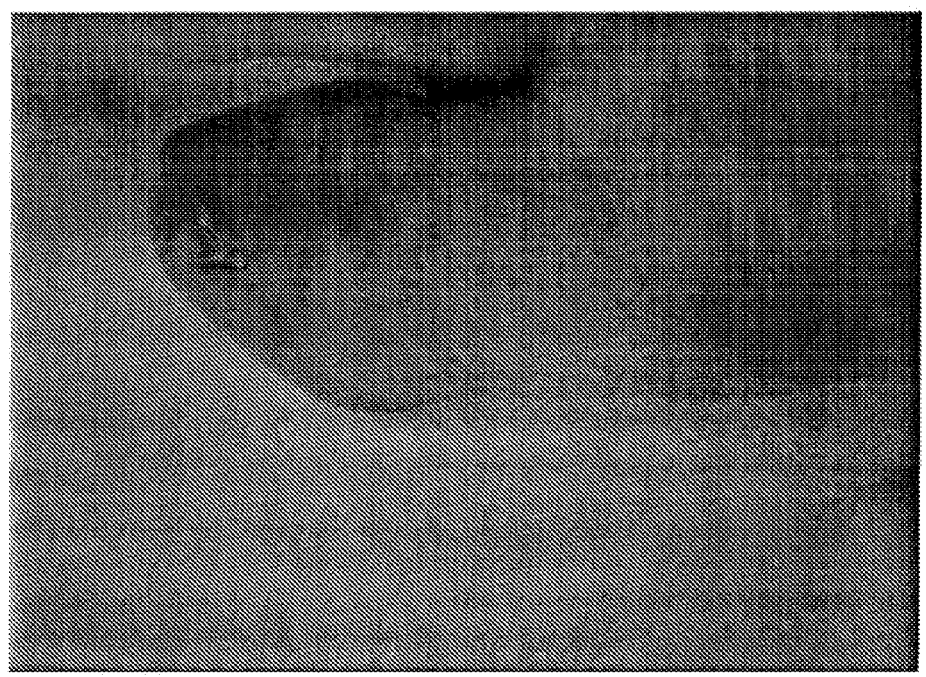

FIG. 16a shows A³IS in an alcoholic gel tested using the surface diffusion bio assay to determine zones of inhibition against *S. aureus*. Zones of inhibition are small due to the absorptive property of the gel matrix, but there is a clear zone around the gel matrix;

FIG. 16b shows A³IS—stability in an alcoholic gel. The A³IS in an alcoholic gel formulation was put on a short term stability study of 6 weeks, including a freeze thaw cycle and tested using the surface diffusion bio assay to determine zones of inhibition against *S. aureus*. Results indicated that the gel formulation maintained stability throughout the test period;

FIG. 17 shows a comparative investigation of A³IS efficacy. A³IS was poured onto the surface of a range of commercially available dressings Kaltostat® (Comvita), Kendal® (Telfa) and a Collagen-GAG (glycosaminoglycan) matrix as previously described and allowed to diffuse into the dressing for several hours. Sections were cut and placed onto agar plates, previously inoculated with *S. aureus, E. coli* and *P. aeruginosa*. The antibacterial efficacy of A³IS impregnated dressings was then compared to Aquacel® (Convatec) and Betadine® (Seton) commercially available dressings that contain elemental silver and iodine. A³IS dressings are as effective antimicrobially as Aquacel® (Convatec) and Betadine® (Seton) and a commercially available dressing that use elemental silver and iodine;

FIG. 18a shows A³IS—antimicrobial activity against Onychomycosis. Onychomycosis present in a toenail prior to treatment with A³IS;

FIG. 18b shows A³IS—antimicrobial activity against Onychomycosis. A³IS covered with a bandage whose wadding is moistened using water. The nail is therefore covered in an occlusive dressing;

FIG. 18c shows A³IS—antimicrobial activity against Onychomycosis. Photograph 48 hours after initiation of A³IS treatment. It is evident that the nail has changed appearance in that it is now darker in colour; and FIG. 18d shows A³IS—antimicrobial activity against Onychomycosis. Photograph 8 weeks after initiation of A³IS treatment. In this the band of uninfected nail is clearly visible, indicating that the dermatophytes have been eliminated.

Figure 19:
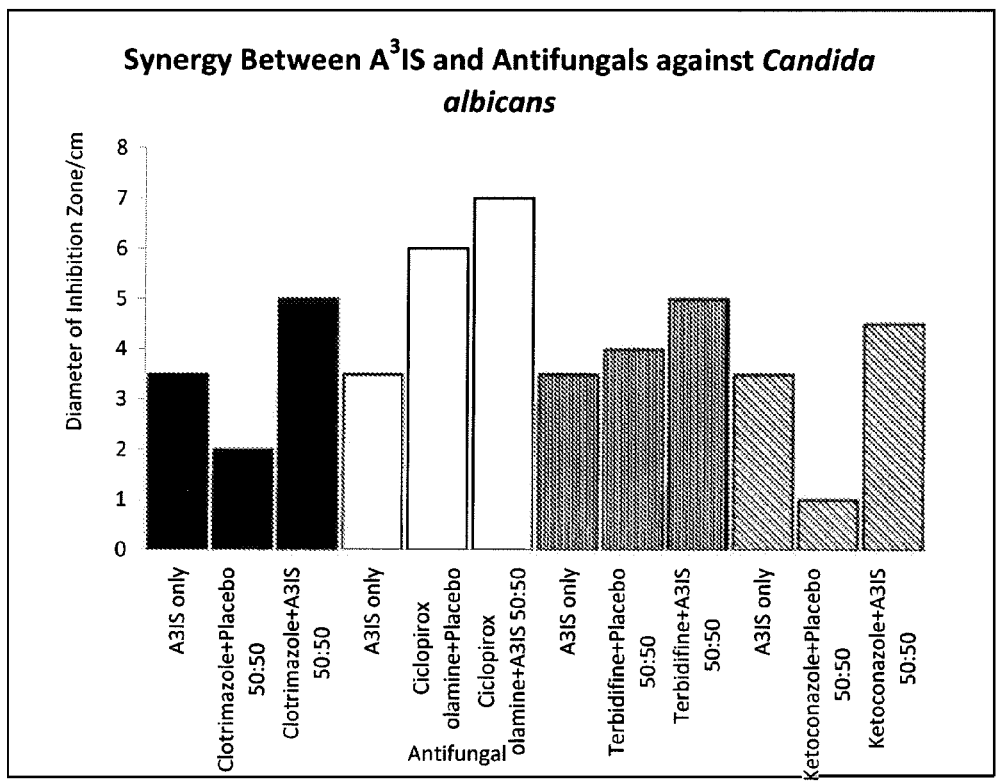

FIG. 19 shows the results of an inhibition assay using (a) A³IS only, (b) a combination of a placebo (A³IS containing no GOX) and an antifungal agent, and (c) a combination of A³IS and an antifungal agent tested against *Candida albicans*.

EXAMPLES

General Materials and Methods

Manuka Honey:
Manuka Care 18+® (Comvita) or Medihoney® was prepared as a 50% v/v in nutrient broth. 11 serial 1 in 2 dilutions of the 50% v/v preparation were made in nutrient broth and used for microbial inhibition testing, giving a lowest concentration of 0.01%.

Sugars:
(D+) glucose, D (−) fructose, (D+) maltose and (D+) sucrose (Sigma Aldrich)

Glucose Oxidase
0.5% glucose oxidase powder (5600 U/100 g) was used in the manufacture of A³IS.
Glucose Oxidase 240 U/mg (Biozyme UK) (1 U is that amount of enzyme causing the oxidation of one micromole of glucose per minute at 25° C. and pH 7.0) and Glucose Oxidase 100 U/mg to 250 U/mg (Sigma Aldrich) (1 U will oxidize 1.0 mole of D-glucose to D-gluconolactone and $H_2O_2$ per min at pH 5.1 at 35° C.) were also used in the following Examples.

pH Adjustment:
A 50% v/v solution of Manuka honey was pH adjusted to pH6.5 with 1M NaOH and a sample of the sugar mix without glucose oxidase was pH adjusted to pH 3.8 with 1M HCl. pH was measured with a pH meter (Hanna Instruments HI 931410).

Simile Sugar Preparations:

50% w/v solutions of glucose only, fructose only, and sucrose only were prepared and serially diluted in a similar manner to the Manuka honey.

Measurement of Moisture Content and Available Water (Aw):

Determination of moisture content was made using a Carl Fisher Titration apparatus (Switzerland). Determination of Aw was made using an Aqua Lab Aw meter, model series 3TE, Decagon Devices Inc. Pullman, Wash., (Kind permission Glanbia Innovation Centre, Kilkenny).

$H_2O_2$ Assay:

Hydrogen peroxide was determined following the method of (Kerkvliet 1996 and Serrano et al., 2004), using Merckoquant test strip (no. 10011; Merck, Germany).

Removal of $H_2O_2$:

Catalase (Sigma Chemical Co., from bovine liver, cat. No. C-30. 12,800 U/mg) was added to normal pH Manuka honey dilutions (initial pH 4) and to pH adjusted Manuka honey dilutions (initial pH 6.8) at the same concentrations used by Taormina et. al., Allen et. al., and Molan et. al. 1988). Typically the concentration added is 100 times greater than the measured amount of $H_2O_2$ present.

Heat Treatment of Manuka Honey:

A 50% solution of Manuka honey in nutrient broth was heat treated to a temperature of 85+/−5° C. in a water bath, this temperature was maintained for a period of 60 minutes or 120 minutes. A 50% solution of Manuka honey in nutrient broth was autoclaved at 121 psi for 15 minutes. From these heat treated honey preparations dilutions were prepared for assay.

Microbial Strains:

*Escherichia coli* (NCIMB 8545), *Staphylococcus aureus* (NCIMB 9518) and *Pseudomonas aeruginosa* (NCIMB 8626) are grown on nutrient agar or in nutrient broth for 24 hrs at 37° C.

*Candida albicans* (NCIMB 3179) and *Saccharomyces cerevisiae* are grown on sabaroud dextrose agar or in sabaroud dextrose broth for 24 hrs at 37° C.

*Propionibacterium acnes* (*P. acnes* ATCC/NTC 11827) is grown anaerobically on blood agar or in nutrient broth for 72 hrs at 37° C.

22 isolates of *Staphylococcus aureus* from clinical mastitis obtained from Sligo regional Veterinary Laboratories are grown on nutrient agar or in nutrient broth for 24 hrs at 37° C.

For testing conducted in the Sligo Regional General Hospital; five Beta haemolytic Streptococci Group A clinical isolates are grown on blood agar or in nutrient broth for 24 hrs at 37° C.

*Campylobacter coli* (NCTC 11366) is grown on brain heart infusion agar or in brain heart infusion broth for 72 hrs at 37° C.

*Campylobacter jejuni* (NCTC 11322) and three clinical isolates are grown on brain heart infusion agar or in brain heart infusion broth for 72 hrs at 37° C.

MRSA (ATCC 43300) and seven clinical isolates are grown on nutrient agar or in brain heart infusion broth for 72 hrs at 37° C.

Laboratory mould isolates are grown on sabaroud dextrose agar or in sabaroud dextrose broth for 48 hrs at 25° C.

*Botrytis cinerea* is grown on sabaroud dextrose agar or in sabaroud dextrose broth for 48 hrs at 25° C.

Bacterial growth is monitored by measuring the culture optical density (OD) in a spectrophotometer (Anthos 2010) at a wavelength of 620 nm.

Well/Disc Diffusion Methods—for Measurement of Microbial Inhibition

Agar plates are inoculated by swabbing overnight culture onto the plate surface. Plates are allowed to stand at room temperature for 15 minutes before use. Wells 8.2 mm diameter are bored into the surface of the agar. One hundred and eighty μl of sample is placed into each well. The samples diffuse into the agar around the well and are assayed for an ability to produce a zone of inhibition. Plates are incubated for 24, 48 or 72 hrs and zones of inhibition are measured using an Autodata automatic zone reader. The diameter of zones, including the diameter of the well (8.2 mm), is recorded.

For disc assays, sterile absorbent discs (8.2 mm diameter) are placed into sample dilutions for 10 minutes before being applied directly to inoculated agar plates. The samples diffuse from the disc into the agar and are assayed for an ability to produce a zone of inhibition. Plates are incubated for 24, 48 or 72 hrs and zones of inhibition are measured using an Autodata automatic zone reader. The diameter of zones, including the diameter of the disc (8.2 mm), is recorded.

Honey Bactericidal Quantifications

The agar diffusion assay (ADA) is generally the preferred method for honey bactericidal quantifications and determining biological potency for compounds/actives—antibiotics, and is used for Manuka honey production batch analysis and release procedures (Gribbles Analytical Laboratories Kerkvliet, J. D., 1996. Screening method for the determination of peroxide accumulation in honey and relation with UMF content (*Journal of Apiculture Research.* 35, 3, pp. 110-117). However, the subjective nature of this assay limits the interpretation of results. It is also time consuming and laborious, requiring preparation and cooling of plates, boring of test wells in agar and manual measuring of inhibition zones after 24 hrs of incubation. The quality of results depend largely on technique and judgment, and the suggested precision cannot be obtained when the inhibition zone is unclear or not perfectly circular.

Other Methods—for Measurement of Microbial Inhibition

Microbial growth, or inhibition of growth, can be detected using a variety of biological methods, including, direct microscopic counts, absorbance, bioluminescence, assays that incorporate a colorimetric, and fluorometric growth indicator, turbidity, dry weight and zones of inhibition.

Spectrophotometric Assay

We developed a spectrophotometric assay using 96 well microtiter plates (Patton T. et al Journal of Microbiological Methods (2006) pages 84-95) and compared this method to the standard methods of well/disc diffusion in order to evaluate the potential advantages of this bioassay for evaluation of the antibacterial properties of Manuka honey. Increased automation and throughput (efficiency) were achieved using the spectrophotometric assay which can rapidly generate large amounts of data making possible a detailed statistical analysis of results. The method is more sensitive, and more amenable to statistical analysis than the assays currently employed, permitting extensive kinetic studies even in the presence of low honey concentrations (Table 1). The assay is capable of detecting inhibitory levels below that recorded for well or disc diffusion assays. This assay provides a quick and sensitive method for elucidating the activity of Manuka honey.

TABLE 1

| Microbial species | Disc Assay MIC50 | Well Assay MIC50 | Spectrophotometric Assay MIC50 |
|---|---|---|---|
| Escherichia coli | 22.4% | 24.5% | 5.6% |
| Staphylococcus aureus | 25.7% | 22.6% | 0.78% |
| Bacillus cereus | 24% | 21.9% | 2.00% |
| Candida albicans | No inhibition | No inhibition | 40% |

MIC50 values indicate percent Manuka honey present resulting in a 50% inhibition in growth of a test micro-organism.

Honey dilutions are inoculated with a 5% v/v of overnight test culture. Two hundred microliters of each dilution, using 8 replicates per dilution, are applied to wells of a flat bottom 96 well microtiter plates with lid to prevent cross contamination (Costar, Corning Ltd. NY). Control wells received 200 microliters of 5% culture inoculated broth. Optical density is determined in a spectrophotometer at 620 nm prior to incubation, ($T_0$). Plates are incubated for 24 hrs in the dark on a Certomat MO orbital shaker at 100 rpm to prevent adherence and clumping. After 24 hrs plates are again read in a spectrophotometer at 620 nm, ($T_{24}$). Results shown are averages from eight determinations repeated five times on three separate days.

The OD for each replicate at $T_0$ is subtracted from the OD for each replicate at $T_{24}$. The adjusted OD of each control well is then assigned a value of 100% growth. The growth inhibition for the test wells at each dilution is determined using the formula:

Percent Inhibition=1−(OD test well/OD of corresponding control well)×100 for each row of the 96 well plate e.g. OD row 1, column 1, well 1 (test) is divided by the OD value of Row 1, column 12, well 12 (control).

This yield eight replicate inhibition values for each honey dilution. All assays are repeated a minimum of three times on three different days using a minimum of three plates per test, i.e. each data point reported is an average from a minimum of 72 point determinations.

The standard deviation associated with the average calculated inhibition values for replicate wells is determined and is plotted as associated error bars for each data point on graphs. Where the resulting measurement recorded a negative inhibition value (growth promotion) this is reported as stimulation using the formula:

Percent Growth=(OD test/OD control)×100.

Example 1

Figure 1A:
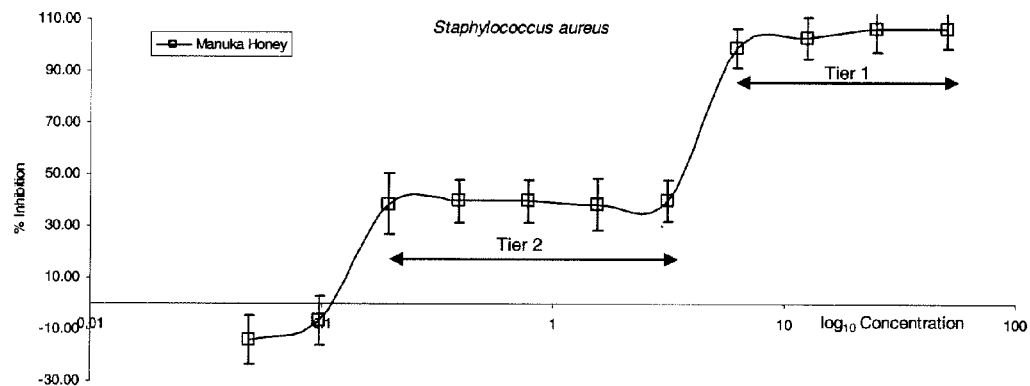

Characterisation of Antimicrobial Activities in Manuka Honey—Absence of Endogenous Hydrogen Peroxide Using the Spectrophotometric bioassay described, antimicrobial activity of commercially available Manuka honey is determined, using several samples to ensure consistency. Results shown in FIG. 1a demonstrate that Manuka honey provides a first tier of microbial inhibition activity at dilutions 50% to approximately 6.25% and a second tier of microbial inhibition activity at dilutions 3.125% to approximately 0.195%

This two tier effect is shown to be produced by separate mechanisms. Initial microbial inhibition on low honey dilution (50%-6.25%) results from a combination of low pH and growth limiting Aw (Available Water) and a very minor role by hydrogen peroxide, which is only produced de-novo upon dilution and after a considerable period of time has elapsed. There is no detectable endogenous hydrogen peroxide present in diluted or undiluted Manuka honey, as shown in Table 2

TABLE 2

Manuka honey $H_2O_2$ generation profile

| | % Dilution | | | |
|---|---|---|---|---|
| | 50.00 | 25.00 | 12.50 | 6.25 |
| Manuka honey | pH 3.89 | pH 4.35 | pH 4.96 | pH 5.95 |
| $H_2O_2$ mg/L (Time 0 hrs) | 0 | 0 | 0 | 0 |
| Manuka honey | pH 3.89 | pH 4.35 | pH 4.96 | pH 5.95 |
| $H_2O_2$ mg/L (Time 3 hrs) | 0 | 35 | 35 | 65 |

As the concentration of the honey is diluted, and after a period of time has elapsed, hydrogen peroxide is produced and further contributes to the antimicrobial effect.

Figure 1B:
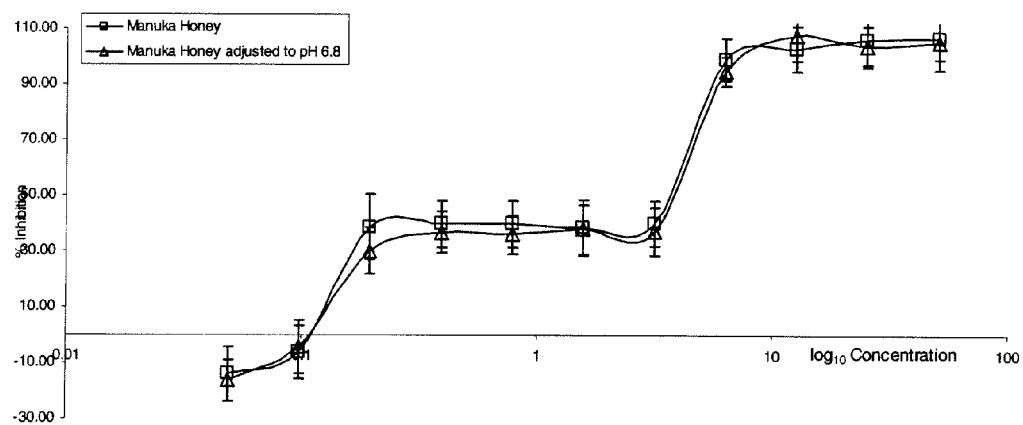
Figure 1C:
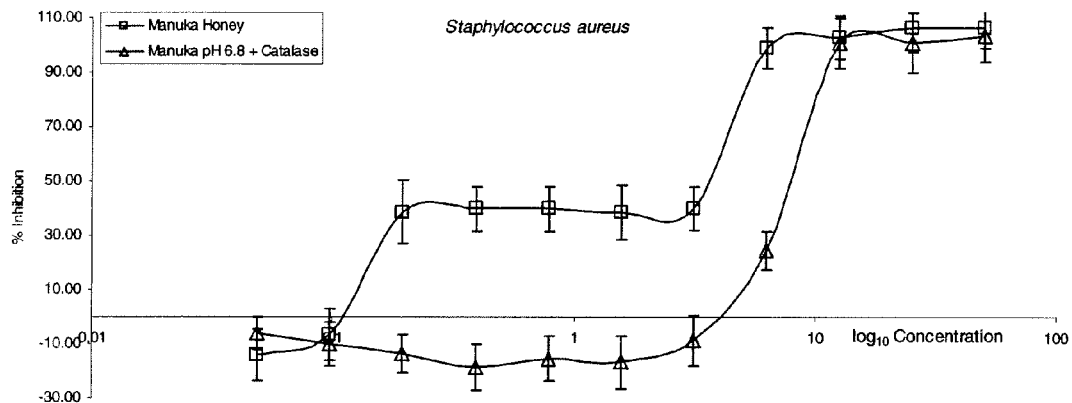

Adjusting the pH of Manuka honey from its natural pH of approximately 4.0 to a near neutral pH of 7.0 does not significantly affect the antimicrobial profile FIG. 1b. When Manuka honey dilutions are pH adjusted to near neutral followed by the addition of catalase in excess, the antimicrobial profile of the honey is altered FIG. 1c. The first tier of antimicrobial inhibition is only slighted affected but the second tier is significantly affected indicating that the antibacterial effect in the second tier is primarily the result of hydrogen peroxide liberation.

The belief that a non peroxide activity also referred to as Unique Manuka Factor (UMF) exists is due to an experimental procedural oversight. Specifically, the failure by other research groups to neutralise the pH of Manuka honey prior to catalase addition essentially renders the added catalase ineffective as the honey pH is too acidic for catalase activity. As honey to which excess catalase has been added still retains antimicrobial activity the belief that a UMF exists has persisted. As FIG. 1b shows, adjusting the pH of Manuka honey to pH 6.80 does not affect the antimicrobial activity. A pH of 6.80 is close to the optimum pH for catalase activity and under this condition the added catalase does neutralise the hydrogen peroxide activity thereby altering the antimicrobial activity profile of the honey.

Surprisingly, we also found that this glucose oxidase pathway is not operational immediately on application of Manuka honey and is only operational following dilution of the honey and after a period of time has elapsed.

Example 2

A Prototype Antimicrobial Endogenous and Sustained Release Hydrogen Peroxide Generating System A prototype formulation containing 31+/−5 g glucose: 35+/−5 g fructose: 7+/−2 g maltose: 1.5+/−1 g sucrose is made by mixing the ingredients, making the mixture up to a final volume of 100 ml in distilled deionized (DI) water; the mixture is sterilized by autoclaving. Glucose oxidase at 0.05% by weight, which is a similar concentration to that contained in Manuka honey, is added.

Figure 2:
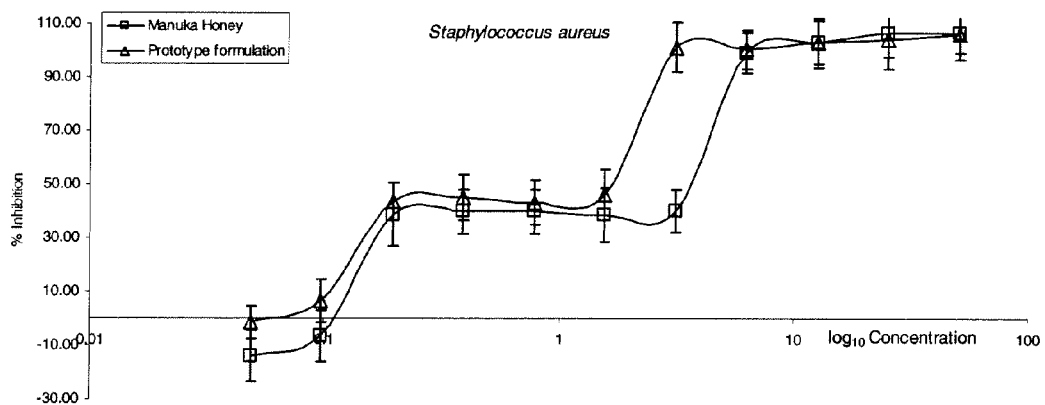

FIG. 2 shows the results of an antimicrobial assay on *S. aureus* using this prototype formulation. The prototype formulation of this example demonstrated a greater activity compared to Manuka honey. It is probable that the critical role played by the glucose oxidase enzymatic pathway in the antibacterial effect is enhanced once free from impurities and reaction limiting compounds (such as catalase) present in honey. This prototype demonstrates very effective bactericidal activity.

Example 2.1

Figure 3A:
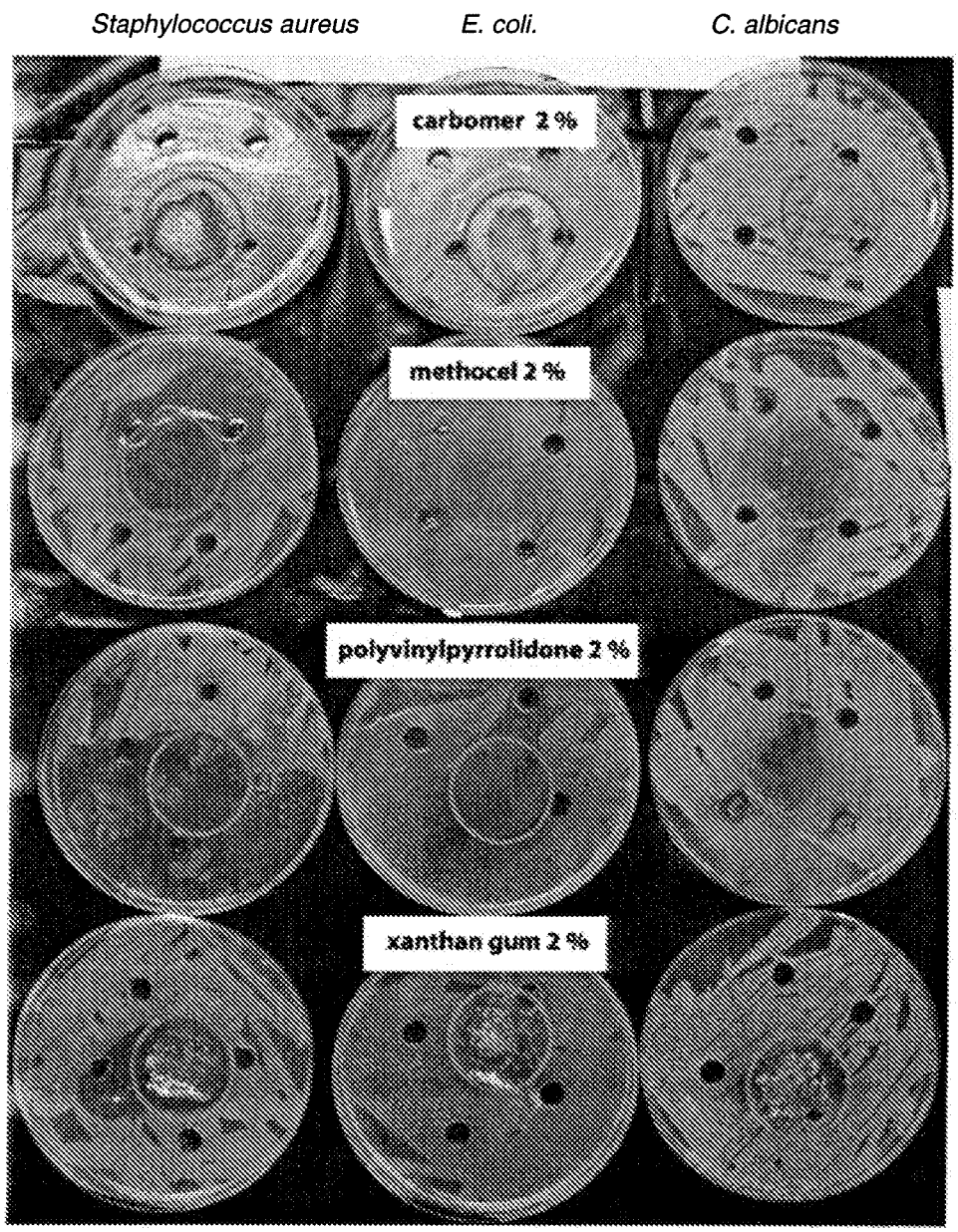
Figure 3B:
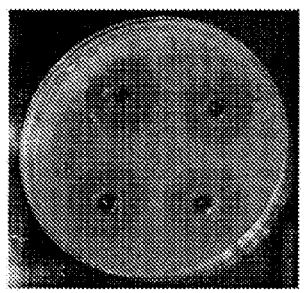

A gel Prototype Antimicrobial Endogenous and Sustained Release Hydrogen Peroxide Generating System Gelling agents that are common ingredients in topical pharmaceutical formulations are added to the prototype formulation and tested. Gels tested include water reconstituted cellulose and alcohol reconstituted cellulose agents (1. carbomer, 2. methocel, 3. polyvinylpyrrolidone and 4. xanthan gum at 2% in a hydrogel incorporating the prototype formulation). Both cellulose based gels demonstrate a decrease in stability. It is possible that steric hindrance and hydrolysis of the glucose oxidase result in loss of antibacterial activity. Even before loss of activity, due to decreased stability, neither gel formulations is as active as the prototype formulation, as evidenced by the smaller zones of inhibition in diffusion assays (compare FIG. 3a (gels) with FIG. 3b (prototype formulation)).

Example 2.2

Figure 4A:

A Prototype Antimicrobial Endogenous and Sustained Release Hydrogen Peroxide Generating System—Single Sugar & Enzyme Gel Formulation In an attempt to resolve the gel stability described in Example 2.1, formulations containing glucose and glucose oxidase only are made. Glucose formulations ranging from 30%-80% glucose in water are autoclaved or warmed slowly to boiling point to aid in dissolution of the sugar. During dissolution by boiling, various gelling agents are added and when cooled to below 40° C. 0.1% glucose oxidase is added. These formulations are tested for antibacterial activity (FIG. 4a).

Figure 4B:
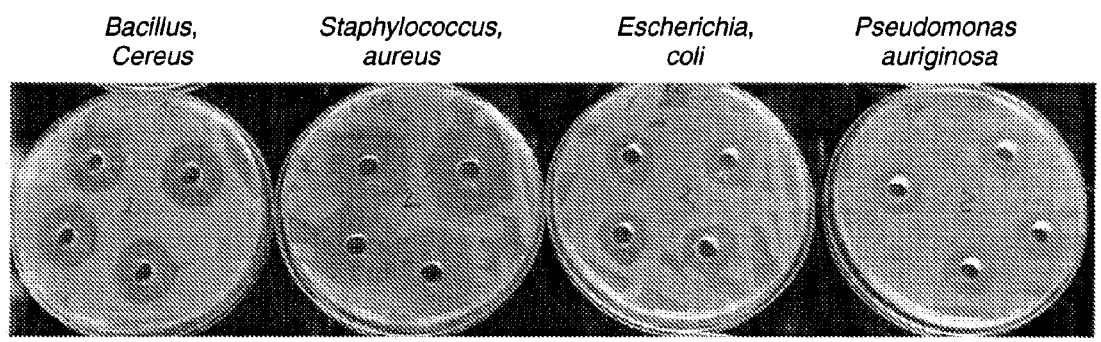

These formulations demonstrate only a limited degree of antibacterial activity and this activity is below that observed with the prototype antimicrobial formulation described in Example 2 as evidenced by the smaller zones of inhibition in Well/Disc diffusion assays (compare FIG. 4a (gels) with FIG. 4b (prototype)).

In addition to the reduced activity, the formulations containing the high glucose concentrations, when placed into aluminium tubes, solidify making the formulations unusable. The tubes containing formulations with lower concentrations of glucose demonstrate a lack of stability as evidenced by a decrease in antimicrobial activity over time.

Example 2.3

Improved Formulation Characteristics of Antimicrobial Endogenous and Sustained Release Hydrogen Peroxide Generating System—Varying the Carbohydrate and Water Concentration This example describes attempts to minimise the quantity of water present in formulations according to the invention, to minimise problems relating to stability as excess water may give rise to hydrolysis of the glucose oxidase. The formulations still require sufficient water to permit generation of $H_2O_2$, ease of application and to prevent precipitation of sugars during storage. Varying concentrations of sugars are mixed and heated as described in example 2.2 to determine the primary source for the precipitation and granular texture observed in earlier formulations. From this analysis, sugar concentrations are adjusted to reduce this effect. Following the addition of enzyme, suitable formulations are tested to determine antibacterial activity.

It is found that the concentration of water could be reduced from 20% to 10% which is the minimum concentration permitting enzyme activity, ease of application and prevention of sugar precipitation.

Uncontrolled heat treatment of sugars tends to produce carmelisation resulting in a formulation that acquires a yellow to brown colouration. To eliminate carmelisation, and thereby produce a clear material, a manufacturing process is developed in which the order of addition of sugars and their dissolution by heating is carefully selected to circumvent the carmelisation process. Glucose oxidase enzyme is added to this formulation and antibacterial activity, stability and suitability for application were assessed. These improvements to the Prototype formulation form the basis for all future formulations/systems described herein.

Example 3

Single Component Antimicrobial System, Having an Endogenous Hydrogen Peroxide Reservoir and Sustained Release A formulation for a single component antimicrobial system (hereafter referred to as 'Antimicrobial System' or $A^3IS$ or $A^3IS$ is made in accordance with Table 3.

TABLE 3

| Ingredient | Percentage by weight in Ex 3. | Preferred Percentage Range |
| --- | --- | --- |
| Purified water | 13.5 adjusted to make 100% | 10-20% |
| Glucose Powder | 38% +/− 10, preferably +/− 5 | 28-48% |
| Fructose Powder | 35% +/− 10, preferably +/− 5 | 25-45% |
| Maltose Powder | 10% +/− 5 | 5-15% |
| Sucrose Powder | 1.5% +/− 1 | 0.5-1.5% |
| Glucose Oxidase Powder | 0.5% enzyme (5600 U/g) pre-dissolved in 1.5% of purified water | at least 10U per 100 g of the system |
| TOTAL | 100% | 100% |

The pH of $A^3IS$ is set at pH 5.5. This low pH is within the glucose oxidase range of activity (pH 4.0-7.0 optimum pH of 5.5). If needed, a buffer can be added to obtain the desired pH, as illustrated in Table 4. The buffer is pre-dissolved in purified water and replaces part of the purified water from the formulation above.

TABLE 4

| Optional Buffering Ingredients for pH 5.5 | Percentage by weight |
| --- | --- |
| Citric Acid/Sodium Citrate | 0.918% pre-dissolved in 2% of purified water for pH 5.5 |
| Phosphoric Acid/Disodium hydrogen phosphate | 1.598% pre-dissolved in 2% of purified water for pH 5.5 |

It will be understood that different ratios of buffering ingredients can be used depending on the desired pH.

It will be understood that Prototype, described in Example 2 and A³IS described here give formulations suitable for use according to the invention. The subsequent Examples show analysis of various characteristics of A³IS.

The sugars described in Table 3 are added in the following sequence: fructose, glucose, maltose and sucrose. Each carbohydrate is dissolved fully in the water by heating to approximately 90° C. before the next carbohydrate is added. Alternatively the sugars can be prepared as above but under a vacuum at −0.5 Bar, which reduces the boiling point of the sugars to a temperature of less than 90° C. preventing discoloration.

When the carbohydrates are fully dissolved and clear, the mixture is allowed to cool to below 60° C. and optional buffering ingredients pre-dissolved in water are added to the main mixture.

When the base mixture is at a temperature below 40° C., a temperature which allows retention of enzyme activity, the glucose oxidase enzyme which is pre-dissolved in water is added and dispersed into the mixture. The mixture is allowed to cool to room temperature. When cool, the mixture is dispensed into aluminium tubes which are then sealed. Tubes are stored at room temperature.

Example 3.1

A Prototype Antimicrobial Endogenous and Sustained Release Hydrogen Peroxide Generating System—Varying the Enzyme Concentration and Type Honey is known to contain several enzymes in addition to glucose oxidase, including diastase and invertase. Diastase and invertase enzymes are incorporated into the prototype formulation of Example 2 to determine if they can enhance overall antibacterial activity by allowing for a slower but sustained release of $H_2O_2$ by acting on different carbohydrates in the formula.

We investigate several combinations and concentrations of enzyme to determine this potentially enhanced antibacterial activity. Diastase and invertase in differing combinations are added to the A³IS and compared to A³IS containing glucose oxidase only. We find no improvement in antibacterial activity in any of the formulations containing multi enzymes.

Figure 5A:
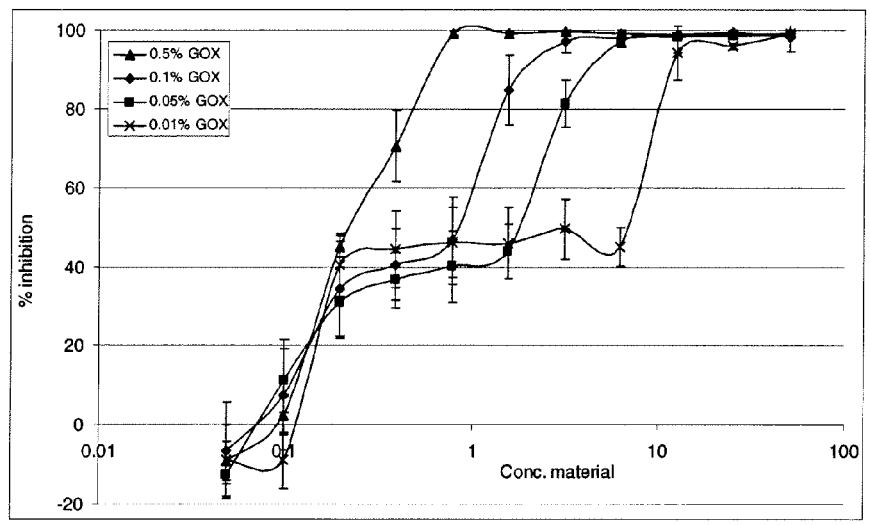

Different concentrations of glucose oxidase are also incorporated and compared by spectrophotometric assay to determine their quantity/activity relationship. The antibacterial activity of A³IS increases proportionally to the concentration of glucose oxidase. A substantial antibacterial effect is attained at an enzyme concentration of 0.05% (FIG. 5a).

This shows that a range of antibacterial activity can be achieved by varying the concentration of glucose oxidase. The enzyme can be dispersed with ease throughout the material during mixing.

Example 4

A³IS—an Innovative and Augmented Hydrogen Peroxide Generating System

Hydrogen peroxide is quantified following the method of (Kerkvliet 1996 and Serrano et al., 2004), using Merckoquant test strip (no. 10011; Merck, Germany). Results are expressed in milligrammes $H_2O_2$ per litre. The suitability of the method for hydrogen peroxide determination is verified by spiking freshly prepared Manuka honey dilutions with liquid $H_2O_2$ and verifying that the assay could accurately detect the quantity of $H_2O_2$ present.

Figure 5B:
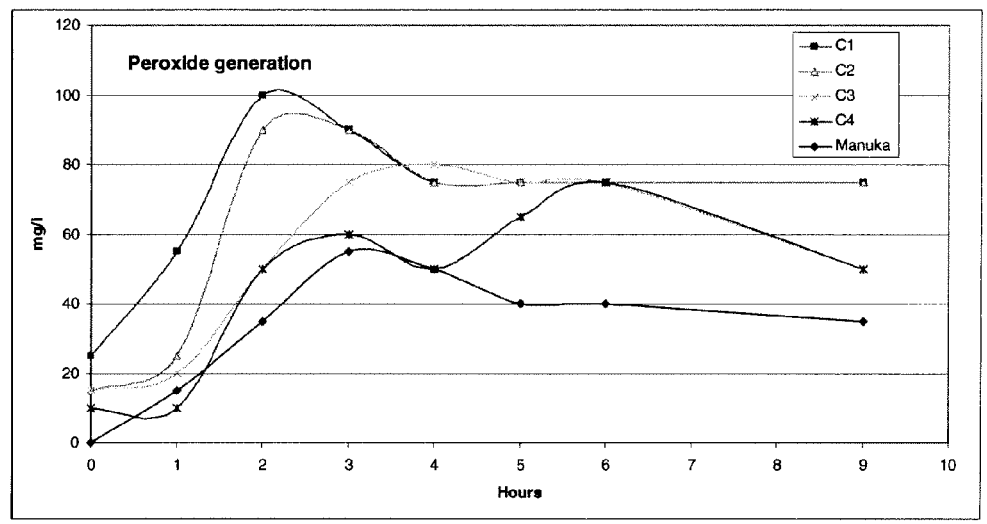

Table 5 and FIG. 5b show that A³IS, with 0.5% sigma Aldrich GOX enzyme 5600 U/g and diluted 50% (C1), 25% (C2), 12.5% (C3) or 6.25% in de-ionised water (DI) generate significantly increased levels of hydrogen peroxide compared with Manuka honey diluted at 50% in DI water.

TABLE 5

| Time hr. | Sample/mg H2O2/l | | | | |
|---|---|---|---|---|---|
| | C1 | C2 | C3 | C4 | Manuka |
| 0 | 25 | 15 | 15 | 10 | 0 |
| 1 | 55 | 25 | 20 | 10 | 15 |
| 2 | 100 | 90 | 50 | 50 | 35 |
| 3 | 90 | 90 | 75 | 60 | 55 |
| 4 | 75 | 75 | 80 | 50 | 50 |
| 5 | 75 | 75 | 75 | 65 | 40 |
| 6 | 75 | 75 | 75 | 75 | 40 |
| 9 | 75 | 75 | 50 | 50 | 35 |

Figure 5C:
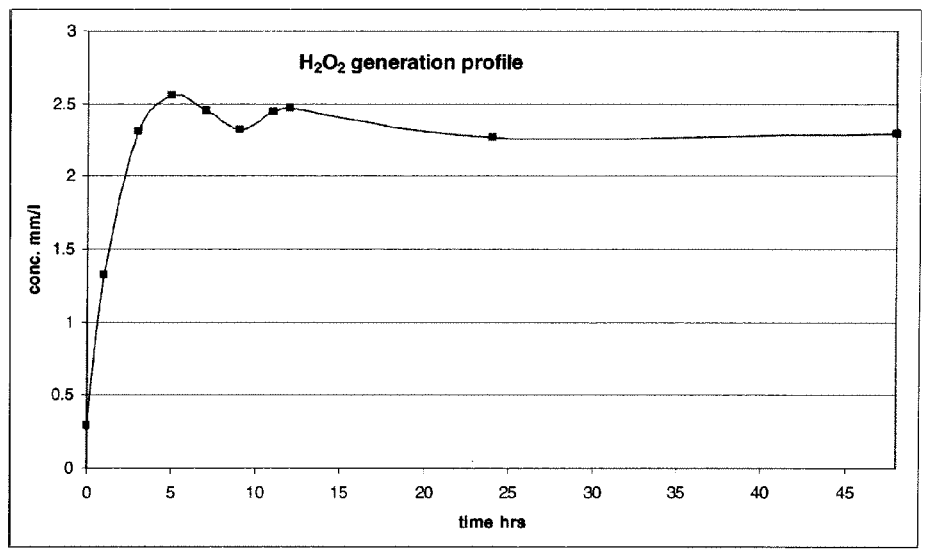

FIG. 5c shows this increased production of hydrogen peroxide (A³IS diluted 25% in DI water) is maintained for a period of at least 48 h.

Example 4.1

Figure 5D:
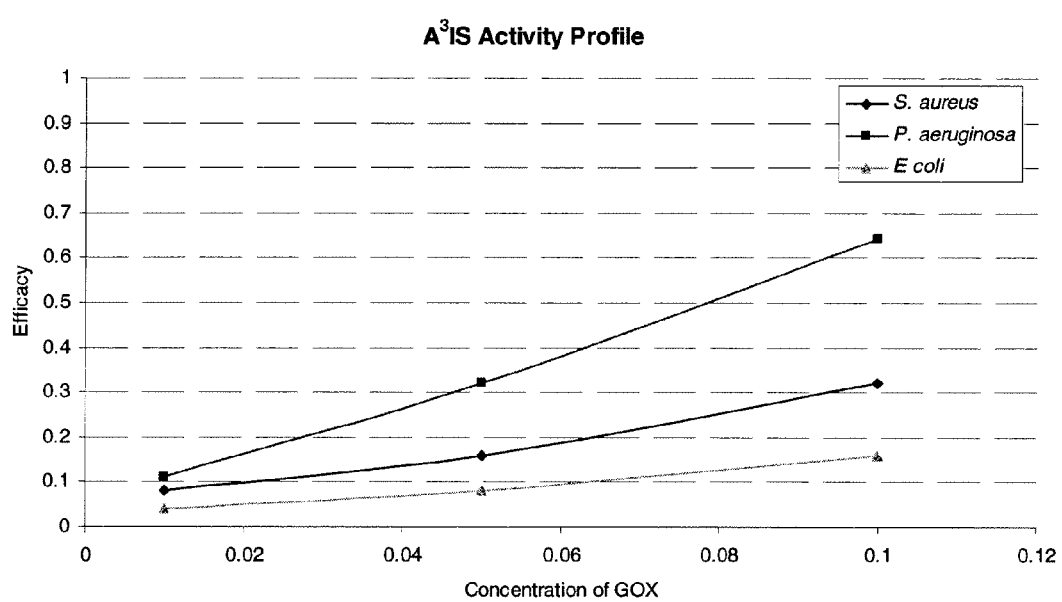

A³IS—Antimicrobial Activity Increased with Increased Glucose Oxidase Concentration FIG. 5d shows a dose response relationship between the concentration range of glucose oxidase and antimicrobial effect on S. aureus, as measured using a spectrophotometric inhibition bioassay.

FIG. 5d further demonstrates that it is possible to address the issue of potency/efficacy, as the formulations produced may be adjusted by variations of the concentration of glucose oxidase which is incorporated during manufacture, results shown on Staphylococcus aureus, Pseudomonas aeruginosa and Escherichia coli.

Example 5

A³IS—Endogenous Hydrogen Peroxide Reservoir

When A³IS is mixed with water within the dilution range 50% to 0.1% the liberation of hydrogen peroxide is detected immediately. Table 6 shows that up to 75 mg/L hydrogen peroxide is detected at T=0. This is in contrast to Manuka honey which fails to register any liberation of peroxide at time zero (See Example 1 Table 2) and demonstrates the presence of a significant endogenous reservoir of hydrogen peroxide generated during the formulation process.

Also, after three hours of incubation of diluted samples the amount of peroxide detected in A³IS significantly exceeds that detected in the natural honey, Table 6.

TABLE 6

| % Dilution | 50.00 | 25.00 | 12.50 | 6.25 | 3.13 | 1.56 | 0.78 | 0.39 | 0.20 | 0.10 | 0.05 | 0.025 |
|---|---|---|---|---|---|---|---|---|---|---|---|---|
| Manuka | | | | | | | | | | | | |
| Normal pH | 3.89 | 4.35 | 4.96 | 5.95 | 6.60 | 6.87 | 7.03 | 7.11 | 7.12 | 7.14 | 7.15 | 7.15 |
| Normal pH Aw | 0.908 | 0.970 | 0.985 | 0.994 | 0.994 | 0.995 | 0.996 | 0.996 | 0.996 | 0.996 | 0.996 | 0.997 |
| % water | 53.0 | 74.7 | 84.5 | 91.3 | N/A | N/A | N/A | N/A | N/A | N/A | N/A | N/A |
| $H_2O_2$ mg/L (T = 0 hours) | 0 | 0 | 0 | 0 | 0 | 0 | | | | | | |
| $H_2O_2$ mg/L (T = 3 hours) | 0 | 35 | 35 | 65 | 55 | 40 | 40 | 35 | 30 | 0 | 0 | 0 |
| Adjusted pH | 6.6 | 6.6 | 6.88 | 7.02 | 7.10 | 7.13 | 7.18 | 7.20 | 7.20 | 7.21 | 7.21 | 7.21 |
| Adjusted pH Aw | 0.906 | 0.966 | 0.983 | 0.990 | N/A | N/A | N/A | N/A | N/A | N/A | N/A | N/A |
| $A^3IS$ | | | | | | | | | | | | |
| Normal pH | 5.5 | 6.0 | 6.96 | 7.05 | 7.13 | 7.17 | 7.17 | 7.19 | 7.2 | 7.21 | 7.21 | 7.19 |
| Normal pH Aw | 0.906 | 0.964 | 0.983 | 0.990 | 0.995 | 0.996 | 0.997 | 0.997 | 0.997 | 0.997 | 0.997 | 0.997 |
| % water | 52.4 | 71.8 | 83.9 | 90.7 | N/A | N/A | N/A | N/A | N/A | N/A | N/A | N/A |
| $H_2O_2$ mg/L (T = 0 hours) | 75.0 | 75.0 | 75.0 | 75.0 | 70.0 | 60.0 | 55 | 55 | 45 | 5 | 0 | 0 |
| $H_2O_2$ mg/L (T = 3 hours) | 90 | 90 | 75 | 80 | — | — | — | — | — | — | — | — |
| Adjusted pH | 3.8 | 5.6 | 6.55 | 6.9 | 7.03 | 7.12 | 7.17 | 7.19 | 7.20 | 7.21 | 7.21 | 7.21 |
| Adjusted pH Aw | 0.904 | 0.964 | 0.982 | 0.991 | N/A | N/A | N/A | N/A | N/A | N/A | N/A | N/A |

This endogenous reservoir, shown here ranging between 10 and 75 mg/l hydrogen peroxide depending on the quantity of GOX present in the $A^3IS$, is shown in FIG. 5a, FIG. 5b and Table 6. Such a reservoir advantageously provides hydrogen peroxide, and its antimicrobial activity, for immediate effect upon application of $A^3IS$. Combined with higher level of hydrogen peroxide produced upon dilution, this would be expected to contribute to a significantly increased antimicrobial effect compared with other systems such as Manuka honey.

Example 6

$A^3IS$—Endogenous Hydrogen Peroxide Reservoir is Storage Stable

Figure 6:
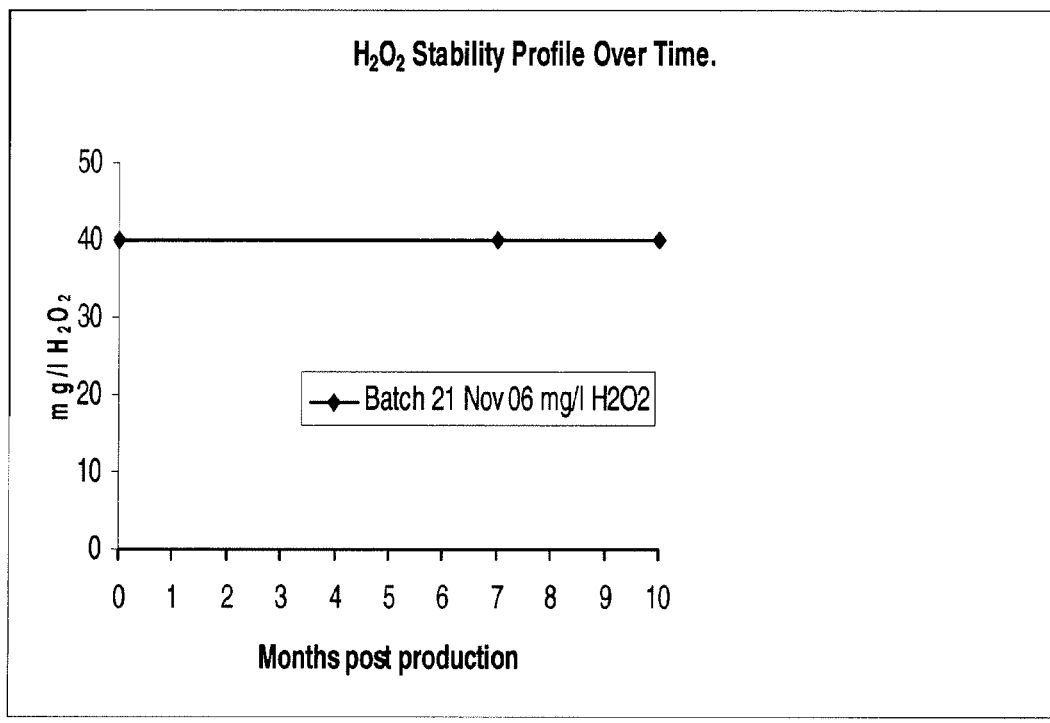

A surprising and advantageous feature of $A^3IS$ is the retention of both antimicrobial activity and the hydrogen reservoir over time as shown in FIG. 6.

Figure 7A:
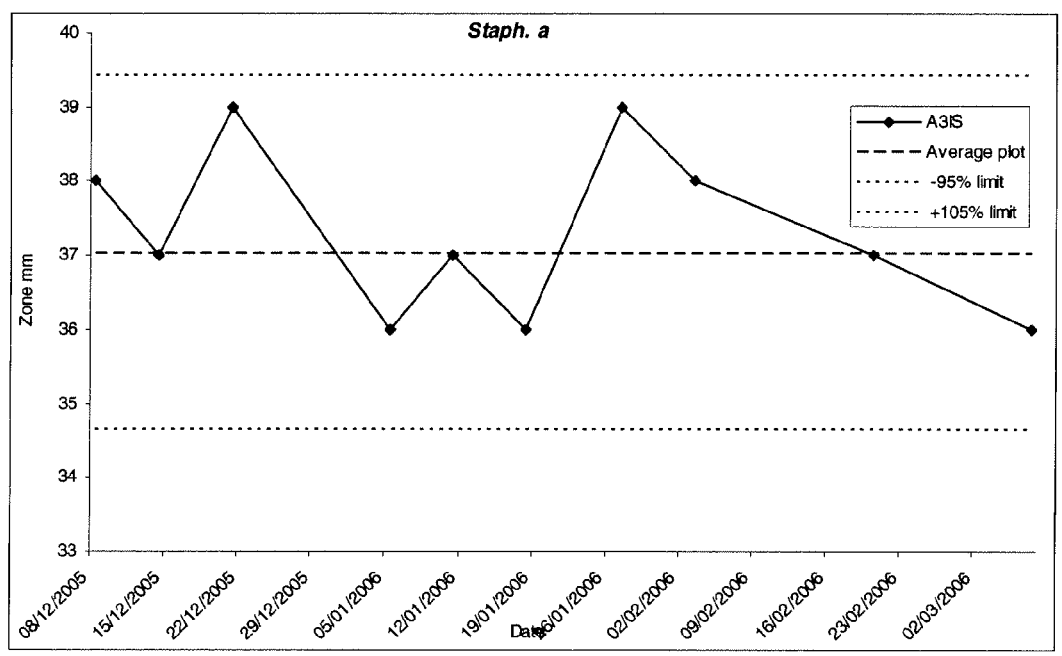
Figure 7B:
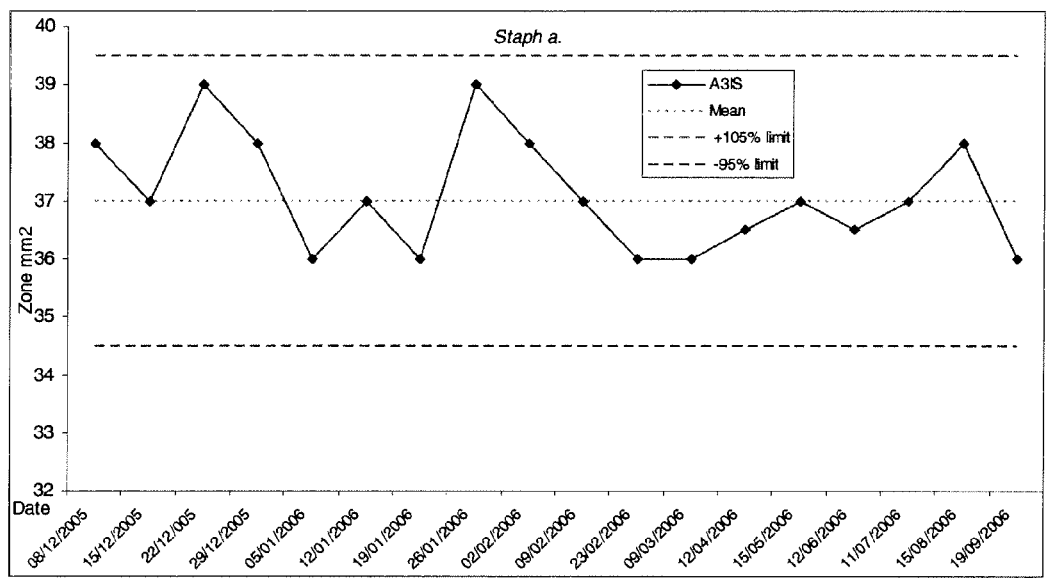

The available $H_2O_2$ reservoir produced by $A^3IS$ is storage stable as batches placed on stability retain the same levels of $H_2O_2$ as that detected when the batches are initially produced. Retention through stability of immediately available $H_2O_2$ is a unique feature of the $A^3IS$ formulations. Using the well diffusion assay to assess antimicrobial activity we demonstrate that a consistent level of antimicrobial activity is maintained over time. FIG. 7a shows the zones of inhibition measured at each sampling time point and the results graphed using 95% confidence limits during a period of three months. Similarly FIG. 7b shows extended stability of antimicrobial activity over a 9 month period. Extended stability data indicates that the $A^3IS$ formulation shows no loss of activity even after a period of 14 months.

Using the well diffusion assay to assess antimicrobial activity we demonstrate that a consistent level of antimicrobial activity over time. FIG. 7a shows the zones of inhibition measured at each sampling time point and the results graphed using 95% confidence limits during a period of three months. Similarly FIG. 7b shows extended stability of antimicrobial activity over a 9 month period. Extended stability data indicates that the $A^3IS$ formulation shows no loss of activity even after a period of 14 months.

Example 7

$A^3IS$—Potent Antimicrobial Activity Against *Staphylococcus aureus*

Figure 8A:
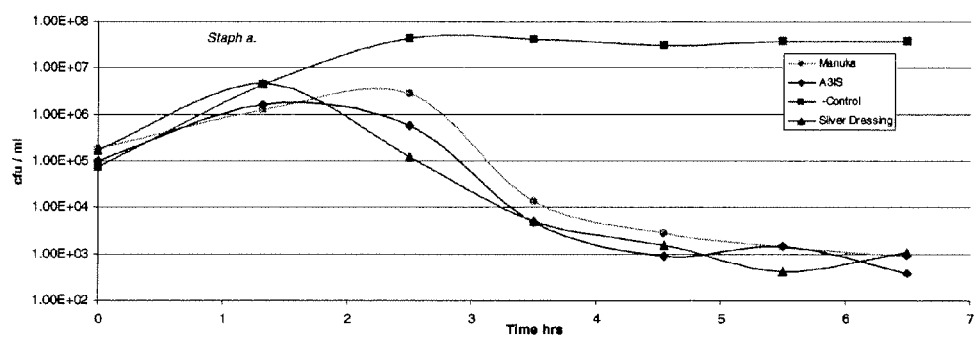
Figure 8B:
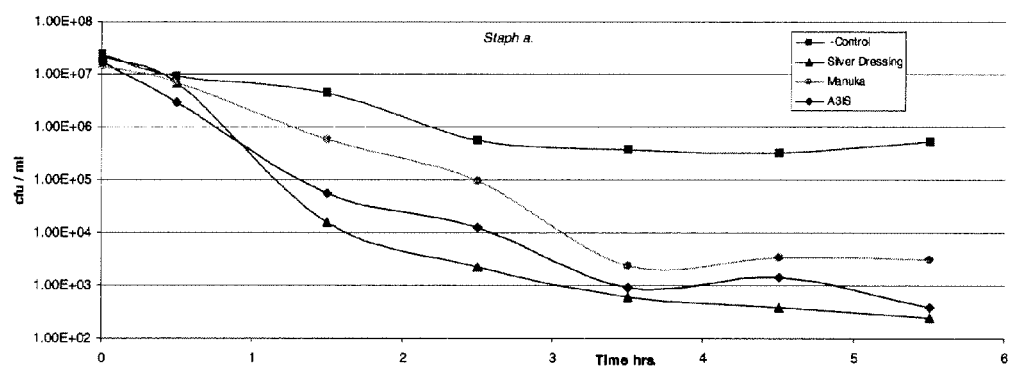

$A^3IS$ is shown to have antimicrobial activity against *Staphylococcus aureus*. FIG. 8a and FIG. 8b shows bacterial kill curves performed using two separate protocols, the NCCLS guidelines, method (FIG. 8a) and a Medical device manufacturer's specific protocol (FIG. 8b) over a 6.0 hour period. $A^3IS$ has increased efficacy compared with Manuka honey and comparable efficacy to silver dressing.

Figure 8C:
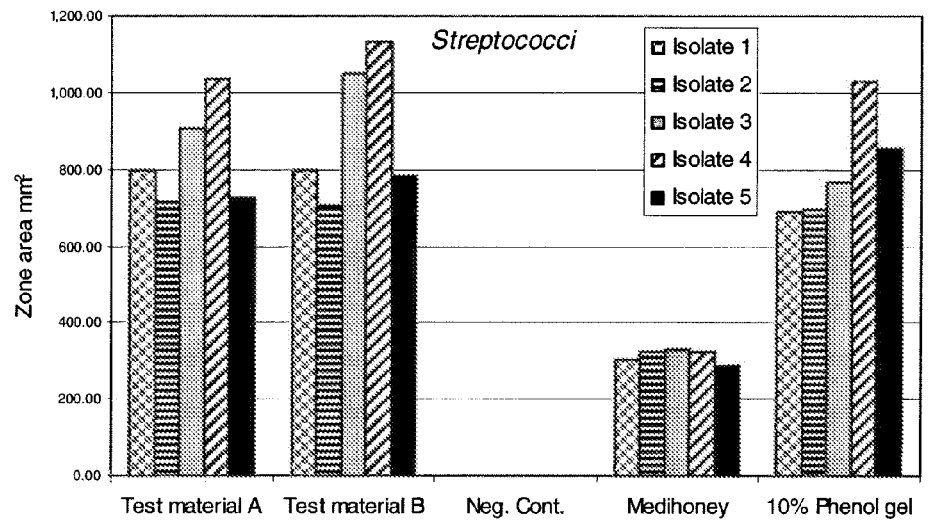

FIG. 8c shows the results of an inhibition assay (3 day repeats) for $A^3IS$, Medihoney® and a 10% phenol gel when tested against 5 clinical isolates of the Beta haemolytic Streptococci Group A. $A^3IS$ is at normal pH 5.5 (test material A) and pH 7 (test material B), a negative control of $A^3IS$ containing no GOX is included. Formulation $A^3IS$ demonstrates comparable in vitro efficacy to a 10% phenol gel and is superior to Medihoney®.

Example 8

$A^3IS$—Potent Antimicrobial Activity Against *Campylobacter*

Figure 8D:
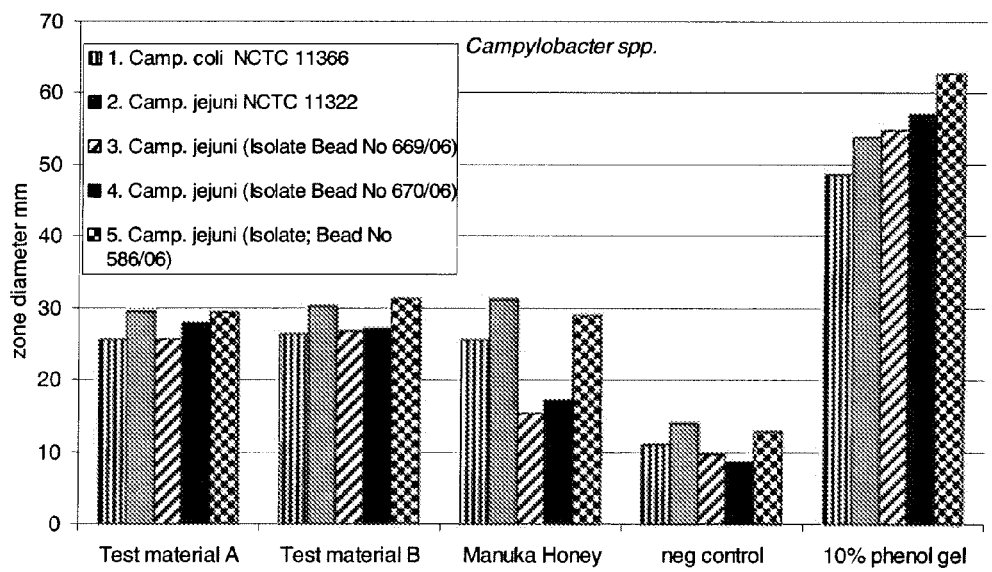

$A^3IS$ is shown to have antimicrobial activity against *Campylobacter*. FIG. 8d shows the results of an inhibition assay (3 day repeats) for formulation $A^3IS$, Manuka honey and a 10% phenol gel when tested against 5 clinical isolates of the *Campylobacter* spp. Formulation $A^3IS$ is at normal pH 5.5 (test material A) and pH 7 (test material B), a negative control $A^3IS$ containing no GOX is included. Results indicate significant anti-*Campylobacter* in-vitro efficacy and the superiority of $A^3IS$ over Manuka honey.

Example 9

$A^3IS$—Potent Antimicrobial Activity Against *Propionibacterium acnes*

$A^3IS$ is shown to have antimicrobial activity against *Propionibacterium acnes* (*P. acnes*).

Figure 9A:
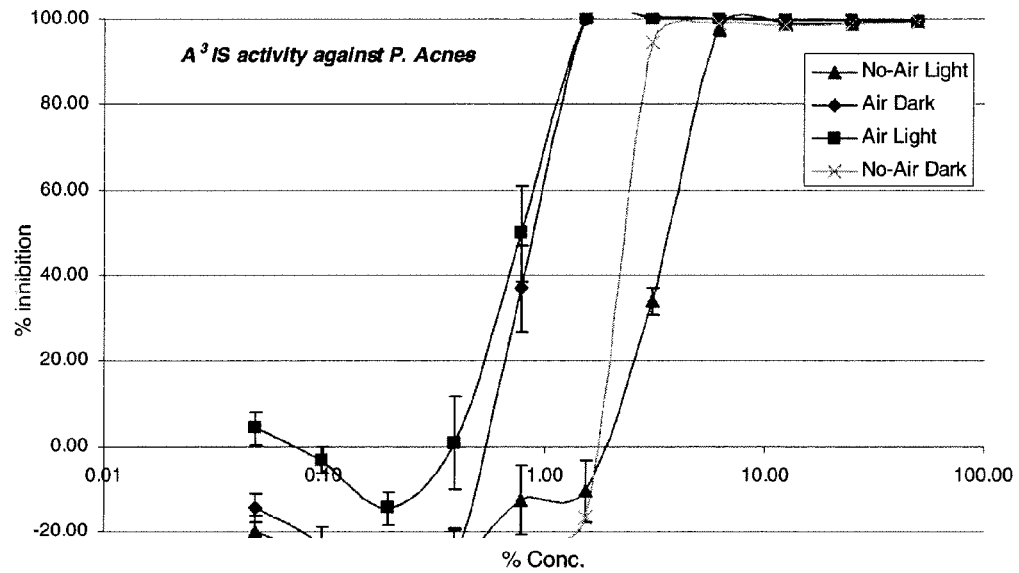
Figure 9B:
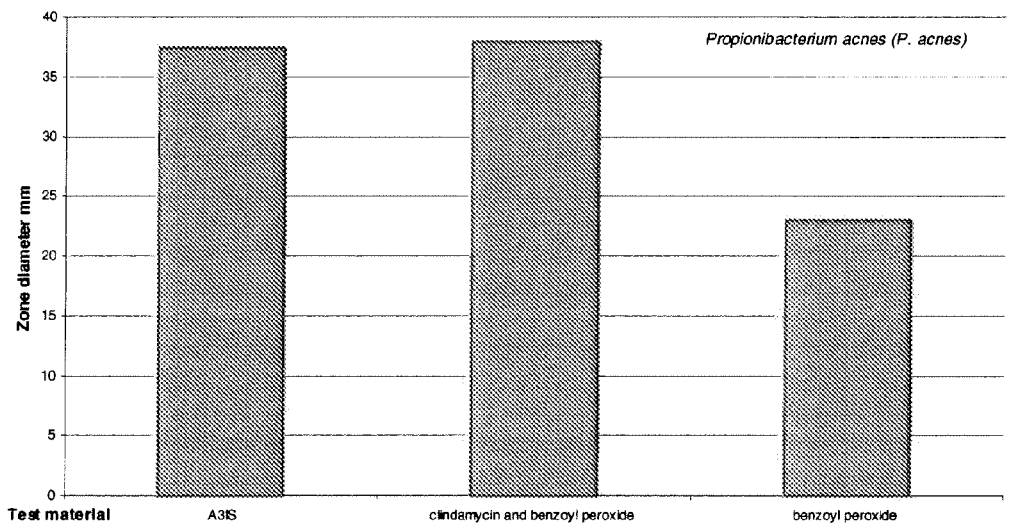

FIG. 9a. shows the inhibition results of $A^3IS$ against *P. acnes* under varying incubation conditions: light and dark aerobic, light and dark anaerobic. $A^3IS$ demonstrates a high level of activity against *P. acnes*, indicating the material may have potential for topical acne application. The results for $A^3IS$ and currently available anti-acne commercial products including some commercial products which incorporate antibiotics are shown in FIG. 9b. These results indicate that $A^3IS$ is comparable with 'respect to' in vitro anti-acne efficacy to commercially available anti-acne products containing Clindamycin and Benzoyl peroxide.

Example 10

A³IS—Potent Antimicrobial Activity Against MRSA

Figure 10:
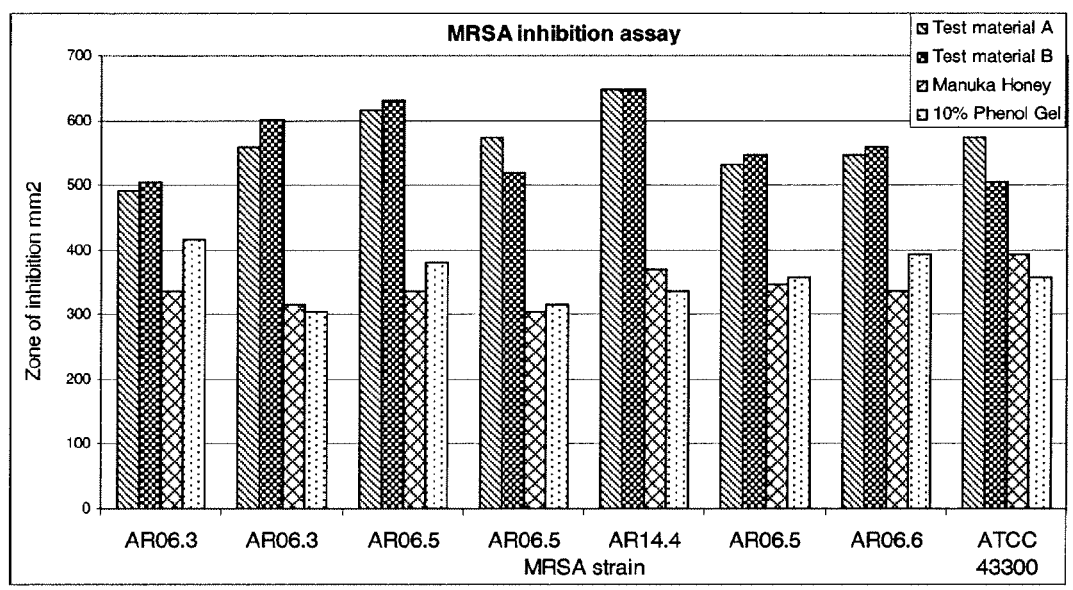
Figure 11A:
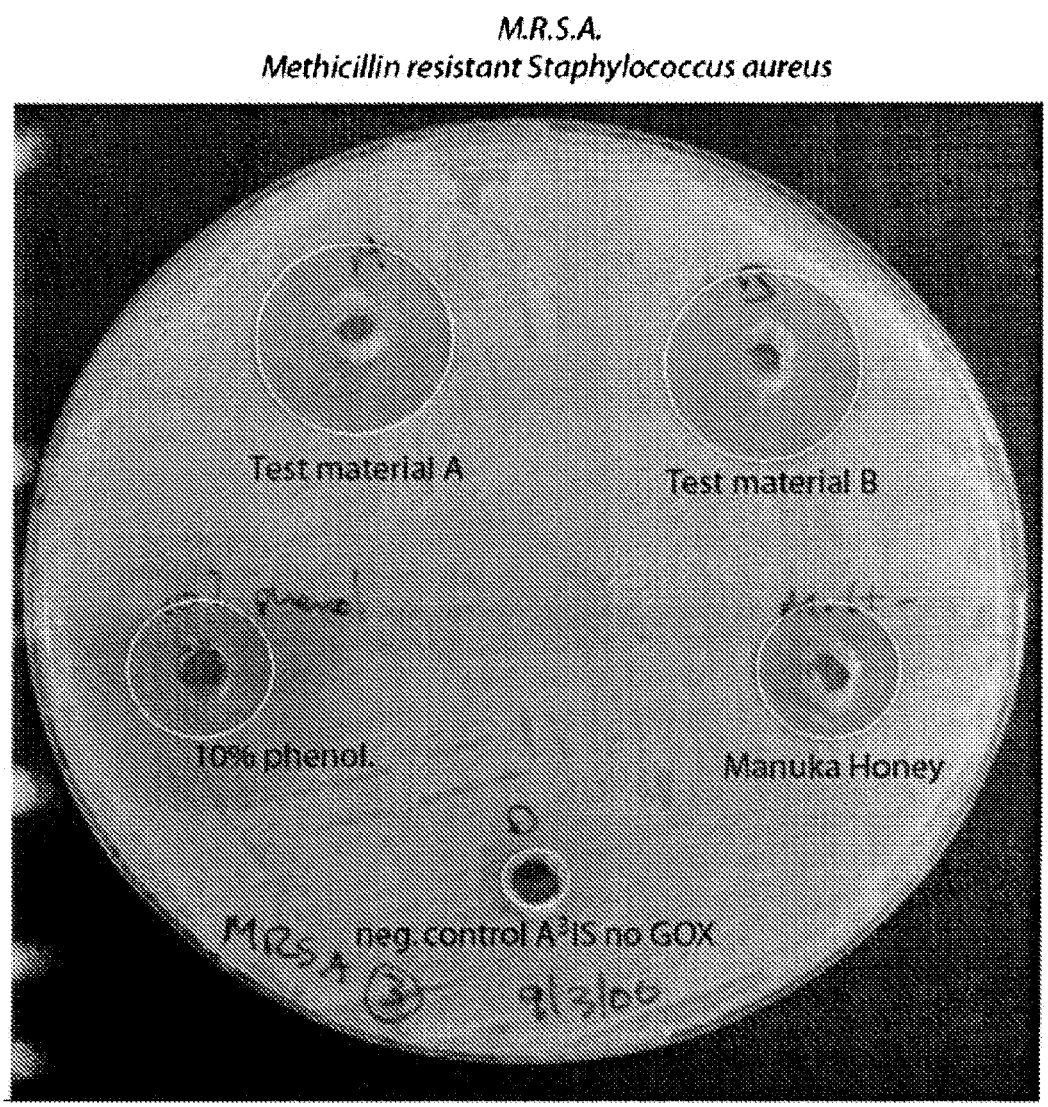

The Antimicrobial System formulation is shown to have antimicrobial activity against 8 strains of MRSA on three different days and compared to a 10% phenol standard and to Manuka honey FIG. 10. Formulation A³IS is at normal pH 5.5 (test material A) and pH 7 (test material B), a negative control A³IS containing no GOX is included. The results demonstrate significant in vitro anti-MRSA efficacy and the superiority of A³IS over Manuka honey and a 10% phenol gel control. Zones of inhibition are shown in FIG. 11*a*. Test material A is adjusted to pH 5.5 and test sample B is adjusted to pH 7. FIG. 11*a* shows the enhanced results of A³IS which is approximately 300% better than the Manuka honey. This clearly shows that the A³IS has superior and advantageous properties over and above Manuka honey.

Example 11

Figure 11B:
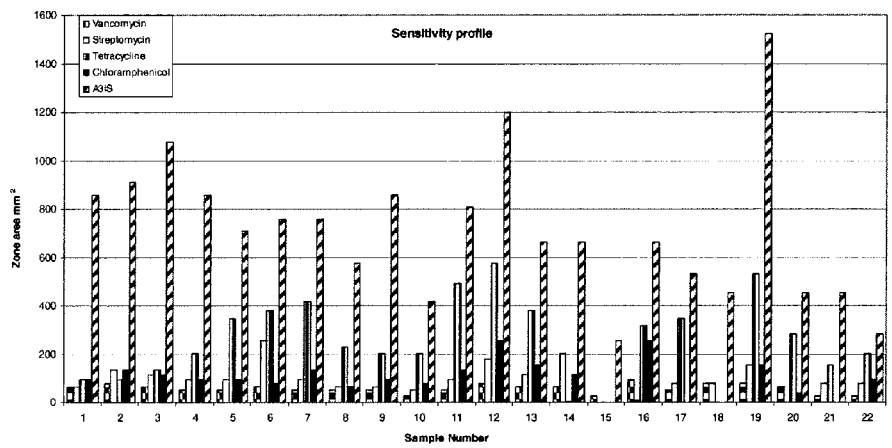

A³IS—Potent Antimicrobial Activity Against Clinical Isolates of Mastitis and Retention of Activity in Raw Milk FIG. 11*b* shows the results of an inhibition assay (3 day repeats) for A3IS and four antibiotics (Vancomycin, Streptomycin, Tetracycline and Chloramphenicol) when tested against 22 clinical isolates of Mastitis causing *Staphylococcus aureus* organisms. Formulation A³IS demonstrates superior in vitro efficacy to all of these antibiotics. Clinical isolate number 15 is resistant to Vancomycin, Streptomycin and Tetracycline and shows only mild sensitivity to Chloramphenicol, however, it demonstrates sensitivity to A3IS.

Figure 11C:
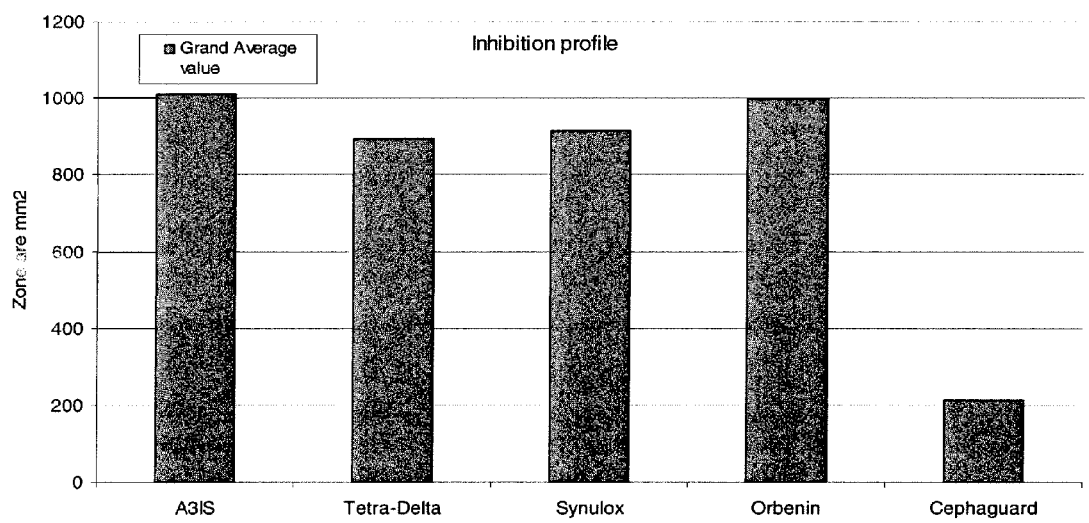

FIG. 11*c* shows the results of an inhibition assay (3 day repeats) for A³IS when tested against 22 clinical isolates of Mastitis causing *Staphylococcus aureus* organisms. Formulation A³IS demonstrates comparable in vitro efficacy to three of the leading commercially available multi antibiotic products for Mastitis and is superior to one of these products.

Figure 11D:
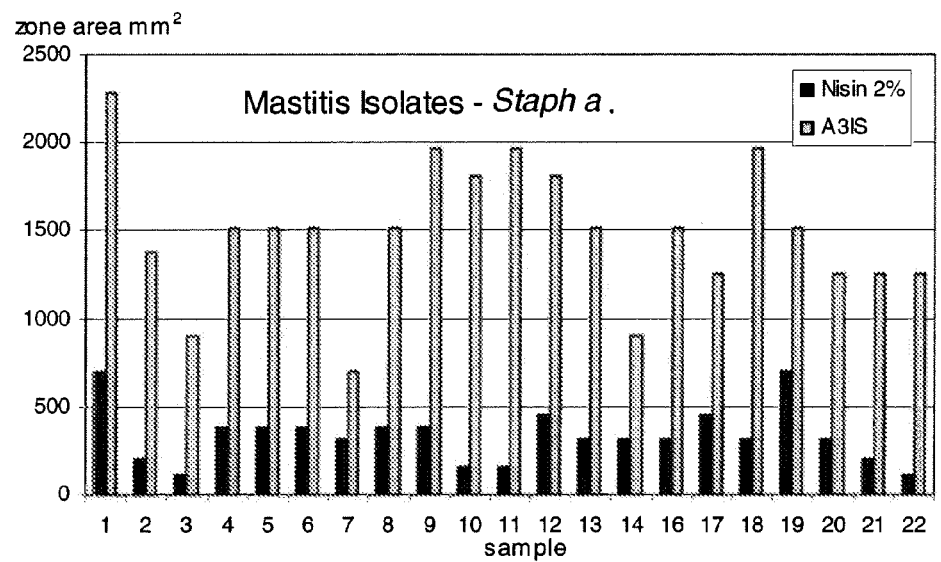

FIG. 11*d* shows the results of an inhibition assay (3 day repeats) for A³IS tested against a 2% Nisin solution on 21 clinical isolates of Mastitis causing *Staphylococcus aureus* organisms. Formulation A³IS demonstrates superior in vitro efficacy to the 2% Nisin solution. Note: Clinical isolate number 15 of FIG. 11*b* was unrecoverable from storage and is not included in this assay.

Figure 11E:
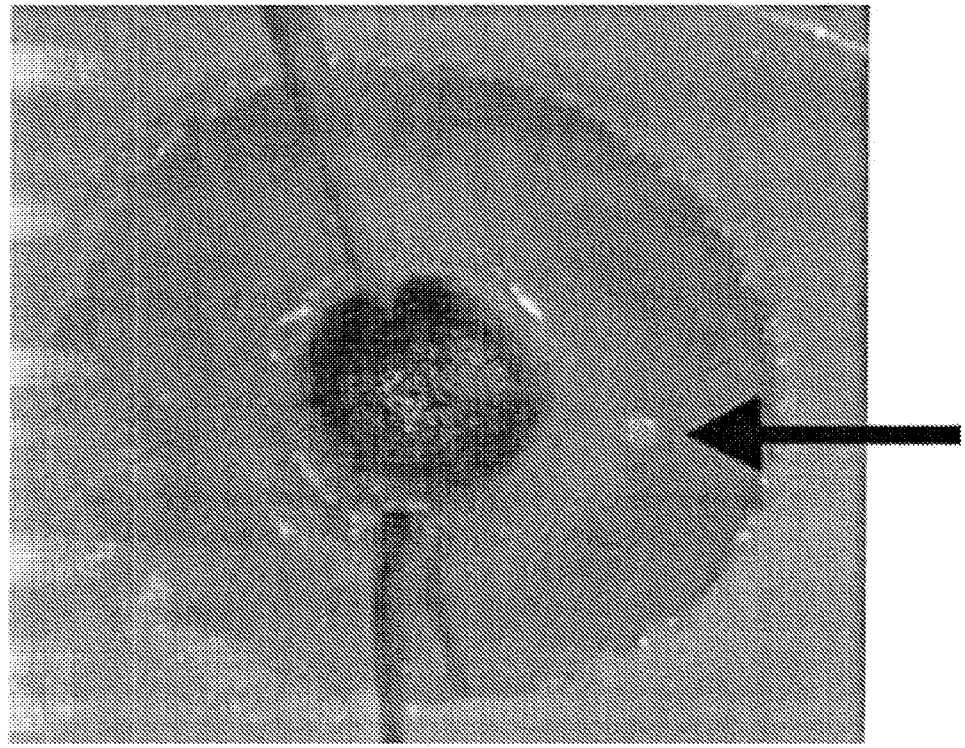

FIG. 11*e* shows the presence of a 2% Nisin resistant colony within the zone of inhibition during a Nisin efficacy study. A³IS resistant colonies have never been observed in efficacy studies based on zone of inhibition assays, nor has regrowth of cultures occurred following spectrophotometric based A³IS inhibition assays.

Five mls of raw milk is inoculated with 0.1 mls of an overnight culture of *Staphylococcus aureus* (containing approximately $5 \times 10^7$ cfu/ml) followed by the addition of 0.5 mls of A³IS formulation. This mixture is incubated overnight at 37° C. The mixture is then analysed for $H_2O_2$ production and survival of the inoculated *Staphylococcus aureus*. Levels of $H_2O_2$ in excess of 100 mg/l are detected in this milk and few of the inoculated *Staphylococcus* are recovered. The mixture shows no sign of souring which would be expected following overnight incubation at this temperature. By contrast, raw milk to which the A³IS is not added sours and coagulates. This finding indicates A³IS retains activity even in a complex medium such as raw milk

Example 12

A³IS—in-vitro Toxicity/Irritancy Measurement

Toxicity/irritancy is determined using normal human fibroblasts (NHFs ECACC 90011807) and normal human keratinocytes (NHKs CC-2501) grown in Eagles Minimum Essential Medium (EMEM) with, 2 mM L-Glutamine, 10% Foetal Bovine Serum (FBS), incubated at 37° C. in 5% $CO_2$. Three repeats of two dimensional assays using 24 and 12 well plates, utilising both neutral red and 3-(4,5-Dimethylthiazol-2-yl)-2,5-diphenyltetrazolium bromide (MTT), Sigma, 'In Vitro Toxicology Assay Kit' for direct contact cell assays are performed, to assess viability after incubation with test materials for 8 hrs (sodium azide—positive control, concentrations of silver gel, zinc gel, A³IS and fresh media—negative control).

ISO 10993, agar overlay tests for cytotoxicity: in vitro method is also used, employing L929 cells (mouse fibroblasts ECACC 85011425). In brief; a confluent monolayer of cells is incubated, this is then covered with a layer fresh medium (EMEM, 2 mM L-Glutamine, 5% FBS, 2% Penicillin-Streptomycin) containing 1.5 g/l of soft agar and allowed to solidify. One tenth of the surface is covered with test materials (previously described) and incubated for 24 hrs. Post incubation the test material is carefully removed and a vital stain (neutral red) in fresh media added. After incubation this is removed, the cells washed and then the dye extracted from the cells and quantified spectrophotometrically for cell viability.

A three dimensional dermal skin model (Skinethic, France) is also employed to determine the irritant effect of the formulation and controls on differentiated keratinocytes as in the stratum corneum, a cultured skin equivalent. The assay employs a three dimensional epidermal skin model and is carried out at several time points. The reconstituted human epidermis model consists of an airlifted, living, multi-layered epidermal tissue construct, produced in polycarbonate inserts in serum-free and chemically defined medium, featuring normal ultra-structure and functionality equivalent to human epidermis in vivo. Quadruplicate in vitro reconstituted human epidermis tissues, age day 17, (size 0.63 cm²) are dosed topically with 2-10 mg/cm² of the formulation for 3 and 24 hours and tissue viability assessed using MTT assay, using the German Federal Institute for Risk Assessment (BFR-ZEBET) validated protocol.

Cell culture supernatant from the irritancy assay described previously is analysed using an IL-1 Enzyme-Linked Immuno Sorbent Assay (ELISA) (R&D Systems) and a Lactate Dehydrogenase (LDH) ELISA (R&D Systems), for cytokine and enzyme measurement to assess immunostimulatory and irritant effect of test materials.

Cross sections of the 3D skin models used for the irritancy assay are stained with haematoxylin and eosin (H&E), The Technical Procedure Included:

Fixation: The tissues are mechanically and biochemically stabilised in a fixative. The fixative is neutral buffered formalin, 10% formaldehyde in phosphate buffered saline (PBS).

Embedding: The technique used is wax embedding. The samples are progressively immersed in increasing concentrations (20%, 30%, 40%, 50%, 80% and 100%) of pure ethanol to dehydrate the tissue, followed by a clearing agent, xylene (100%), and finally hot molten paraffin wax (impregnation) and allowed to cool and harden.

Sectioning: The sample tissue is then sectioned into 5 micrometer sections using a microtome. These slices are then placed on a glass slide for staining.

Staining: To view the tissue under a microscope, the sections are stained with hematoxylin and eosin (H&E) to assess the rate of surface epidermal degradation caused by each test material.

Figure 12A:
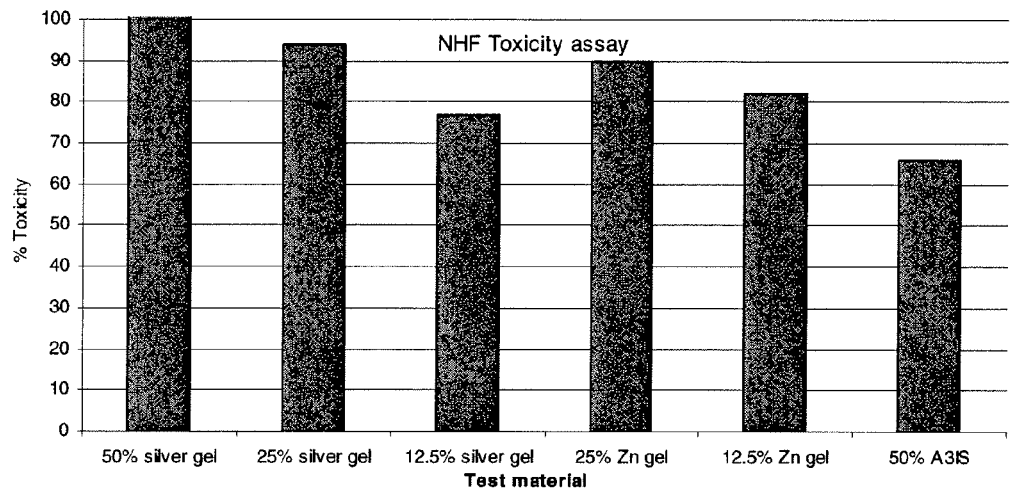
FIG. 12d shows A³IS and other test material MTT irritancy assay over a 24 hour period employing the Skinethic® 3D skin model. A³IS demonstrates less irritancy in this three dimensional assay than the commercially available products tested.
FIG. 12e shows Haematoxylin/Eosin (H&E) stained cross section of Skinethic® 3D skin exposed to the comparative silver containing gel product. Note that the silver formulation causes detachment of the epidermal layer from the basal layer.
FIG. 12f shows Haematoxylin/Eosin (H&E) stained cross section of Skinethic® 3D skin exposed to the comparative silver containing gel product. Note that the silver formulation causes detachment of the epidermal layer from the basal layer.
FIG. 12g shows Haematoxylin/Eosin (H&E) stained cross section of Skinethic® 3D skin exposed to A³IS, Note that A³IS does not cause detachment of the epidermal layer from the basal layer.
FIG. 12h shows Haematoxylin/Eosin (H&E) stained cross section of Skinethic® 3D skin exposed to A³IS. Note that A³IS does not cause detachment of the epidermal layer from the basal layer.
Figure 12B:
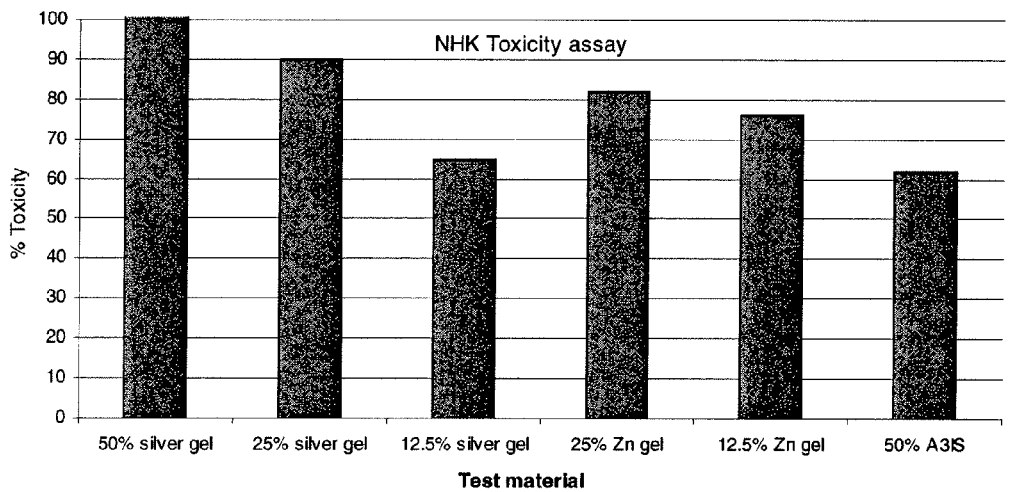

FIG. 12a and FIG. 12b show the results of the initial toxicity assessment of $A^3IS$ by means of the MTT viability assays on NHFs (Normal Human Fibroblasts) and NHKs (Normal Human Keratinocytes). Percent toxicity was calculated according to the formula: % Toxicity=1-(OD average of test material wells/average OD of corresponding control wells (no test material added))×100. Included in the assay are a 50% concentration of A3IS, a range of concentrations of a commercial silver containing gel and a commercial zinc containing gel product, compared to sodium azide (positive control). For the toxicity assay the concentration of test material used was twice that used for the irritancy assay, a 100 mg per well and the contact time was extended to 8 hrs.

Figure 12C:
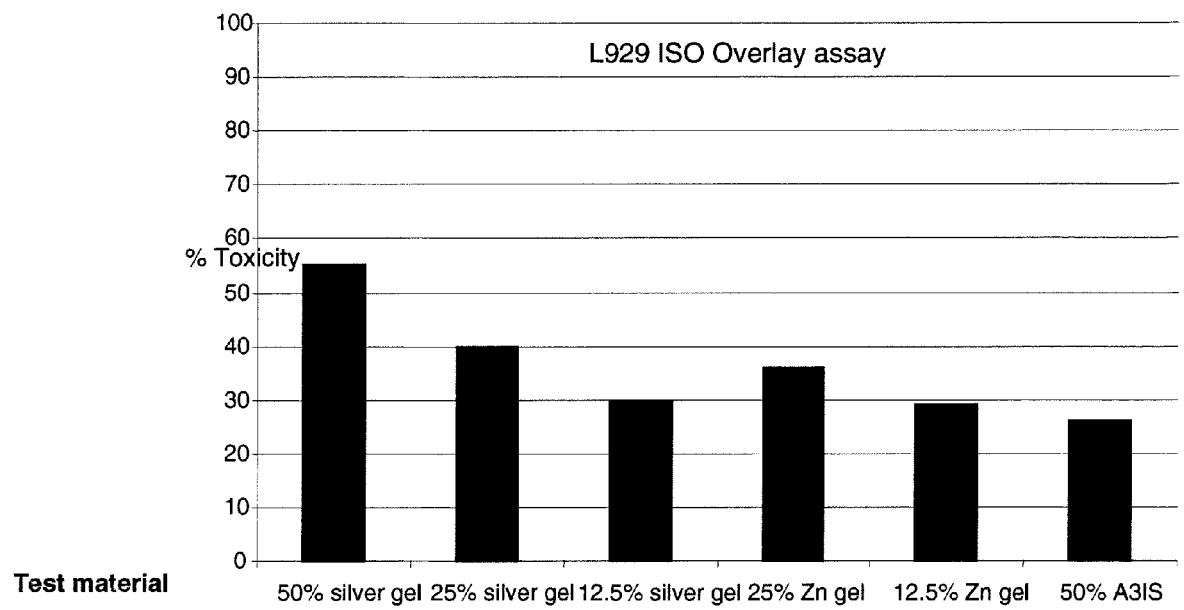

FIG. 12c shows the results of the ISO International Standard, 10993-5 agar overlay assay for cytotoxicity over 24 hrs using neutral red on L929s. Percent toxicity was calculated according to the formula: % Toxicity=1-(OD average of test material wells/average OD of corresponding control wells (sodium azide added))×100. Included in the assay are a 50% concentration of $A^3IS$, a range of concentrations of commercial silver containing gel and commercial zinc containing gel product, compared to sodium azide (positive control). The sodium azide positive control gives 100% toxicity. For the agar overlay toxicity assay the amount of test materials used was similar to that used for the initial direct contact assays of 100 mg per well however the contact time was extended to 24 hrs.

Figure 12D:
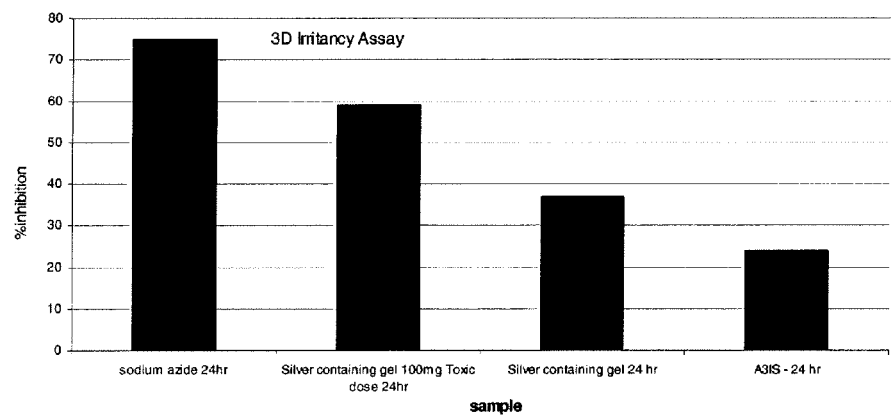
Figure 12E:
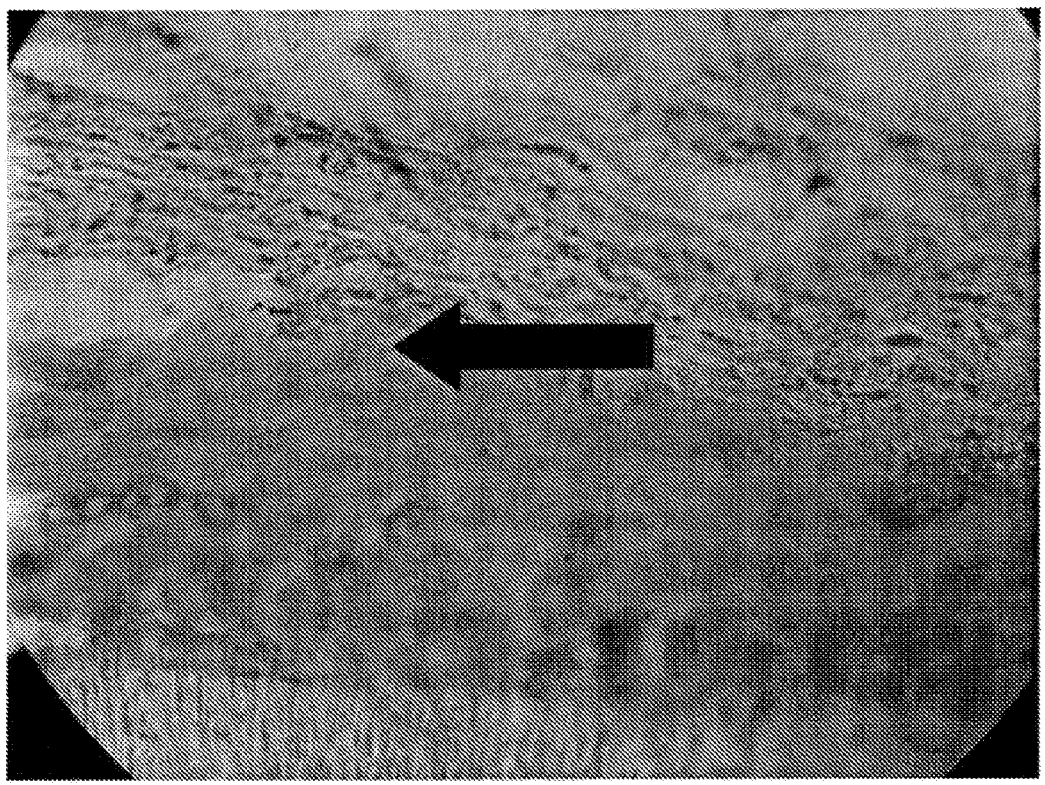
Figure 12F:
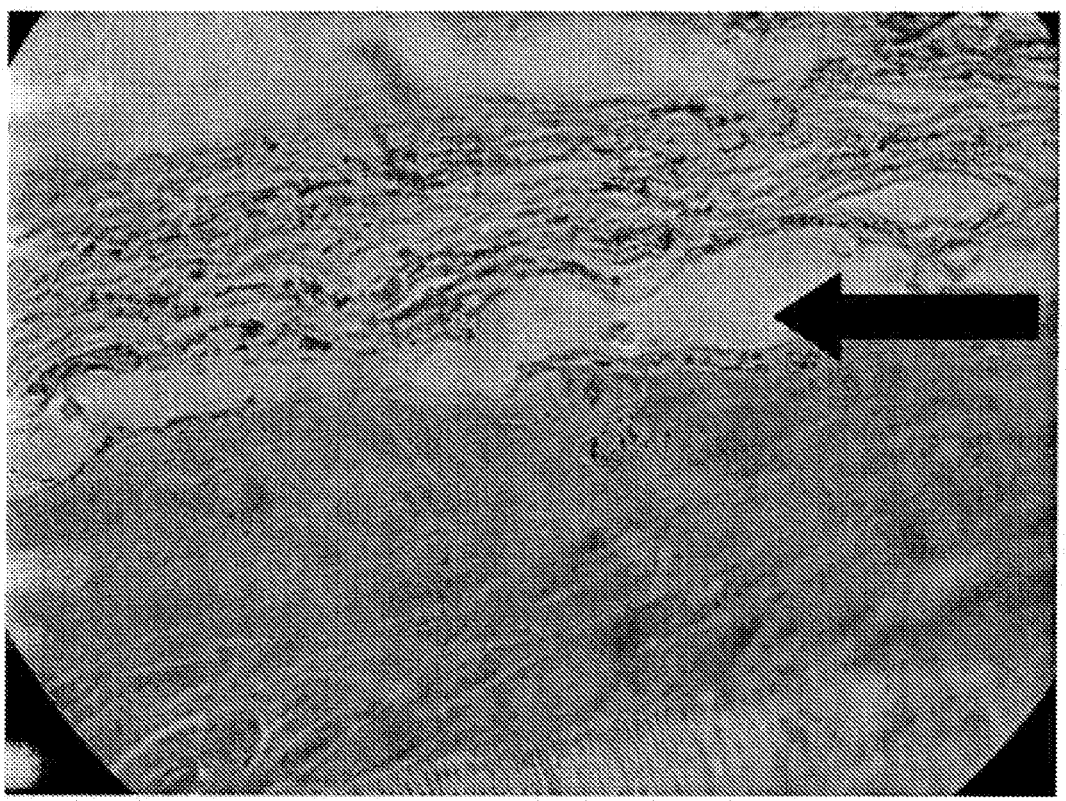
Figure 12G:
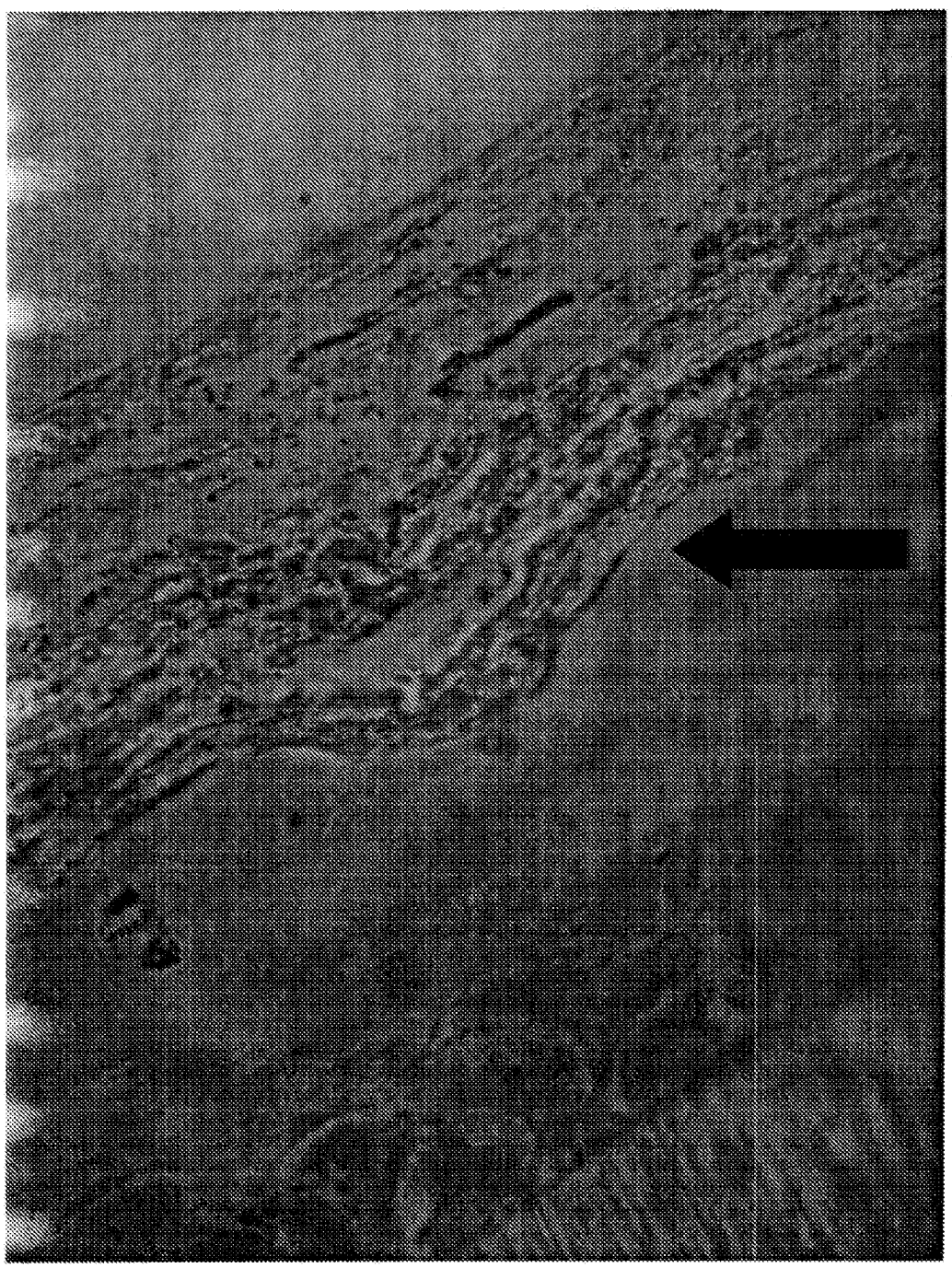
Figure 12H:
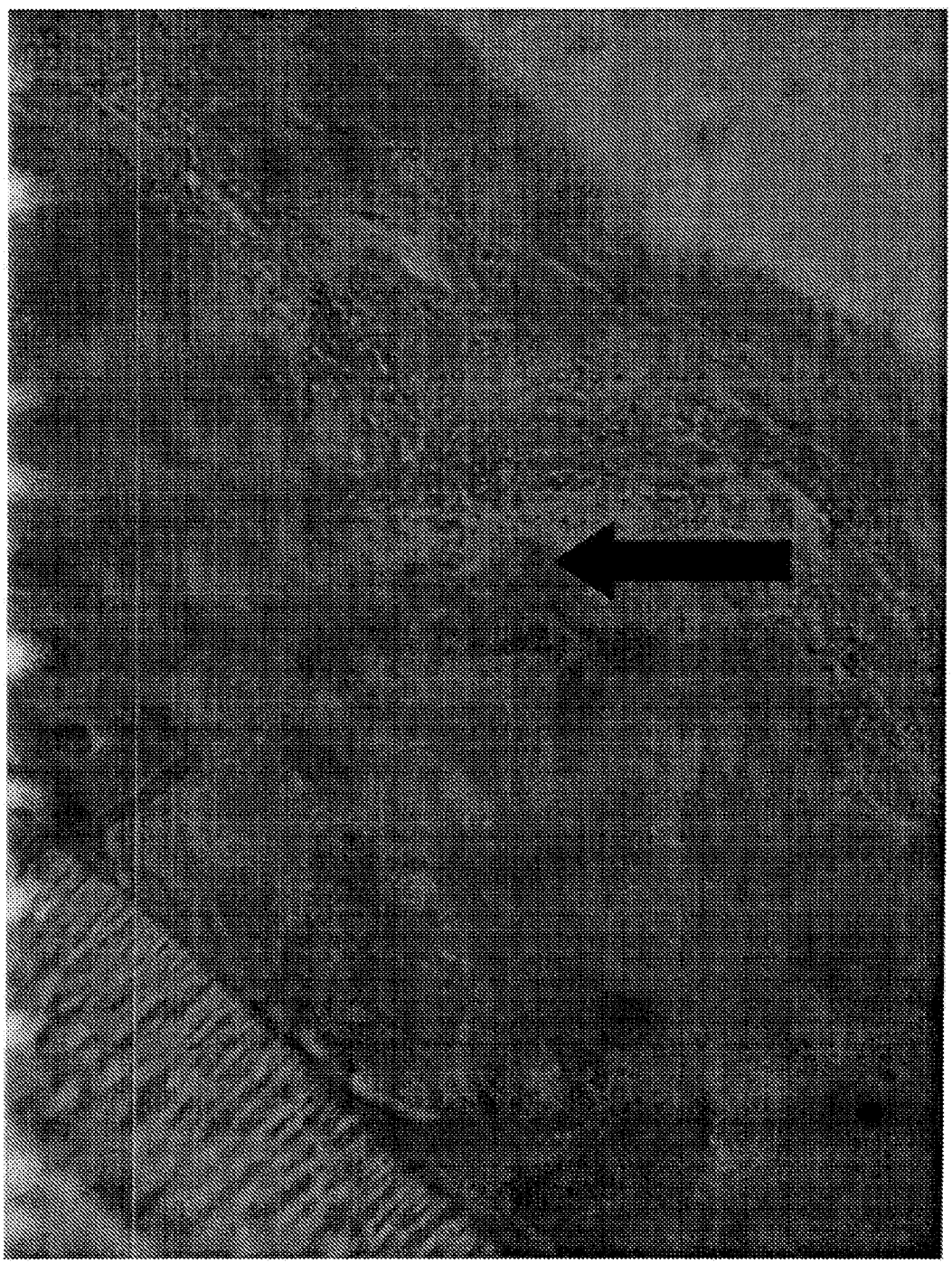

The results of an irritancy assay of the test materials for a range of contact times employing Skinethic® 3D skin model are shown in FIG. 12d. This reconstituted human epidermis model consists of an airlifted, living, multi-layered epidermal tissue construct, produced in polycarbonate inserts in serum-free and chemically defined medium, featuring normal ultrastructure and functionality equivalent to human epidermis in vivo. The effects of this direct contact on the 3D skin samples are shown on Haematoxylin/Eosin (H&E) stained cross sections in FIG. 12e and FIG. 12f for the comparative silver containing gel product. FIG. 12g and FIG. 12h show H&E stained cross sections following $A^3IS$ formulation direct contact on the 3D skin samples. The results show that the silver formulation causes detachment of the epidermal layer from the basal layer, whereas the sample $A^3IS$ formulation exhibits no damage.

Quadruplicate in vitro reconstituted human epidermis tissues, age day 17, (size 0.63 cm$^2$) were dosed topically with 2-10 mg/cm$^2$ of the formulation for 3 and 24 hours and tissue viability assessed using MTT assay, using the German Federal Institute for Risk Assessment (BFR-ZEBET) validated protocol. Percent irritancy was calculated according to the formula: % Irritancy=1-(OD average of test material skins/average OD of corresponding control skins (no test material added))×100. $A^3IS$ demonstrates less irritancy in this three dimensional assay than the commercially available products tested.

Example 13

$A^3IS$—Induction of Inflammatory IL-1 Release from Skin Cells

FIG. 13a shows the results of an ELISA assay of the supernatant removed during the 3D irritancy assay over a 48 hour period, measuring and comparing the release of IL-1 when exposed to $A^3IS$ formulation, to a sodium azide positive control, and a commercial silver containing gel product. The results indicate that IL-1 is released from the skin cells exposed to the $A^3IS$ formulation. FIG. 13b Illustrates the measurement of released Lactate Dehydrogenase (LDH) in the cell media used during the irritancy test protocol. Results show LDH release by cells following exposure to the $A^3IS$ formulation, a sodium azide positive control, and a commercially available silver containing gel product. Lactate dehydrogenase is released by cells exposed to destructive compounds. The results indicate that the $A^3IS$ formulation is less toxic than commercially available silver containing gel products.

Example 14

$A^3IS$—Terminal Sterilisation $A^3IS$ was filled into glass bottles and plastic tubes. These were then sterilised by Gamma irradiation. Post sterilisation, the samples antibacterial activity was compared to pre sterilisation results. It was found that Gamma irradiation did not reduce activity. There was slight discolouration of the primary container; however the irradiation process did not affect the activity or the colour of the test material FIG. 14 shows the efficacy of $A^3IS$ prior to and after gamma irradiation on S. aureus, E. coli and Pseudomonas aeruginosa.

Example 15

$A^3IS$—Incorporation in a Collagen-GAG (Glycosaminoglycan) Matrix—as an Antibacterial Dressing Picture of $A^3IS$ in GAG on S aureus and pictures of the infiltration of GAG (FIG. 15a to FIG. 15c).

Collagen-GAG (glycosaminoglycan) matrix as has been previously described (Wilkins, L., M., et al, 1993. Development of a bilayered Living Skin Construct for Clinical Applications. Organogenesis Inc.) is formulated and A3IS was added to this matrix at a ratio of 1:1.

The mixture is poured onto a sterile surface to form a thin layer of approx 1 mm and dried in an incubator for 24 hrs to form a skin dressing. Once dry, 1 cm sections are cut, and placed onto inoculated agar plates inoculated with S. aureus, E. coli and P. acnes. Antibacterial activity against S. aureus, E. coli and P. acnes is observed. There are clear defined zones of inhibition and no bacterial growth is observed under the dressing.

The test sections are also placed onto a confluent monolayer of NHFs (normal human fibroblasts) in 6 well plates at time T$_0$. It is found that there was little to no toxicity.

The test sections were also co-incubated with NHF cells, in cell culture wells. It was found that in addition to adhering to the bottom of the cell culture wells, as was expected, the NHF cells also infiltrated, attached to and grew on the test sections. This demonstrates that Collagen-GAG matrices incorporating $A^3IS$ are suitable matrices for cell attachment and growth (see FIG. 15b and FIG. 15c).

Example 16

$A^3IS$—Incorporation in an Alcoholic Gel $A^3IS$ is mixed with an alcoholic gel consisting of absolute alcohol, ultrez 10 gelling agent, di-isopropanolamine and propylene glycol, which is mixed prior to the addition of $A^3IS$ resulting in a clear non-adhesive material. This gel formulation is tested using the well diffusion and surface diffusion bio assay to determine zones of inhibition against S. aureus, E. coli and P. acnes. Results are shown for S. aureus FIG. 16a. It should be noted that the zones of inhibition are artificially low in this situation due to the absorptive property of the gel matrix, thus not allowing free diffusion through the agar matrix but there is a clear zone around the gel matrix.

The gel formulation is put on a short term stability study of 6 weeks, including a freeze thaw test. Results indicated that the gel formulation maintained stability throughout the test period FIG. 16b. Results are shown for S. aureus.

Example 17

$A^3IS$—Incorporation onto Commercially Available Wound Dressings

Picture of $A^3IS$ in Wound Dressings FIG. 17

Formulation $A^3IS$ was poured onto the surface of a range of commercially available dressings Kaltostat® (Comvita), Kendal® (Telfa) and a Collagen-GAG (glycosaminoglycan) matrix as previously described and allowed to diffuse into the dressing for several hours to form a thin layer of approximately 1 mm. 1 cm2 sections were cut and placed onto agar plates, previously inoculated with S. aureus, E. coli and P. aeruginosa. The antibacterial efficacy of $A^3IS$ impregnated dressings was then compared to Aquacel® (Convatec) and Betadine® (Seton) commercially available dressings that contain elemental silver and iodine FIG. 17. It was found that the $A^3IS$ dressings are as effective antimicrobially as Aquacel® (Convatec) and Betadine® (Seton) and a commercially available dressing that use elemental silver and iodine.

Example 18

$A^3IS$—Potent Antimicrobial Activity Against Onychomycosis

A case study on the efficacy of $A^3IS$ in the treatment of fungal nail infections was carried out on a human volunteer. The infected nail was the big toe nail on the right foot and the infection was localised on the left side of the nail. The infection had been present for a considerable period of time, approximately 2 years. Prior to treatment, a photograph of the infected nail was obtained FIG. 18a. The treatment was carried out once daily in the morning, subsequent to the subject having a shower and towelling dry. $A^3IS$ was applied to the surface of the nail over the infected region rather than over the entire nail surface. $A^3IS$ was then covered with a bandage whose wadding had been moistened using water and the nail was therefore covered in an occlusive dressing for the rest of the day FIG. 18b. This treatment was carried out daily for a period of three weeks. After a period of two days, another photograph was taken FIG. 18c. It is evident that the infected region of the nail has changed appearance in that it is now darker in colour. During the period of treatment, there was little evidence of further physical alteration except the development of an increasingly larger section of un-infected nail growing out. A further photograph 8 weeks after initiation of the treatment is shown FIG. 18d. In this the band of uninfected nail is clearly visible, indicating that the dermatophytes have been eliminated.

Example 19

Additional 2-Tier Storage-stable Formulations

The following formulations were made in accordance with the protocol of Example 3 (in 50 g batches). Each formulation was tested for the immediate presence of hydrogen peroxide using the protocols previously described. The compositions of each of the formulations prepared are outlined in the tables below. Ideally, 0.5% glucose oxidase enzyme (ideally at least 5600 U/g) pre-dissolved in water.

Formulation No: 1

| Ingredient | % w/w |
| --- | --- |
| Water | 10 |
| Glucose | 79.5 |
| Fructose | 7.5 |
| Maltose | 2.2 |
| Sucrose | 0.3 |
| Glucose Oxidase | 0.5 |

Formulation No: 2

| Ingredient | % w/w |
| --- | --- |
| Water | 20 |
| Glucose | 69.5 |
| Fructose | 7.5 |
| Maltose | 2.2 |
| Sucrose | 0.3 |
| Glucose Oxidase | 0.5 |

Formulation No: 3

| Ingredient | % w/w |
| --- | --- |
| Water | 10 |
| Glucose | 20 |
| Fructose | 52 |
| Maltose | 15.4 |
| Sucrose | 2.1 |
| Glucose Oxidase | 0.5 |

Formulation No: 4

| Ingredient | % w/w |
| --- | --- |
| Water | 20 |
| Glucose | 10 |
| Fructose | 52 |
| Maltose | 15.4 |
| Sucrose | 2.1 |
| Glucose Oxidase | 0.5 |

Formulation No: 5

| Ingredient | % w/w |
| --- | --- |
| Water | 18 |
| Glucose | 30 |
| Fructose | 40 |
| Maltose | 10 |
| Sucrose | 1.5 |
| Glucose Oxidase | 0.5 |

Formulation No: 6

| Ingredient | % w/w |
| --- | --- |
| Water | 20 |
| Glucose | 40 |
| Fructose | 29.5 |

-continued

| Ingredient | % w/w |
|---|---|
| Maltose | 10 |
| Sucrose | 0 |
| Glucose Oxidase | 0.5 |

Formulation No: 7

| Ingredient | % w/w |
|---|---|
| Water | 20 |
| Glucose | 40 |
| Fructose | 38 |
| Maltose | 0 |
| Sucrose | 1.5 |
| Glucose Oxidase | 0.5 |

Formulation No: 8

| Ingredient | % w/w |
|---|---|
| Water | 20 |
| Glucose | 30 |
| Fructose | 0 |
| Maltose | 48 |
| Sucrose | 1.5 |
| Glucose Oxidase | 0.5 |

Formulation No: 9

| Ingredient | % w/w |
|---|---|
| Water | 20 |
| Glucose | 40 |
| Fructose | 39.5 |
| Maltose | 0 |
| Sucrose | 0 |
| Glucose Oxidase | 0.5 |

Formulation No: 10

| Ingredient | % w/w |
|---|---|
| Water | 20 |
| Glucose | 60 |
| Fructose | 0 |
| Maltose | 19.5 |
| Sucrose | 0 |
| Glucose Oxidase | 0.5 |

Results

All batches were found to have both initial hydrogen peroxide content and antibacterial activity indicative of the sustained release of peroxide over a period of time.

H2O2 Generation mg\l:

| Formulation No. | Day 0 | Day 09 | Day 20 |
|---|---|---|---|
| 1 | ≥10 mg\l | ≥10 mg\l | ≥10 mg\l |
| 2 | ≥10 mg\l | ≥10 mg\l | ≥10 mg\l |
| 3 | ≥10 mg\l | ≥10 mg\l | ≥10 mg\l |
| 4 | ≥10 mg\l | ≥10 mg\l | ≥10 mg\l |
| 5 | ≥10 mg\l | ≥10 mg\l | ≥10 mg\l |
| 6 | ≥10 mg\l | ≥10 mg\l | ≥10 mg\l |
| 7 | ≥10 mg\l | ≥10 mg\l | ≥10 mg\l |
| 8 | ≥10 mg\l | ≥10 mg\l | ≥10 mg\l |
| 9 | ≥10 mg\l | ≥10 mg\l | ≥10 mg\l |
| 10 | ≥10 mg\l | ≥10 mg\l | ≥10 mg\l |

Example 20

Inhibition Assays for Hydrogen Peroxide and Antibiotic Combinations

Various combinations of $A^3IS$ (from Example 3) and antibiotics/antifungal agents were tested against a placebo and $A^3IS$ alone using a well/disc diffusion method. The following samples were used:
a) 100 μl of $A^3IS$;
b) combination placebo and antibiotic/antifungal comprising 50 μl of placebo ($A^3IS$ containing no GOX) and 50 μg an antibiotic/antifungal agent; and
c) combination $A^3IS$ and antibiotic/antifungal —50 μl of combination of $A^3IS$ and 50 μg of an antibiotic/antifungal agent.

Well/Disc Diffusion Methods for Measurement of Microbial Inhibition:

Agar plates were inoculated by swabbing overnight culture onto the plate surface. Plates were allowed to stand at room temperature for 15 minutes before use. Wells 8.2 mm diameter were bored into the surface of the agar. 100 μl of samples (a) to (c) was placed into each well. The samples diffuse into the agar around the well and are assayed for an ability to produce a zone of inhibition. Plates are incubated for 24, 48 or 72 hrs and zones of inhibition are measured. The diameter of zones, including the diameter of the well (8.2 mm) was recorded.

Results:

The results are shown in FIG. 19. FIG. 19 shows the results of an inhibition assay against *Candida albicans*.

Conclusion:

The combination of $A^3IS$ and antifungal resulted in a greater zone of inhibition indicating synergy between the two agents. A synergistic effect, going beyond that of a combination/additive effect, is observed despite an effective 50% reduction in the concentration of $A^3IS$ when used in combination (50 ul) compared to $A^3IS$ when used alone (100 ul). This effect was observed for *Candida albicans*.

Example 21

Synergy Tests for Hydrogen Peroxide and Antibiotic Combinations

Materials and Method:

The checkerboard technique was performed (Rochon-Edouard S, Pestel-Caron M, Lemeland J F, Caron F: In vitro synergistic effects of double and triple combinations of b-lactams, vancomycin and netilmicin against methicillin-resistant *Staphylococcus aureus* strains. Antimicrob Agents Chemother 2000, 44:3055-60; Eliopolus G M, Moellering R C Jr: Antimicrobial combinations. In Antibiotics in Laboratory medicine. 3rd edition. Williams and Wilkins, Co. Baltimore, Md. USA; 2000:432-49), including the combinations: A3IS/Flucloxacillin, A3IS/Zinacef, A3IS/Erythrocin, A3IS/Klacid, A3IS/Velocef, A3IS/Amoxicillin, A3IS/Clindamycin and A3IS/Augmentin. Stock solutions were prepared according to published standards (CLSI (Clinical and Laboratory Standards Institute): Performance Standards for Antimicrobial Susceptibility testing. Fifteenth Informational Supplement. CLSI document M100-S15. Pennsylvania USA 2005, 19087-1898)

Results

Results of the checkerboard synergy testing are summarized in the tables below.

| Checkerboard Synergy Test | | | | | |
|---|---|---|---|---|---|
| Pre-dilution concentrations of A³IS and antibiotics. | A³IS 0.5% GOX | Flucloxacillin 500 mg | Zinacef 750 mg | Erythrocin 1.00 g | KIacid 500 mg |
| Final dilutions of A³IS and antibiotics for checkerboard synergy test | A³IS 3% | Flucloxacillin 1:3,200,000 | Zinacef 1:400,000 | Erythrocin 1:1,600,000 | KIacid 1:1,600,000 |
| MICs for A³IS & antibiotics on S. aureus NCIMB 9587. | A³IS ⅛ | Flucloxacillin ½ | Zinacef ½ | Erythrocin ½ | KIacid ½ |
| FICs for combination (A³IS + antibiotic) on S. aureus NCIMB 9587 for checkerboard synergy tests. | | A³IS + Flucloxacillin 1.35 | A³IS + Zinacef 0.5 | A³IS + Erythrocin 2.00 | A³IS + KIacid 1.0 |
| | | No Synergy | Synergy | No Synergy | No Synergy |
| Pre-dilution concentrations of A³IS and antibiotics. | A³IS 0.5% GOX | Velocef 500 mg | Amoxicillin 500 mg | Clindamycin 1.00 g | Augmentin 1.00 g |
| Final dilutions of A³IS and antibiotics for checkerboard synergy test | A³IS 3% | Velocef 1:100,000 | Amoxicillin 1:3,200,000 | Clindamycin 1:100 | Augmentin 1:1,600,000 |
| MICs for A³IS & antibiotics on S. aureus NCIMB 9587. | A³IS ⅛ | Velocef ¼ | Amoxicillin ¼ | Clindamycin ½ | Augmentin ⅛ |
| FICs for combination (A³IS + antibiotic) on S. aureus NCIMB 9587 for checkerboard synergy tests. | | A³IS + Velocef 0.1248 | A³IS + Amoxicillin 1.5 | A³IS + Clindamycin 0.125 | A³IS + Augmentin 2.00 |
| | | Synergy | No Synergy | Synergy | No Synergy |

Synergy tests were performed in 96-well microtiter plates containing the A³IS (from Example 3)/antibiotic combinations in two fold dilutions dispensed in a checkerboard fashion on the day of the assay. Each well contained 0.1 mL of A³IS/antimicrobial combinations. A suspension of S. aureus test culture was prepared from an overnight broth culture to yield a final inoculum of approximately $3 \times 10^5$ to $5 \times 10^5$ CFU/mL. Twenty microliters of this suspension was added to all but the sterility control wells. MICs were read after overnight incubation at 35° C. Growth and sterility controls were included in each plate. Each isolate was tested twice. Growth was determined by visually examining each well for evidence of turbidity.

Synergy Tests Interpretation

For the first clear well in each row of the microtiter plate containing both antimicrobial agents, the fractional inhibitory concentration (FIC) was calculated as follows: FIC of drug A ($FIC_A$)=MIC of drug A in combination/MIC of drug A alone, and the FIC of drug B ($FIC_B$)=MIC of drug B in combination/MIC of drug B alone. The sum of both FICs in each well was used to classify the combination of antimicrobial agents as synergistic effect when FIC indexes were ≤0.5; partial synergy FIC >0.5 but <1; additive FIC=1.0; indifferent effect when values were >1 and <4 and antagonistic when values were ≥4.0 (Eliopolus G M, Moellering R C Jr: *Antimicrobial combinations. In Antibiotics in Laboratory medicine*. 3rd edition. Williams and Wilkins, Co. Baltimore, Md. USA; 2000:432-49).

The combination of A³IS/Zinacef, A³IS/Velocef and A³IS/Clindamycin show an FIC ≤0.5 indicating a synergistic effect with these combinations. An indifferent effect was observed with the other A³IS/antibiotic combinations tested. None of the combinations showed an antagonistic effect.

Conclusion

The ability of A³IS to mediate a synergistic effect when used in combination with a number of single antibiotics has clinical potential. While synergism has been previously demonstrated with some antibiotic combinations, A³IS provides an antimicrobial vector to which other antibiotics may be added to give a greater antimicrobial effect than is possible with the antibiotic alone.

The invention claimed is:

1. An antimicrobial composition comprising:
   (i) a storage-stable antimicrobial and immunostimulatory system comprising glucose oxidase, D-glucose, one or more of sucrose, fructose or maltose, and a hydrogen peroxide source in an aqueous solution
       wherein an effective amount of glucose oxidase is present in an amount sufficient to provide activity of at least 10 U per 100 g of system;
       wherein D-glucose is present from approximately 20% to 85% by weight based on the weight of the total system;
       one or more of sucrose, fructose or maltose are present from approximately 10% to 70% by weight based on the weight of the total system;

water is present from 10 to 20% by weight based on the weight of the total system;

the system has a pH from approximately 4 to 8; and the system provides a two-stage hydrogen peroxide release in which
  (a) endogenously produced hydrogen peroxide is storage stable for one year or longer and is bioavailable within the system at a level of at least 10 mg per liter for immediate release; and
  (b) sustained release of further hydrogen peroxide for at least a twenty-four hour period occurs upon administration or application of the system and (ii) an antibiotic Lincosamide or Cephalosporin; or an antifungal agent selected from one or more of Clotrimazole, Cyclopiroxolamine, Terbidifine or Ketoconazole.

2. An antimicrobial composition according to claim 1 in the form of a combined preparation.

3. The antimicrobial composition according to claim 1 wherein the hydrogen peroxide source and the antimicrobial agent are for topical administration.

4. The antimicrobial composition according to claim 1 which provides for an efficacy greater than the efficacy of either the hydrogen peroxide source or the antimicrobial agent administered alone.

5. The antimicrobial composition according to claim 1 wherein the Lincosamide is Clindamycin.

6. The antimicrobial composition according to claim 1, wherein the Cephalosporin is Cefradine or Cefuroxime.

7. The antimicrobial composition according to claim 1, wherein the microbial infection is bacterial or fungal infection.

8. The antimicrobial composition according to claim 1 wherein the microbial infection is a skin infection, a nail infection, mastitis, MRSA or other antibiotic resistant infection.

9. The antimicrobial composition according to claim 1 wherein the storage-stable antimicrobial and immunostimulatory system or the antibiotic or antifungal agent are for enteral or parenteral administration.

10. A method of treating a microbial infection comprising administering a therapeutically effective amount of an antimicrobial composition comprising
  (i) a storage-stable antimicrobial and immunostimulatory system comprising glucose oxidase, D-glucose, one or more of sucrose, fructose or maltose, and hydrogen peroxide in an aqueous solution wherein:
    a. the glucose oxidase is present in an amount sufficient to provide activity of at least 10 U per 100 g of system,
    b. the D-glucose is present from approximately 20% to 85% by weight based on the weight of the total system,
    c. one or more of sucrose, fructose or maltose are present from approximately 10% to 70% by weight based on the weight of the total system, and
    d. water is present from 10 to 20% by weight based on the weight of the total system; the system has a pH from approximately 4 to 8, and
  wherein the system provides a two-stage hydrogen peroxide release in which (a) storage-stable endogenously produced hydrogen peroxide is bioavailable within the system at a level of at least 10 mg per liter for immediate release; and (b) sustained release of further hydrogen peroxide for at least a twenty-four hour period occurs upon administration or application of the system; and
  (ii) an antibiotic Lincosamide or Cephalosporin; or an antifungal agent selected from one or more of Clotrimazole, Cyclopiroxalomine, Terbidifine or Ketoconazole, to a patient in need thereof.

11. The method according to claim 10 wherein (i) and (ii) are administered simultaneously.

12. The method according to claim 10 wherein (i) and (ii) are administered separately.

13. The method according to claim 10 wherein (i) and (ii) are administered sequentially.

* * * * *